US012600960B2

(12) United States Patent      (10) Patent No.: US 12,600,960 B2
Paloheimo et al.      (45) Date of Patent: Apr. 14, 2026

(54) XYLANASE VARIANTS

(71) Applicant: AB Enzymes Finland Oy, Rajamäki (FI)

(72) Inventors: Marja Paloheimo, Rajamäki (FI); Kari Juntunen, Rajamäki (FI); Ossi Turunen, Nummela (FI); Pihla Ahola, Rajamäki (FI); Pasi Taipalus, Rajamäki (FI); Eugen Müller, Darmstadt (DE); Jukka Savolainen, Tampere (FI); Kim Langfelder, Darmstadt (DE); Terhi Puranen, Rajamäki (FI)

(73) Assignee: AB Enzymes Finland Oy, Rajamäki (FI)

( * ) Notice: Subject to any disclaimer, the term of this patent is extended or adjusted under 35 U.S.C. 154(b) by 336 days.

(21) Appl. No.: 18/269,907

(22) PCT Filed: Dec. 23, 2021

(86) PCT No.: PCT/FI2021/050911
§ 371 (c)(1),
(2) Date: Jun. 27, 2023

(87) PCT Pub. No.: WO2022/144500
PCT Pub. Date: Jul. 7, 2022

(65) Prior Publication Data
US 2025/0019682 A1     Jan. 16, 2025

(30) Foreign Application Priority Data
Dec. 28, 2020   (EP) ..................................... 20217335

(51) Int. Cl.
*C12N 9/24*     (2006.01)
*A23K 20/189*     (2016.01)
*D21C 9/10*     (2006.01)

(52) U.S. Cl.
CPC .......... *C12N 9/2482* (2013.01); *A23K 20/189* (2016.05); *C12Y 302/01008* (2013.01); *D21C 9/1036* (2013.01); *C07K 2319/02* (2013.01); *C07K 2319/50* (2013.01)

(58) Field of Classification Search
CPC .... C12N 9/2482; C12N 15/80; A23K 20/189; A23K 10/14; A23K 50/10; C12Y 302/01008; D21C 9/1036; D21C 5/005; C07K 2319/02; C07K 2319/50; C12P 19/02; C12P 19/14
See application file for complete search history.

(56) References Cited

U.S. PATENT DOCUMENTS

| | | | |
|---|---|---|---|
| 7,060,482 B1 | 6/2006 | Sung et al. | |
| 7,348,171 B2 | 3/2008 | Pierce et al. | |
| 7,348,172 B2 | 3/2008 | Paloheimo et al. | |
| 8,846,364 B2 * | 9/2014 | Fenel ............. | C12Y 302/01008 |
| | | | 435/200 |

FOREIGN PATENT DOCUMENTS

| | | |
|---|---|---|
| EP | 1737951 B1 | 5/2010 |
| WO | 9727306 A1 | 7/1997 |
| WO | 0127252 A1 | 4/2001 |
| WO | 2005108565 A2 | 11/2005 |
| WO | 2011109524 A2 | 9/2011 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Extended European Search Report of 20217335.7, mailed Jul. 12, 2021.
International Search Report for PCT/FI2021/050911, mailed Mar. 28, 2022.
Bailey, M. J, et al., "Interlaboratory testing of methods for assay of xylanase activity", J. Biotechnol., 23, 1992, 257-270.

(Continued)

*Primary Examiner* — Ganapathirama Raghu
(74) *Attorney, Agent, or Firm* — Elmore Patent Law Group, P.C.; Joseph C. Zucchero; Carolyn S. Elmore

(57) ABSTRACT

A variant polypeptide of xylanase, and a fusion protein and an enzyme composition comprising the variant polypeptide, a recombinant host cell for production of the variant polypeptide, methods for using it and its use, is disclosed comprising an amino acid sequence having at least 79%, but less than 100% amino acid sequence identity with amino acids 1-191 of SEQ ID NO: 1, wherein the amino acid sequence has xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

20 Claims, 7 Drawing Sheets
Specification includes a Sequence Listing.

(56)          References Cited

OTHER PUBLICATIONS

Karhunen, T. A, et al., "High frequency one-step gene replacement in Trichoderma reesei. I. Endoglucanase I overproduction", Mol. Gen. Genet., 241, 1993, 515-522.

Leskinen, S., et al., "Thermostable xylanases, Xyn10A and Xyn11A, from the actinomycete Nonomuraea flexuosa: isolation of the genes and characterization of recombinant Xyn11A polypeptides produced in Trichoderma reesei", Appl. Microbiol. Biotechnol., 67(4)doi: 10.1007/s00253-004-1797-x, 495-505.

Paloheimo, M., et al., "Increased production of xylanase by expression of a truncated version of the xyn11A gene from Nonomuraea flexuosa in Trichoderma reesei", Appl. Environ. Microbiol. 73(10)doi:10.1128/AEM.02967-06, 3215-3224.

Penttila, M., et al., "A versatile transformation system for the cellulolytic filamentous fungus Trichoderma reesei", Gene, 61(2) https://www.sciencedirect.com/science/article/abs/pii0378111987901107, 155-164.

Sievers, F., et al., "Fast, scalable generation of high-quality protein multiple sequence alignments using Clustal Omega", Mol. Syst. Biol., 7:539doi:10.1038/msb.2011.75, 1-6.

* cited by examiner

Connects to Fig.
1B

Connects to Fig.
1A

WP_121218507.1_39-223 0.06637
WP_033431747.1_42-228 0.03349
WP_138698470.1_45-229 0.02956
WP_143737579.1_43-227 0.01876
WP_139572113.1_43-227 0.00847
WP_033585310.1_40-227 0.01316
WP_142647532.1_40-227 0.0119
WP_142648738.1_40-229 0.01264
WP_142617570.1_40-227 0.00274
WP_142623023.1_40-227 0.01322
WP_148443159.1_32-216 0.01860
SBO97775.1_16-292 0.01354
WP_168015463.1_43-227 0.00562
WP_080037458.1_43-227 0.00519
WP_168087053.1_41-228 0.02836
WP_620540240.1_43-229 0.00466
WP_091086057.1_42-229 0.0184
WP_169946539.1_40-223 0.01745
WP_043622760.1_44-228 0.01018
WP_091582668.1_42-228 0.02122
WP_153284557.1_38-225 0
WP_139635521.1_38-225 0
WP_138684422.1_46-230 0.01239
WP_139785230.1_46-230 0.00924
WP_127931499.1_46-230 0.00872
WP_168118335.1_44-228 0.01891
WP_048558786.1_39-223 0.01552
WP_033332249.1_39-223 0
WP_152584018.1_33-217 0
WP_091586600.1_43-227 0.005
WP_108660383.1_43-227 0.00475
WP_068983273.1_43-227 0.00065
WP_167184279.1_43-227 0.00213
WP_132341876.1_37-227 0
WP_138288668.1_37-227 0
WP_132641673.1_37-224 0.01325
WP_132686691.1_38-228 0.00503
WP_132518135.1_40-227 0.01893
WP_111174969.1_40-224 0.0074
WP_132608039.1_44-228 0.01963
WP_108243763.1_40-224 0.03068
WP_148034064.1_45-229 0.0288

```
AM24  DTTITQNQTGYDNGYFYSFWTDAPGTVSMTLHSGGSYSTSWRNTGNFVAGKGWSTGGRRT  60  SEQ ID NO: 1
XB1   QAAVTTNQTGTNNGYWYSFWTDAQGTVSMELGSGGNYSTSWRNTGNFVAGKGWQTGGRRT  60  SEQ ID NO: 30
XB2   SAAITSNQTGTHNGYFYSFWTDSPGTVSMELGSGGNYSTSWRNTGNFVAGTGWSTGGRRS  60  SEQ ID NO: 33
XB3   NAAITSNQTGTNNGYFYSFWTDAPGTVSMELGSGGNYSTSWRNTGNFVAGKGWSTGGRRT  60  SEQ ID NO: 36
XB4   DTVVTSNQTGTNNGYYYSFWTDAPGTVSMTLSSGGSYSTSWRNTGNFVAGKGWSNGARRT  60  SEQ ID NO: 39
XB5   AAPVTSNQTGTIHDGYFYSFWTDAPGTVSMELGSGGNYSTSWRNTGNFVAGKGWSTGGRRT 60  SEQ ID NO: 42
XB6   DTTITQNQTGYDNGYFYSFRTDAPGTVSMTLHSGGSYSTSWRNTGLFLAGKGWSTGGRRT  60  SEQ ID NO: 45
        : :.****  .::**:;***  * ***.:.********** *:**..*.**..**:

AM24  VTYNASFNPSGNAYLTLYGWTRNPLVEYYIVESWGTYRPTGTYKGTVTTDGGTYDIYETW  120 SEQ ID NO: 1
XB1   VSYSGSFNPSGNAYLTLYGWTRNPLIEYYIVDNWGTYRPTGSFKGTVTSDGGTYDIYETT  120 SEQ ID NO: 30
XB2   VTYSASFNPSGNSYLTLYGWTRNPLVEYYIVDNWGTYRPTGTHMGTVTTDGGTYDIYRTR  120 SEQ ID NO: 33
XB3   VSYSGSFNPSGNAYLTLYGWTRNPLIEYYIVDNWGTYRPTGEYRGTVTSDGGTYDIYKTT  120 SEQ ID NO: 36
XB4   VTYSGSFNPSGNAYLTLYGWTANPLVEYYIVDNWGTYRPTGTYKGTVTSDGGTYDIYKTT  120 SEQ ID NO: 39
XB5   VTYSGSFNPSGNAYLTLYGWTRNPLVEYYIVDNWGTYRPTGTYKGTVTSDGGTYDIYETT  120 SEQ ID NO: 42
XB6   VTYNASFNPSGNARLTLYGWTRNPLVSYHIVESWGTYRPTGTYKGTVTTDGGTYDIYETW  120 SEQ ID NO: 45
        *.:.******* .********:*** ***..:.*:.:.**********  ****.:

AM24  RYNAPSIEGTRTFQQFWSVRQQKRTSGTITIGNHFDAWARAGMNLGSHD-YQIMATEGYQ  179 SEQ ID NO: 1
XB1   RTNAPSIEGTRTFKQFWSVRQQKKTGGTITAGNHFDAWSRAGMQLGNHD-YMIMATEGYQ  179 SEQ ID NO: 30
XB2   RTNAPSIEGTRSFDQYWSVRQSRRSSGTITSGNHFDAWARAGMNLGSHD-YMIMATEGYQ  179 SEQ ID NO: 33
XB3   RYDAPSIEGTRTFDQYWSVRQSKRTGGSITSGNHFDAWARQGMNLGNHD-YMILATEGYQ  179 SEQ ID NO: 36
XB4   RYNAPSVEGVRTFDQYWSVRQSRRTGGTITAGNHFDAWARAGMPLGNFKYYMIMATEGYR  180 SEQ ID NO: 39
XB5   RYNAPSIEGTRTFKQYWSVRQSRRTGGTITSGNHFDAWARYGMSLGSHD-YMIMATEGYQ  179 SEQ ID NO: 42
XB6   RYNAPSIEGTRTYQQFWSVRQQKRTSGTITIGNHFDAWARAGMNLGSHD-YQIMATEGYQ  179 SEQ ID NO: 45
        * :***:**.*:. ::.*****:.::.:**:** *********:.* ** **.:****:

AM24  SSGSSTVSISEGGNPGNPGNPGNPGNPGNPGGGCVATL  220 SEQ ID NO: 1
XB1   SSGSSNITIGGGTNP-----------------------  194 SEQ ID NO: 30
XB2   SSGSSNVTLGSS---------------------------  191 SEQ ID NO: 33
XB3   SSGNSNITIGSGGGNP-----------------------  195 SEQ ID NO: 36
XB4   SSGNSSIRVGS----------------------------  191 SEQ ID NO: 39
XB5   SSGSSNITVGGSSNP------------------------  194 SEQ ID NO: 42
XB6   SSGSSTVSISEG---------------------------  191 SEQ ID NO: 45
        ***.*.:*:  :.
```

Fig. 2

SEQUENCE LISTING

<160> NUMBER OF SEQ ID NOS: 98

<210> SEQ ID NO 1
<211> LENGTH: 220
<212> TYPE: PRT
<213> ORGANISM: Artificial Sequence

```
<220> FEATURE:
<223> OTHER INFORMATION: variant

<400> SEQUENCE: 1

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
                20                  25                  30

Ser Gly Gly Ser Tyr Ser Thr Ser Trp Arg Asn Thr Gly Asn Phe Val
            35                  40                  45

Ala Gly Lys Gly Trp Ser Thr Gly Gly Arg Arg Thr Val Thr Tyr Asn
        50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
            195                 200                 205

Pro Gly Asn Pro Gly Gly Gly Cys Val Ala Thr Leu
    210                 215                 220

<210> SEQ ID NO 2
<211> LENGTH: 220
<212> TYPE: PRT
<213> ORGANISM: Artificial Sequence
<220> FEATURE:
<223> OTHER INFORMATION: variant

<400> SEQUENCE: 2

Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Ile Met Cys Leu His
                20                  25                  30

Ser Gly Gly Ser Tyr Ser Thr Ser Trp Arg Asn Thr Gly Asn Phe Val
            35                  40                  45

Ala Gly Lys Gly Trp Ser Thr Gly Gly Arg Arg Thr Val Thr Tyr Asn
        50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
```

-continued

|     | 115 |     |     | 120 |     |     | 125 |     |     |
|-----|-----|-----|-----|-----|-----|-----|-----|-----|-----|

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu
    210                 215                 220

<210> SEQ ID NO 3
<211> LENGTH: 220
<212> TYPE: PRT
<213> ORGANISM: Artificial Sequence
<220> FEATURE:
<223> OTHER INFORMATION: variant

<400> SEQUENCE: 3

Asp Thr Cys Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Cys Leu His
                20                  25                  30

Ser Gly Gly Ser Tyr Ser Thr Ser Trp Arg Asn Thr Gly Asn Phe Val
                35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
                100                 105                 110

Thr Tyr Asp Ile Tyr Glu Thr Trp Arg Tyr Asn Ala Pro Ser Ile Glu
                115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu
    210                 215                 220

<210> SEQ ID NO 4
<211> LENGTH: 220
<212> TYPE: PRT
<213> ORGANISM: Artificial Sequence
<220> FEATURE:
<223> OTHER INFORMATION: variant

<400> SEQUENCE: 4

```
Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Ser Met Cys Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
        50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
            195                 200                 205

Pro Gly Asn Pro Gly Gly Gly Cys Val Ala Thr Leu
    210                 215                 220
```

<210> SEQ ID NO 5
<211> LENGTH: 220
<212> TYPE: PRT
<213> ORGANISM: Artificial Sequence
<220> FEATURE:
<223> OTHER INFORMATION: variant

<400> SEQUENCE: 5

```
Asp Thr Cys Ile Thr Gln Asn Gln Thr Gly Tyr Asp Asn Gly Tyr Phe
1               5                   10                  15

Tyr Ser Phe Trp Thr Asp Ala Pro Gly Thr Val Ile Met Cys Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
        50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125
```

```
Gly Thr Arg Thr Phe Gln Gln Phe Trp Ser Val Arg Gln Gln Lys Arg
    130                 135                 140
```

```
Thr Ser Gly Thr Ile Thr Ile Gly Asn His Phe Asp Ala Trp Ala Arg
145                 150                 155                 160
```

```
Ala Gly Met Asn Leu Gly Ser His Asp Tyr Gln Ile Met Ala Thr Glu
                165                 170                 175
```

```
Gly Tyr Gln Ser Ser Gly Ser Ser Thr Val Ser Ile Ser Glu Gly Gly
                180                 185                 190
```

```
Asn Pro Gly Asn Pro Gly Asn Pro Gly Asn Pro Gly Asn Pro Gly Asn
                195                 200                 205
```

```
Pro Gly Asn Pro Gly Gly Gly Cys Val Ala Thr Leu
    210                 215                 220
```

<210> SEQ ID NO 6
<211> LENGTH: 220
<212> TYPE: PRT
<213> ORGANISM: Artificial Sequence
<220> FEATURE:
<223> OTHER INFORMATION: variant

<400> SEQUENCE: 6

```
Asp Thr Thr Ile Thr Gln Asn Gln Thr Gly Tyr Asp Asn Gly Tyr Phe
1               5                   10                  15
```

```
Tyr Ser Phe Trp Thr Asp Ser Pro Gly Thr Val Ser Met Thr Leu His
                20                  25                  30
```

```
Ser Gly Gly Ser Tyr Ser Thr Ser Trp Arg Asn Thr Gly Asn Phe Val
                35                  40                  45
```

```
Ala Gly Lys Gly Trp Ser Thr Gly Gly Arg Arg Thr Val Thr Tyr Asn
    50                  55                  60
```

```
Ala Ser Phe Asn Pro Ser Gly Asn Ala Tyr Leu Thr Leu Tyr Gly Trp
65                  70                  75                  80
```

```
Thr Arg Asn Pro Leu Val Glu Tyr Tyr Ile Val Glu Ser Trp Gly Thr
                85                  90                  95
```

```
Tyr Arg Pro Thr Gly Thr Tyr Lys Gly Thr Val Thr Thr Asp Gly Gly
                100                 105                 110
```

```
Thr Tyr Asp Ile Tyr Glu Thr Trp Arg Tyr Asn Ala Pro Ser Ile Glu
                115                 120                 125
```

```
Gly Thr Arg Thr Phe Gln Gln Phe Trp Ser Val Arg Gln Gln Lys Arg
    130                 135                 140
```

```
Thr Ser Gly Thr Ile Thr Ile Gly Asn His Phe Asp Ala Trp Ala Arg
145                 150                 155                 160
```

```
Ala Gly Met Asn Leu Gly Ser His Asp Tyr Gln Ile Met Ala Thr Glu
                165                 170                 175
```

```
Gly Tyr Gln Ser Ser Gly Ser Ser Thr Val Ser Ile Ser Glu Gly Gly
                180                 185                 190
```

```
Asn Pro Gly Asn Pro Gly Asn Pro Gly Asn Pro Gly Asn Pro Gly Asn
                195                 200                 205
```

```
Pro Gly Asn Pro Gly Gly Gly Cys Val Ala Thr Leu
    210                 215                 220
```

<210> SEQ ID NO 7
<211> LENGTH: 220
<212> TYPE: PRT
<213> ORGANISM: Artificial Sequence
<220> FEATURE:
<223> OTHER INFORMATION: variant

<400> SEQUENCE: 7

-continued

```
Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ile Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
            195                 200                 205

Pro Gly Asn Pro Gly Gly Gly Cys Val Ala Thr Leu
    210                 215                 220
```

```
<210> SEQ ID NO 8
<211> LENGTH: 220
<212> TYPE: PRT
<213> ORGANISM: Artificial Sequence
<220> FEATURE:
<223> OTHER INFORMATION: variant

<400> SEQUENCE: 8
```

```
Asp Thr Thr Ile Thr Gln Asn Gln Thr Gly Tyr Asp Asn Gly Tyr Phe
1               5                   10                  15

Tyr Ser Phe Trp Thr Asp Ser Pro Gly Thr Val Ile Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
    130                 135                 140
```

```
Thr Ser Gly Thr Ile Thr Ile Gly Asn His Phe Asp Ala Trp Ala Arg
145             150             155                 160

Ala Gly Met Asn Leu Gly Ser His Asp Tyr Gln Ile Met Ala Thr Glu
            165             170             175

Gly Tyr Gln Ser Ser Gly Ser Ser Thr Val Ser Ile Ser Glu Gly Gly
            180             185             190

Asn Pro Gly Asn Pro Gly Asn Pro Gly Asn Pro Gly Asn Pro Gly Asn
        195             200             205

Pro Gly Asn Pro Gly Gly Gly Cys Val Ala Thr Leu
    210             215             220
```

<210> SEQ ID NO 9
<211> LENGTH: 220
<212> TYPE: PRT
<213> ORGANISM: Artificial Sequence
<220> FEATURE:
<223> OTHER INFORMATION: variant

<400> SEQUENCE: 9

```
Asp Thr Cys Ile Thr Gln Asn Gln Thr Gly Tyr Asp Asn Gly Tyr Phe
1               5               10              15

Tyr Ser Phe Trp Thr Asp Tyr Pro Gly Thr Val Ile Met Cys Leu His
            20              25              30

Ser Gly Gly Ser Tyr Ser Thr Ser Trp Arg Asn Thr Gly Asn Phe Val
        35              40              45

Ala Gly Lys Gly Trp Ser Thr Gly Gly Arg Arg Thr Val Thr Tyr Asn
    50              55              60

Ala Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Glu Ser Trp Gly Thr
            85              90              95

Tyr Arg Pro Thr Gly Thr Tyr Lys Gly Thr Val Thr Thr Asp Gly Gly
        100             105             110

Thr Tyr Asp Ile Tyr Glu Thr Trp Arg Tyr Asn Ala Pro Ser Ile Glu
        115             120             125

Gly Thr Arg Thr Phe Gln Gln Phe Trp Ser Val Arg Gln Gln Lys Arg
    130             135             140

Thr Ser Gly Thr Ile Thr Ile Gly Asn His Phe Asp Ala Trp Ala Arg
145             150             155                 160

Ala Gly Met Asn Leu Gly Ser His Asp Tyr Gln Ile Met Ala Thr Glu
            165             170             175

Gly Tyr Gln Ser Ser Gly Ser Ser Thr Val Ser Ile Ser Glu Gly Gly
            180             185             190

Asn Pro Gly Asn Pro Gly Asn Pro Gly Asn Pro Gly Asn Pro Gly Asn
        195             200             205

Pro Gly Asn Pro Gly Gly Gly Cys Val Ala Thr Leu
    210             215             220
```

<210> SEQ ID NO 10
<211> LENGTH: 220
<212> TYPE: PRT
<213> ORGANISM: Artificial Sequence
<220> FEATURE:
<223> OTHER INFORMATION: variant

<400> SEQUENCE: 10

```
Asp Thr Cys Ile Thr Gln Asn Gln Thr Gly Tyr Asp Asn Gly Tyr Phe
```

```
1               5                    10                   15

Tyr Ser Phe Trp Thr Asp His Pro Gly Thr Val Ile Met Cys Leu His
                20               25               30

Ser Gly Gly Ser Tyr Ser Thr Ser Trp Arg Asn Thr Gly Asn Phe Val
            35               40               45

Ala Gly Lys Gly Trp Ser Thr Gly Gly Arg Arg Thr Val Thr Tyr Asn
    50               55               60

Ala Ser Phe Asn Pro Ser Gly Asn Ala Tyr Leu Thr Leu Tyr Gly Trp
65               70               75               80

Thr Arg Asn Pro Leu Val Glu Tyr Tyr Ile Val Glu Ser Trp Gly Thr
                85               90               95

Tyr Arg Pro Thr Gly Thr Tyr Lys Gly Thr Val Thr Thr Asp Gly Gly
            100              105              110

Thr Tyr Asp Ile Tyr Glu Thr Trp Arg Tyr Asn Ala Pro Ser Ile Glu
            115              120              125

Gly Thr Arg Thr Phe Gln Gln Phe Trp Ser Val Arg Gln Gln Lys Arg
    130              135              140

Thr Ser Gly Thr Ile Thr Ile Gly Asn His Phe Asp Ala Trp Ala Arg
145              150              155              160

Ala Gly Met Asn Leu Gly Ser His Asp Tyr Gln Ile Met Ala Thr Glu
                165              170              175

Gly Tyr Gln Ser Ser Gly Ser Ser Thr Val Ser Ile Ser Glu Gly Gly
            180              185              190

Asn Pro Gly Asn Pro Gly Asn Pro Gly Asn Pro Gly Asn Pro Gly Asn
            195              200              205

Pro Gly Asn Pro Gly Gly Gly Cys Val Ala Thr Leu
    210              215              220
```

```
<210> SEQ ID NO 11
<211> LENGTH: 220
<212> TYPE: PRT
<213> ORGANISM: Artificial Sequence
<220> FEATURE:
<223> OTHER INFORMATION: variant

<400> SEQUENCE: 11

Asp Thr Cys Ile Thr Gln Asn Gln Thr Gly Tyr Asp Asn Gly Tyr Phe
1               5                    10                   15

Tyr Ser Phe Trp Thr Asp Thr Pro Gly Thr Val Ile Met Cys Leu His
                20               25               30

Ser Gly Gly Ser Tyr Ser Thr Ser Trp Arg Asn Thr Gly Asn Phe Val
            35               40               45

Ala Gly Lys Gly Trp Ser Thr Gly Gly Arg Arg Thr Val Thr Tyr Asn
    50               55               60

Ala Ser Phe Asn Pro Ser Gly Asn Ala Tyr Leu Thr Leu Tyr Gly Trp
65               70               75               80

Thr Arg Asn Pro Leu Val Glu Tyr Tyr Ile Val Glu Ser Trp Gly Thr
                85               90               95

Tyr Arg Pro Thr Gly Thr Tyr Lys Gly Thr Val Thr Thr Asp Gly Gly
            100              105              110

Thr Tyr Asp Ile Tyr Glu Thr Trp Arg Tyr Asn Ala Pro Ser Ile Glu
            115              120              125

Gly Thr Arg Thr Phe Gln Gln Phe Trp Ser Val Arg Gln Gln Lys Arg
    130              135              140

Thr Ser Gly Thr Ile Thr Ile Gly Asn His Phe Asp Ala Trp Ala Arg
```

```
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu
    210                 215                 220
```

```
<210> SEQ ID NO 12
<211> LENGTH: 220
<212> TYPE: PRT
<213> ORGANISM: Artificial Sequence
<220> FEATURE:
<223> OTHER INFORMATION: variant

<400> SEQUENCE: 12

Asp Thr Cys Ile Thr Gln Asn Gln Thr Gly Tyr Asp Asn Gly Tyr Phe
1               5                   10                  15

Tyr Ser Phe Trp Thr Asp Met Pro Gly Thr Val Ile Met Cys Leu His
                20                  25                  30

Ser Gly Gly Ser Tyr Ser Thr Ser Trp Arg Asn Thr Gly Asn Phe Val
                35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
                100                 105                 110

Thr Tyr Asp Ile Tyr Glu Thr Trp Arg Tyr Asn Ala Pro Ser Ile Glu
                115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu
    210                 215                 220
```

```
<210> SEQ ID NO 13
<211> LENGTH: 220
<212> TYPE: PRT
<213> ORGANISM: Artificial Sequence
<220> FEATURE:
<223> OTHER INFORMATION: variant

<400> SEQUENCE: 13

Asp Thr Cys Ile Thr Gln Asn Gln Thr Gly Tyr Asp Asn Gly Tyr Phe
1               5                   10                  15
```

-continued

```
Tyr Ser Phe Trp Thr Asp Arg Pro Gly Thr Val Ile Met Cys Leu His
             20              25              30

Ser Gly Gly Ser Tyr Ser Thr Ser Trp Arg Asn Thr Gly Asn Phe Val
         35              40              45

Ala Gly Lys Gly Trp Ser Thr Gly Gly Arg Arg Thr Val Thr Tyr Asn
50              55              60

Ala Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Glu Ser Trp Gly Thr
             85              90              95

Tyr Arg Pro Thr Gly Thr Tyr Lys Gly Thr Val Thr Thr Asp Gly Gly
             100             105             110

Thr Tyr Asp Ile Tyr Glu Thr Trp Arg Tyr Asn Ala Pro Ser Ile Glu
             115             120             125

Gly Thr Arg Thr Phe Gln Gln Phe Trp Ser Val Arg Gln Gln Lys Arg
         130             135             140

Thr Ser Gly Thr Ile Thr Ile Gly Asn His Phe Asp Ala Trp Ala Arg
145             150             155             160

Ala Gly Met Asn Leu Gly Ser His Asp Tyr Gln Ile Met Ala Thr Glu
             165             170             175

Gly Tyr Gln Ser Ser Gly Ser Ser Thr Val Ser Ile Ser Glu Gly Gly
             180             185             190

Asn Pro Gly Asn Pro Gly Asn Pro Gly Asn Pro Gly Asn Pro Gly Asn
         195             200             205

Pro Gly Asn Pro Gly Gly Gly Cys Val Ala Thr Leu
   210             215             220
```

```
<210> SEQ ID NO 14
<211> LENGTH: 220
<212> TYPE: PRT
<213> ORGANISM: Artificial Sequence
<220> FEATURE:
<223> OTHER INFORMATION: variant

<400> SEQUENCE: 14
```

```
Asp Thr Cys Ile Thr Gln Asn Gln Thr Gly Tyr Asp Asn Gly Tyr Phe
1               5               10              15

Tyr Ser Phe Trp Thr Asp Ser Pro Gly Thr Val Leu Met Cys Leu His
             20              25              30

Ser Gly Gly Ser Tyr Ser Thr Ser Trp Arg Asn Thr Gly Asn Phe Val
         35              40              45

Ala Gly Lys Gly Trp Ser Thr Gly Gly Arg Arg Thr Val Thr Tyr Asn
50              55              60

Ala Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Glu Ser Trp Gly Thr
             85              90              95

Tyr Arg Pro Thr Gly Thr Tyr Lys Gly Thr Val Thr Thr Asp Gly Gly
             100             105             110

Thr Tyr Asp Ile Tyr Glu Thr Trp Arg Tyr Asn Ala Pro Ser Ile Glu
             115             120             125

Gly Thr Arg Thr Phe Gln Gln Phe Trp Ser Val Arg Gln Gln Lys Arg
         130             135             140

Thr Ser Gly Thr Ile Thr Ile Gly Asn His Phe Asp Ala Trp Ala Arg
145             150             155             160
```

```
Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu
        210                 215                 220
```

```
<210> SEQ ID NO 15
<211> LENGTH: 220
<212> TYPE: PRT
<213> ORGANISM: Artificial Sequence
<220> FEATURE:
<223> OTHER INFORMATION: variant

<400> SEQUENCE: 15
```

```
Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Arg Met Cys Leu His
                20                  25                  30

Ser Gly Gly Ser Tyr Ser Thr Ser Trp Arg Asn Thr Gly Asn Phe Val
                35                  40                  45

Ala Gly Lys Gly Trp Ser Thr Gly Gly Arg Arg Thr Val Thr Tyr Asn
        50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
                100                 105                 110

Thr Tyr Asp Ile Tyr Glu Thr Trp Arg Tyr Asn Ala Pro Ser Ile Glu
                115                 120                 125

Gly Thr Arg Thr Phe Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu
        210                 215                 220
```

```
<210> SEQ ID NO 16
<211> LENGTH: 220
<212> TYPE: PRT
<213> ORGANISM: Artificial Sequence
<220> FEATURE:
<223> OTHER INFORMATION: variant

<400> SEQUENCE: 16
```

```
Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Met Met Cys Leu His
                20                  25                  30
```

```
Ser Gly Gly Ser Tyr Ser Thr Ser Trp Arg Asn Thr Gly Asn Phe Val
    35              40              45

Ala Gly Lys Gly Trp Ser Thr Gly Gly Arg Arg Thr Val Thr Tyr Asn
50              55              60

Ala Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Glu Ser Trp Gly Thr
                85              90              95

Tyr Arg Pro Thr Gly Thr Tyr Lys Gly Thr Val Thr Thr Asp Gly Gly
            100             105             110

Thr Tyr Asp Ile Tyr Glu Thr Trp Arg Tyr Asn Ala Pro Ser Ile Glu
            115             120             125

Gly Thr Arg Thr Phe Gln Gln Phe Trp Ser Val Arg Gln Gln Lys Arg
    130             135             140

Thr Ser Gly Thr Ile Thr Ile Gly Asn His Phe Asp Ala Trp Ala Arg
145             150             155             160

Ala Gly Met Asn Leu Gly Ser His Asp Tyr Gln Ile Met Ala Thr Glu
                165             170             175

Gly Tyr Gln Ser Ser Gly Ser Ser Thr Val Ser Ile Ser Glu Gly Gly
            180             185             190

Asn Pro Gly Asn Pro Gly Asn Pro Gly Asn Pro Gly Asn Pro Gly Asn
            195             200             205

Pro Gly Asn Pro Gly Gly Gly Cys Val Ala Thr Leu
    210             215             220
```

<210> SEQ ID NO 17
<211> LENGTH: 220
<212> TYPE: PRT
<213> ORGANISM: Artificial Sequence
<220> FEATURE:
<223> OTHER INFORMATION: variant

<400> SEQUENCE: 17

```
Asp Thr Cys Ile Thr Gln Asn Gln Thr Gly Tyr Asp Asn Gly Tyr Phe
1               5               10              15

Tyr Ser Phe Trp Thr Asp Ser Pro Gly Thr Val Gln Met Cys Leu His
                20              25              30

Ser Gly Gly Ser Tyr Ser Thr Ser Trp Arg Asn Thr Gly Asn Phe Val
    35              40              45

Ala Gly Lys Gly Trp Ser Thr Gly Gly Arg Arg Thr Val Thr Tyr Asn
50              55              60

Ala Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Glu Ser Trp Gly Thr
                85              90              95

Tyr Arg Pro Thr Gly Thr Tyr Lys Gly Thr Val Thr Thr Asp Gly Gly
            100             105             110

Thr Tyr Asp Ile Tyr Glu Thr Trp Arg Tyr Asn Ala Pro Ser Ile Glu
            115             120             125

Gly Thr Arg Thr Phe Gln Gln Phe Trp Ser Val Arg Gln Gln Lys Arg
    130             135             140

Thr Ser Gly Thr Ile Thr Ile Gly Asn His Phe Asp Ala Trp Ala Arg
145             150             155             160

Ala Gly Met Asn Leu Gly Ser His Asp Tyr Gln Ile Met Ala Thr Glu
                165             170             175
```

```
Gly Tyr Gln Ser Ser Gly Ser Ser Thr Val Ser Ile Ser Glu Gly Gly
        180                 185                 190

Asn Pro Gly Asn Pro Gly Asn Pro Gly Asn Pro Gly Asn Pro Gly Asn
        195                 200                 205

Pro Gly Asn Pro Gly Gly Gly Cys Val Ala Thr Leu
        210                 215                 220
```

```
<210> SEQ ID NO 18
<211> LENGTH: 220
<212> TYPE: PRT
<213> ORGANISM: Artificial Sequence
<220> FEATURE:
<223> OTHER INFORMATION: variant

<400> SEQUENCE: 18
```

```
Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Tyr Met Cys Leu His
        20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
        100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
        180                 185                 190

Asn Pro Gly Asn Pro Gly Asn Pro Gly Asn Pro Gly Asn Pro Gly Asn
        195                 200                 205

Pro Gly Asn Pro Gly Gly Gly Cys Val Ala Thr Leu
        210                 215                 220
```

```
<210> SEQ ID NO 19
<211> LENGTH: 220
<212> TYPE: PRT
<213> ORGANISM: Artificial Sequence
<220> FEATURE:
<223> OTHER INFORMATION: variant

<400> SEQUENCE: 19
```

```
Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Trp Met Cys Leu His
        20                  25                  30

Ser Gly Gly Ser Tyr Ser Thr Ser Trp Arg Asn Thr Gly Asn Phe Val
```

-continued

```
              35                    40                    45
Ala Gly Lys Gly Trp Ser Thr Gly Gly Arg Arg Thr Val Thr Tyr Asn
    50                    55                    60
Ala Ser Phe Asn Pro Ser Gly Asn Ala Tyr Leu Thr Leu Tyr Gly Trp
65                    70                    75                    80
Thr Arg Asn Pro Leu Val Glu Tyr Tyr Ile Val Glu Ser Trp Gly Thr
                  85                    90                    95
Tyr Arg Pro Thr Gly Thr Tyr Lys Gly Thr Val Thr Thr Asp Gly Gly
              100                   105                   110
Thr Tyr Asp Ile Tyr Glu Thr Trp Arg Tyr Asn Ala Pro Ser Ile Glu
              115                   120                   125
Gly Thr Arg Thr Phe Gln Gln Phe Trp Ser Val Arg Gln Gln Lys Arg
    130                   135                   140
Thr Ser Gly Thr Ile Thr Ile Gly Asn His Phe Asp Ala Trp Ala Arg
145                   150                   155                   160
Ala Gly Met Asn Leu Gly Ser His Asp Tyr Gln Ile Met Ala Thr Glu
                  165                   170                   175
Gly Tyr Gln Ser Ser Gly Ser Ser Thr Val Ser Ile Ser Glu Gly Gly
              180                   185                   190
Asn Pro Gly Asn Pro Gly Asn Pro Gly Asn Pro Gly Asn Pro Gly Asn
              195                   200                   205
Pro Gly Asn Pro Gly Gly Gly Cys Val Ala Thr Leu
    210                   215                   220

<210> SEQ ID NO 20
<211> LENGTH: 220
<212> TYPE: PRT
<213> ORGANISM: Artificial Sequence
<220> FEATURE:
<223> OTHER INFORMATION: variant

<400> SEQUENCE: 20

Asp Thr Cys Ile Thr Gln Asn Gln Thr Gly Tyr Asp Asn Gly Tyr Phe
1                   5                     10                    15
Tyr Ser Phe Trp Thr Asp Ser Pro Gly Thr Val Thr Met Cys Leu His
                  20                    25                    30
Ser Gly Gly Ser Tyr Ser Thr Ser Trp Arg Asn Thr Gly Asn Phe Val
              35                    40                    45
Ala Gly Lys Gly Trp Ser Thr Gly Gly Arg Arg Thr Val Thr Tyr Asn
    50                    55                    60
Ala Ser Phe Asn Pro Ser Gly Asn Ala Tyr Leu Thr Leu Tyr Gly Trp
65                    70                    75                    80
Thr Arg Asn Pro Leu Val Glu Tyr Tyr Ile Val Glu Ser Trp Gly Thr
                  85                    90                    95
Tyr Arg Pro Thr Gly Thr Tyr Lys Gly Thr Val Thr Thr Asp Gly Gly
              100                   105                   110
Thr Tyr Asp Ile Tyr Glu Thr Trp Arg Tyr Asn Ala Pro Ser Ile Glu
              115                   120                   125
Gly Thr Arg Thr Phe Gln Gln Phe Trp Ser Val Arg Gln Gln Lys Arg
    130                   135                   140
Thr Ser Gly Thr Ile Thr Ile Gly Asn His Phe Asp Ala Trp Ala Arg
145                   150                   155                   160
Ala Gly Met Asn Leu Gly Ser His Asp Tyr Gln Ile Met Ala Thr Glu
                  165                   170                   175
Gly Tyr Gln Ser Ser Gly Ser Ser Thr Val Ser Ile Ser Glu Gly Gly
```

-continued

```
              180             185             190

Asn Pro Gly Asn Pro Gly Asn Pro Gly Asn Pro Gly Asn
        195             200             205

Pro Gly Asn Pro Gly Gly Gly Cys Val Ala Thr Leu
    210             215             220

<210> SEQ ID NO 21
<211> LENGTH: 220
<212> TYPE: PRT
<213> ORGANISM: Artificial Sequence
<220> FEATURE:
<223> OTHER INFORMATION: variant

<400> SEQUENCE: 21

Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Asn Met Cys Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
        195                 200                 205

Pro Gly Asn Pro Gly Gly Gly Cys Val Ala Thr Leu
    210             215             220

<210> SEQ ID NO 22
<211> LENGTH: 220
<212> TYPE: PRT
<213> ORGANISM: Artificial Sequence
<220> FEATURE:
<223> OTHER INFORMATION: variant

<400> SEQUENCE: 22

Asp Thr Cys Ile Thr Gln Asn Gln Thr Gly Tyr Asp Asn Gly Tyr Phe
1               5                   10                  15

Tyr Ser Phe Trp Thr Asp Ser Pro Gly Thr Val Val Met Cys Leu His
            20                  25                  30

Ser Gly Gly Ser Tyr Ser Thr Ser Trp Arg Asn Thr Gly Asn Phe Val
        35                  40                  45
```

-continued

```
Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
            195                 200                 205

Pro Gly Asn Pro Gly Gly Gly Cys Val Ala Thr Leu
    210                 215                 220
```

```
<210> SEQ ID NO 23
<211> LENGTH: 220
<212> TYPE: PRT
<213> ORGANISM: Artificial Sequence
<220> FEATURE:
<223> OTHER INFORMATION: variant

<400> SEQUENCE: 23
```

```
Asp Thr Cys Ile Thr Gln Asn Gln Thr Gly Tyr Asp Asn Gly Tyr Phe
1               5                   10                  15

Tyr Ser Phe Trp Thr Asp Arg Pro Gly Thr Val Leu Met Cys Leu His
                20                  25                  30

Ser Gly Gly Ser Tyr Ser Thr Ser Trp Arg Asn Thr Gly Asn Phe Val
            35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190
```

-continued

```
Asn Pro Gly Asn Pro Gly Asn Pro Gly Asn Pro Gly Asn Pro Gly Asn
        195                 200                 205

Pro Gly Asn Pro Gly Gly Gly Cys Val Ala Thr Leu
    210                 215                 220
```

```
<210> SEQ ID NO 24
<211> LENGTH: 220
<212> TYPE: PRT
<213> ORGANISM: Artificial Sequence
<220> FEATURE:
<223> OTHER INFORMATION: variant

<400> SEQUENCE: 24
```

```
Asp Thr Cys Ile Thr Gln Asn Gln Thr Gly Tyr Asp Asn Gly Tyr Phe
1               5                   10                  15

Tyr Ser Phe Trp Thr Asp Arg Pro Gly Thr Val Gln Met Cys Leu His
        20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
        100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
        180                 185                 190

Asn Pro Gly Asn Pro Gly Asn Pro Gly Asn Pro Gly Asn Pro Gly Asn
        195                 200                 205

Pro Gly Asn Pro Gly Gly Gly Cys Val Ala Thr Leu
    210                 215                 220
```

```
<210> SEQ ID NO 25
<211> LENGTH: 220
<212> TYPE: PRT
<213> ORGANISM: Artificial Sequence
<220> FEATURE:
<223> OTHER INFORMATION: variant

<400> SEQUENCE: 25
```

```
Asp Thr Cys Ile Thr Gln Asn Gln Thr Gly Tyr Asp Asn Gly Tyr Phe
1               5                   10                  15

Tyr Ser Phe Trp Thr Asp His Pro Gly Thr Val Leu Met Cys Leu His
        20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60
```

-continued

```
Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                    85                  90                  95

Tyr Arg Pro Thr Gly Thr Tyr Lys Gly Thr Val Thr Thr Asp Gly Gly
                100                 105                 110

Thr Tyr Asp Ile Tyr Glu Thr Trp Arg Tyr Asn Ala Pro Ser Ile Glu
                115                 120                 125

Gly Thr Arg Thr Phe Gln Gln Phe Trp Ser Val Arg Gln Gln Lys Arg
            130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
            195                 200                 205

Pro Gly Asn Pro Gly Gly Gly Cys Val Ala Thr Leu
        210                 215                 220

<210> SEQ ID NO 26
<211> LENGTH: 220
<212> TYPE: PRT
<213> ORGANISM: Artificial Sequence
<220> FEATURE:
<223> OTHER INFORMATION: variant

<400> SEQUENCE: 26

Asp Thr Cys Ile Thr Gln Asn Gln Thr Gly Tyr Asp Asn Gly Tyr Phe
1               5                   10                  15

Tyr Ser Phe Trp Thr Asp Thr Pro Gly Thr Val Leu Met Cys Leu His
                20                  25                  30

Ser Gly Gly Ser Tyr Ser Thr Ser Trp Arg Asn Thr Gly Asn Phe Val
            35                  40                  45

Ala Gly Lys Gly Trp Ser Thr Gly Gly Arg Arg Thr Val Thr Tyr Asn
        50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                    85                  90                  95

Tyr Arg Pro Thr Gly Thr Tyr Lys Gly Thr Val Thr Thr Asp Gly Gly
                100                 105                 110

Thr Tyr Asp Ile Tyr Glu Thr Trp Arg Tyr Asn Ala Pro Ser Ile Glu
                115                 120                 125

Gly Thr Arg Thr Phe Gln Gln Phe Trp Ser Val Arg Gln Gln Lys Arg
            130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
            195                 200                 205
```

```
Pro Gly Asn Pro Gly Gly Gly Cys Val Ala Thr Leu
    210             215             220

<210> SEQ ID NO 27
<211> LENGTH: 220
<212> TYPE: PRT
<213> ORGANISM: Artificial Sequence
<220> FEATURE:
<223> OTHER INFORMATION: variant

<400> SEQUENCE: 27

Asp Thr Cys Ile Thr Gln Asn Gln Thr Gly Tyr Asp Asn Gly Tyr Phe
1               5                   10                  15

Tyr Ser Phe Trp Thr Asp Trp Pro Gly Thr Val Ile Met Cys Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
        195                 200                 205

Pro Gly Asn Pro Gly Gly Gly Cys Val Ala Thr Leu
    210             215             220

<210> SEQ ID NO 28
<211> LENGTH: 220
<212> TYPE: PRT
<213> ORGANISM: Artificial Sequence
<220> FEATURE:
<223> OTHER INFORMATION: variant

<400> SEQUENCE: 28

Asp Thr Cys Ile Thr Gln Asn Gln Thr Gly Tyr Asp Asn Gly Tyr Phe
1               5                   10                  15

Tyr Ser Phe Trp Thr Asp Pro Pro Gly Thr Val Ile Met Cys Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
```

```
65              70              75              80

Thr Arg Asn Pro Leu Val Glu Tyr Tyr Ile Val Glu Ser Trp Gly Thr
                85              90              95

Tyr Arg Pro Thr Gly Thr Tyr Lys Gly Thr Val Thr Thr Asp Gly Gly
                100             105             110

Thr Tyr Asp Ile Tyr Glu Thr Trp Arg Tyr Asn Ala Pro Ser Ile Glu
                115             120             125

Gly Thr Arg Thr Phe Gln Gln Phe Trp Ser Val Arg Gln Gln Lys Arg
        130             135             140

Thr Ser Gly Thr Ile Thr Ile Gly Asn His Phe Asp Ala Trp Ala Arg
145             150             155             160

Ala Gly Met Asn Leu Gly Ser His Asp Tyr Gln Ile Met Ala Thr Glu
                165             170             175

Gly Tyr Gln Ser Ser Gly Ser Ser Thr Val Ser Ile Ser Glu Gly Gly
                180             185             190

Asn Pro Gly Asn Pro Gly Asn Pro Gly Asn Pro Gly Asn Pro Gly Asn
                195             200             205

Pro Gly Asn Pro Gly Gly Gly Cys Val Ala Thr Leu
        210             215             220
```

```
<210> SEQ ID NO 29
<211> LENGTH: 220
<212> TYPE: PRT
<213> ORGANISM: Artificial Sequence
<220> FEATURE:
<223> OTHER INFORMATION: variant

<400> SEQUENCE: 29
```

```
Asp Thr Cys Ile Thr Gln Asn Gln Thr Gly Tyr Asp Asn Gly Tyr Phe
1               5               10              15

Tyr Ser Phe Trp Thr Asp Ser Pro Gly Thr Val Pro Met Cys Leu His
                20              25              30

Ser Gly Gly Ser Tyr Ser Thr Ser Trp Arg Asn Thr Gly Asn Phe Val
        35              40              45

Ala Gly Lys Gly Trp Ser Thr Gly Gly Arg Arg Thr Val Thr Tyr Asn
        50              55              60

Ala Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Glu Ser Trp Gly Thr
                85              90              95

Tyr Arg Pro Thr Gly Thr Tyr Lys Gly Thr Val Thr Thr Asp Gly Gly
                100             105             110

Thr Tyr Asp Ile Tyr Glu Thr Trp Arg Tyr Asn Ala Pro Ser Ile Glu
                115             120             125

Gly Thr Arg Thr Phe Gln Gln Phe Trp Ser Val Arg Gln Gln Lys Arg
        130             135             140

Thr Ser Gly Thr Ile Thr Ile Gly Asn His Phe Asp Ala Trp Ala Arg
145             150             155             160

Ala Gly Met Asn Leu Gly Ser His Asp Tyr Gln Ile Met Ala Thr Glu
                165             170             175

Gly Tyr Gln Ser Ser Gly Ser Ser Thr Val Ser Ile Ser Glu Gly Gly
                180             185             190

Asn Pro Gly Asn Pro Gly Asn Pro Gly Asn Pro Gly Asn Pro Gly Asn
                195             200             205

Pro Gly Asn Pro Gly Gly Gly Cys Val Ala Thr Leu
```

```
        210             215             220

<210> SEQ ID NO 30
<211> LENGTH: 194
<212> TYPE: PRT
<213> ORGANISM: Herbidospora sp. NEAU-GS84

<400> SEQUENCE: 30

Gln Ala Ala Val Thr Thr Asn Gln Thr Gly Thr Asn Asn Gly Tyr Trp
1               5                   10                  15

Tyr Ser Phe Trp Thr Asp Ala Gln Gly Thr Val Ser Met Glu Leu Gly
                20                  25                  30

Ser Gly Gly Asn Tyr Ser Thr Ser Trp Arg Asn Thr Gly Asn Phe Val
            35                  40                  45

Ala Gly Lys Gly Trp Gln Thr Gly Gly Arg Arg Thr Val Ser Tyr Ser
        50                  55                  60

Gly Ser Phe Asn Pro Ser Gly Asn Ala Tyr Leu Thr Leu Tyr Gly Trp
65                  70                  75                  80

Thr Arg Asn Pro Leu Ile Glu Tyr Tyr Ile Val Asp Asn Trp Gly Thr
                85                  90                  95

Tyr Arg Pro Thr Gly Ser Phe Lys Gly Thr Val Thr Ser Asp Gly Gly
                100                 105                 110

Thr Tyr Asp Ile Tyr Glu Thr Thr Arg Thr Asn Ala Pro Ser Ile Glu
                115                 120                 125

Gly Thr Arg Thr Phe Lys Gln Phe Trp Ser Val Arg Gln Gln Lys Lys
            130                 135                 140

Thr Gly Gly Thr Ile Thr Ala Gly Asn His Phe Asp Ala Trp Ser Arg
145                 150                 155                 160

Ala Gly Met Gln Leu Gly Asn His Asp Tyr Met Ile Met Ala Thr Glu
                165                 170                 175

Gly Tyr Gln Ser Ser Gly Ser Ser Asn Ile Thr Ile Gly Gly Gly Thr
                180                 185                 190

Asn Pro

<210> SEQ ID NO 31
<211> LENGTH: 194
<212> TYPE: PRT
<213> ORGANISM: Artificial Sequence
<220> FEATURE:
<223> OTHER INFORMATION: Variant of Herbidospora sp. NEAU-GS84

<400> SEQUENCE: 31

Gln Ala Cys Val Thr Thr Asn Gln Thr Gly Thr Asn Asn Gly Tyr Trp
1               5                   10                  15

Tyr Ser Phe Trp Thr Asp Ala Gln Gly Thr Val Ser Met Cys Leu Gly
                20                  25                  30

Ser Gly Gly Asn Tyr Ser Thr Ser Trp Arg Asn Thr Gly Asn Phe Val
            35                  40                  45

Ala Gly Lys Gly Trp Gln Thr Gly Gly Arg Arg Thr Val Ser Tyr Ser
        50                  55                  60

Gly Ser Phe Asn Pro Ser Gly Asn Ala Tyr Leu Thr Leu Tyr Gly Trp
65                  70                  75                  80

Thr Arg Asn Pro Leu Ile Glu Tyr Tyr Ile Val Asp Asn Trp Gly Thr
                85                  90                  95

Tyr Arg Pro Thr Gly Ser Phe Lys Gly Thr Val Thr Ser Asp Gly Gly
                100                 105                 110
```

-continued

```
Thr Tyr Asp Ile Tyr Glu Thr Thr Arg Thr Asn Ala Pro Ser Ile Glu
        115                 120                 125

Gly Thr Arg Thr Phe Lys Gln Phe Trp Ser Val Arg Gln Gln Lys Lys
    130                 135                 140

Thr Gly Gly Thr Ile Thr Ala Gly Asn His Phe Asp Ala Trp Ser Arg
145                 150                 155                 160

Ala Gly Met Gln Leu Gly Asn His Asp Tyr Met Ile Met Ala Thr Glu
                165                 170                 175

Gly Tyr Gln Ser Ser Gly Ser Ser Asn Ile Thr Ile Gly Gly Gly Thr
            180                 185                 190

Asn Pro

<210> SEQ ID NO 32
<211> LENGTH: 194
<212> TYPE: PRT
<213> ORGANISM: Artificial Sequence
<220> FEATURE:
<223> OTHER INFORMATION: Variant of Herbidospora sp. NEAU-GS84

<400> SEQUENCE: 32

Gln Ala Cys Val Thr Thr Asn Gln Thr Gly Thr Asn Asn Gly Tyr Trp
1               5                   10                  15

Tyr Ser Phe Trp Thr Asp Ser Gln Gly Thr Val Ile Met Cys Leu Gly
                20                  25                  30

Ser Gly Gly Asn Tyr Ser Thr Ser Trp Arg Asn Thr Gly Asn Phe Val
            35                  40                  45

Ala Gly Lys Gly Trp Gln Thr Gly Gly Arg Arg Thr Val Ser Tyr Ser
    50                  55                  60

Gly Ser Phe Asn Pro Ser Gly Asn Ala Tyr Leu Thr Leu Tyr Gly Trp
65                  70                  75                  80

Thr Arg Asn Pro Leu Ile Glu Tyr Tyr Ile Val Asp Asn Trp Gly Thr
                85                  90                  95

Tyr Arg Pro Thr Gly Ser Phe Lys Gly Thr Val Thr Ser Asp Gly Gly
                100                 105                 110

Thr Tyr Asp Ile Tyr Glu Thr Thr Arg Thr Asn Ala Pro Ser Ile Glu
        115                 120                 125

Gly Thr Arg Thr Phe Lys Gln Phe Trp Ser Val Arg Gln Gln Lys Lys
    130                 135                 140

Thr Gly Gly Thr Ile Thr Ala Gly Asn His Phe Asp Ala Trp Ser Arg
145                 150                 155                 160

Ala Gly Met Gln Leu Gly Asn His Asp Tyr Met Ile Met Ala Thr Glu
                165                 170                 175

Gly Tyr Gln Ser Ser Gly Ser Ser Asn Ile Thr Ile Gly Gly Gly Thr
            180                 185                 190

Asn Pro

<210> SEQ ID NO 33
<211> LENGTH: 191
<212> TYPE: PRT
<213> ORGANISM: Nocardiopsis

<400> SEQUENCE: 33

Ser Ala Ala Ile Thr Ser Asn Gln Thr Gly Thr His Asn Gly Tyr Phe
1               5                   10                  15

Tyr Ser Phe Trp Thr Asp Ser Pro Gly Thr Val Ser Met Glu Leu Gly
                20                  25                  30
```

-continued

Ser Gly Gly Asn Tyr Ser Thr Ser Trp Arg Asn Thr Gly Asn Phe Val
        35                  40                  45

Ala Gly Thr Gly Trp Ser Thr Gly Gly Arg Arg Ser Val Thr Tyr Ser
    50                  55                  60

Ala Ser Phe Asn Pro Ser Gly Asn Ser Tyr Leu Thr Leu Tyr Gly Trp
65                  70                  75                  80

Thr Arg Asn Pro Leu Val Glu Tyr Tyr Ile Val Asp Asn Trp Gly Thr
                85                  90                  95

Tyr Arg Pro Thr Gly Thr His Met Gly Thr Val Thr Thr Asp Gly Gly
            100                 105                 110

Thr Tyr Asp Ile Tyr Arg Thr Arg Arg Thr Asn Ala Pro Ser Ile Glu
            115                 120                 125

Gly Thr Arg Ser Phe Asp Gln Tyr Trp Ser Val Arg Gln Ser Arg Arg
        130                 135                 140

Ser Ser Gly Thr Ile Thr Ser Gly Asn His Phe Asp Ala Trp Ala Arg
145                 150                 155                 160

Ala Gly Met Asn Leu Gly Ser His Asp Tyr Met Ile Met Ala Thr Glu
                165                 170                 175

Gly Tyr Gln Ser Ser Gly Ser Ser Asn Val Thr Leu Gly Ser Ser
            180                 185                 190

<210> SEQ ID NO 34
<211> LENGTH: 191
<212> TYPE: PRT
<213> ORGANISM: Artificial Sequence
<220> FEATURE:
<223> OTHER INFORMATION: Variant of Nocardiopsis, unclassified

<400> SEQUENCE: 34

Ser Ala Cys Ile Thr Ser Asn Gln Thr Gly Thr His Asn Gly Tyr Phe
1               5                   10                  15

Tyr Ser Phe Trp Thr Asp Ser Pro Gly Thr Val Ser Met Cys Leu Gly
            20                  25                  30

Ser Gly Gly Asn Tyr Ser Thr Ser Trp Arg Asn Thr Gly Asn Phe Val
        35                  40                  45

Ala Gly Thr Gly Trp Ser Thr Gly Gly Arg Arg Ser Val Thr Tyr Ser
    50                  55                  60

Ala Ser Phe Asn Pro Ser Gly Asn Ser Tyr Leu Thr Leu Tyr Gly Trp
65                  70                  75                  80

Thr Arg Asn Pro Leu Val Glu Tyr Tyr Ile Val Asp Asn Trp Gly Thr
                85                  90                  95

Tyr Arg Pro Thr Gly Thr His Met Gly Thr Val Thr Thr Asp Gly Gly
            100                 105                 110

Thr Tyr Asp Ile Tyr Arg Thr Arg Arg Thr Asn Ala Pro Ser Ile Glu
            115                 120                 125

Gly Thr Arg Ser Phe Asp Gln Tyr Trp Ser Val Arg Gln Ser Arg Arg
        130                 135                 140

Ser Ser Gly Thr Ile Thr Ser Gly Asn His Phe Asp Ala Trp Ala Arg
145                 150                 155                 160

Ala Gly Met Asn Leu Gly Ser His Asp Tyr Met Ile Met Ala Thr Glu
                165                 170                 175

Gly Tyr Gln Ser Ser Gly Ser Ser Asn Val Thr Leu Gly Ser Ser
            180                 185                 190

<210> SEQ ID NO 35
<211> LENGTH: 191

```
<212> TYPE: PRT
<213> ORGANISM: Artificial Sequence
<220> FEATURE:
<223> OTHER INFORMATION: Variant of Nocardiopsis, unclassified

<400> SEQUENCE: 35

Ser Ala Cys Ile Thr Ser Asn Gln Thr Gly Thr His Asn Gly Tyr Phe
1               5                   10                  15

Tyr Ser Phe Trp Thr Asp Ser Pro Gly Thr Val Ile Met Cys Leu Gly
            20                  25                  30

Ser Gly Gly Asn Tyr Ser Thr Ser Trp Arg Asn Thr Gly Asn Phe Val
        35                  40                  45

Ala Gly Thr Gly Trp Ser Thr Gly Gly Arg Arg Ser Val Thr Tyr Ser
    50                  55                  60

Ala Ser Phe Asn Pro Ser Gly Asn Ser Tyr Leu Thr Leu Tyr Gly Trp
65                  70                  75                  80

Thr Arg Asn Pro Leu Val Glu Tyr Tyr Ile Val Asp Asn Trp Gly Thr
                85                  90                  95

Tyr Arg Pro Thr Gly Thr His Met Gly Thr Val Thr Thr Asp Gly Gly
            100                 105                 110

Thr Tyr Asp Ile Tyr Arg Thr Arg Arg Thr Asn Ala Pro Ser Ile Glu
        115                 120                 125

Gly Thr Arg Ser Phe Asp Gln Tyr Trp Ser Val Arg Gln Ser Arg Arg
    130                 135                 140

Ser Ser Gly Thr Ile Thr Ser Gly Asn His Phe Asp Ala Trp Ala Arg
145                 150                 155                 160

Ala Gly Met Asn Leu Gly Ser His Asp Tyr Met Ile Met Ala Thr Glu
                165                 170                 175

Gly Tyr Gln Ser Ser Gly Ser Ser Asn Val Thr Leu Gly Ser Ser
            180                 185                 190

<210> SEQ ID NO 36
<211> LENGTH: 195
<212> TYPE: PRT
<213> ORGANISM: Nonomuraea longispora

<400> SEQUENCE: 36

Asn Ala Ala Ile Thr Ser Asn Gln Thr Gly Thr Asn Asn Gly Tyr Phe
1               5                   10                  15

Tyr Ser Phe Trp Thr Asp Ala Pro Gly Thr Val Ser Met Glu Leu Gly
            20                  25                  30

Ser Gly Gly Asn Tyr Ser Thr Ser Trp Arg Asn Thr Gly Asn Phe Val
        35                  40                  45

Ala Gly Lys Gly Trp Ser Thr Gly Gly Arg Arg Thr Val Ser Tyr Ser
    50                  55                  60

Gly Ser Phe Asn Pro Ser Gly Asn Ala Tyr Leu Thr Leu Tyr Gly Trp
65                  70                  75                  80

Thr Arg Asn Pro Leu Ile Glu Tyr Tyr Ile Val Asp Asn Trp Gly Thr
                85                  90                  95

Tyr Arg Pro Thr Gly Glu Tyr Arg Gly Thr Val Thr Ser Asp Gly Gly
            100                 105                 110

Thr Tyr Asp Ile Tyr Lys Thr Thr Arg Tyr Asp Ala Pro Ser Ile Glu
        115                 120                 125

Gly Thr Arg Thr Phe Asp Gln Tyr Trp Ser Val Arg Gln Ser Lys Arg
    130                 135                 140

Thr Gly Gly Ser Ile Thr Ser Gly Asn His Phe Asp Ala Trp Ala Arg
```

-continued

```
145                150                155                160

Gln Gly Met Asn Leu Gly Asn His Asp Tyr Met Ile Leu Ala Thr Glu
                165                170                175

Gly Tyr Gln Ser Ser Gly Asn Ser Asn Ile Thr Ile Gly Ser Gly Gly
            180                185                190

Gly Asn Pro
        195

<210> SEQ ID NO 37
<211> LENGTH: 195
<212> TYPE: PRT
<213> ORGANISM: Artificial Sequence
<220> FEATURE:
<223> OTHER INFORMATION: Variant of Nonomuraea longispora

<400> SEQUENCE: 37

Asn Ala Cys Ile Thr Ser Asn Gln Thr Gly Thr Asn Asn Gly Tyr Phe
1               5                10                15

Tyr Ser Phe Trp Thr Asp Ala Pro Gly Thr Val Ser Met Cys Leu Gly
                20                25                30

Ser Gly Gly Asn Tyr Ser Thr Ser Trp Arg Asn Thr Gly Asn Phe Val
            35                40                45

Ala Gly Lys Gly Trp Ser Thr Gly Gly Arg Arg Thr Val Ser Tyr Ser
        50                55                60

Gly Ser Phe Asn Pro Ser Gly Asn Ala Tyr Leu Thr Leu Tyr Gly Trp
65                70                75                80

Thr Arg Asn Pro Leu Ile Glu Tyr Tyr Ile Val Asp Asn Trp Gly Thr
                85                90                95

Tyr Arg Pro Thr Gly Glu Tyr Arg Gly Thr Val Thr Ser Asp Gly Gly
                100                105                110

Thr Tyr Asp Ile Tyr Lys Thr Thr Arg Tyr Asp Ala Pro Ser Ile Glu
            115                120                125

Gly Thr Arg Thr Phe Asp Gln Tyr Trp Ser Val Arg Gln Ser Lys Arg
            130                135                140

Thr Gly Gly Ser Ile Thr Ser Gly Asn His Phe Asp Ala Trp Ala Arg
145                150                155                160

Gln Gly Met Asn Leu Gly Asn His Asp Tyr Met Ile Leu Ala Thr Glu
                165                170                175

Gly Tyr Gln Ser Ser Gly Asn Ser Asn Ile Thr Ile Gly Ser Gly Gly
            180                185                190

Gly Asn Pro
        195

<210> SEQ ID NO 38
<211> LENGTH: 195
<212> TYPE: PRT
<213> ORGANISM: Artificial Sequence
<220> FEATURE:
<223> OTHER INFORMATION: Variant of Nonomuraea longispora

<400> SEQUENCE: 38

Asn Ala Cys Ile Thr Ser Asn Gln Thr Gly Thr Asn Asn Gly Tyr Phe
1               5                10                15

Tyr Ser Phe Trp Thr Asp Ser Pro Gly Thr Val Ile Met Cys Leu Gly
                20                25                30

Ser Gly Gly Asn Tyr Ser Thr Ser Trp Arg Asn Thr Gly Asn Phe Val
            35                40                45
```

```
Ala Gly Lys Gly Trp Ser Thr Gly Gly Arg Arg Thr Val Ser Tyr Ser
    50                  55                  60

Gly Ser Phe Asn Pro Ser Gly Asn Ala Tyr Leu Thr Leu Tyr Gly Trp
65                  70                  75                  80

Thr Arg Asn Pro Leu Ile Glu Tyr Tyr Ile Val Asp Asn Trp Gly Thr
                85                  90                  95

Tyr Arg Pro Thr Gly Glu Tyr Arg Gly Thr Val Thr Ser Asp Gly Gly
            100                 105                 110

Thr Tyr Asp Ile Tyr Lys Thr Thr Arg Tyr Asp Ala Pro Ser Ile Glu
            115                 120                 125

Gly Thr Arg Thr Phe Asp Gln Tyr Trp Ser Val Arg Gln Ser Lys Arg
    130                 135                 140

Thr Gly Gly Ser Ile Thr Ser Gly Asn His Phe Asp Ala Trp Ala Arg
145                 150                 155                 160

Gln Gly Met Asn Leu Gly Asn His Asp Tyr Met Ile Leu Ala Thr Glu
                165                 170                 175

Gly Tyr Gln Ser Ser Gly Asn Ser Asn Ile Thr Ile Gly Ser Gly Gly
            180                 185                 190

Gly Asn Pro
        195
```

```
<210> SEQ ID NO 39
<211> LENGTH: 191
<212> TYPE: PRT
<213> ORGANISM: Streptomyces sp. NRRL B-1140

<400> SEQUENCE: 39
```

```
Asp Thr Val Val Thr Ser Asn Gln Thr Gly Thr Asn Asn Gly Tyr Tyr
1               5                   10                  15

Tyr Ser Phe Trp Thr Asp Ala Pro Gly Thr Val Ser Met Thr Leu Ser
                20                  25                  30

Ser Gly Gly Ser Tyr Ser Thr Ser Trp Arg Asn Thr Gly Asn Phe Val
            35                  40                  45

Ala Gly Lys Gly Trp Ser Asn Gly Ala Arg Arg Thr Val Thr Tyr Ser
    50                  55                  60

Gly Ser Phe Asn Pro Ser Gly Asn Ala Tyr Leu Thr Leu Tyr Gly Trp
65                  70                  75                  80

Thr Ala Asn Pro Leu Val Glu Tyr Tyr Ile Val Asp Asn Trp Gly Thr
                85                  90                  95

Tyr Arg Pro Thr Gly Thr Tyr Lys Gly Thr Val Thr Ser Asp Gly Gly
            100                 105                 110

Thr Tyr Asp Ile Tyr Lys Thr Thr Arg Tyr Asn Ala Pro Ser Val Glu
            115                 120                 125

Gly Val Arg Thr Phe Asp Gln Tyr Trp Ser Val Arg Gln Ser Arg Arg
    130                 135                 140

Thr Gly Gly Thr Ile Thr Ala Gly Asn His Phe Asp Ala Trp Ala Arg
145                 150                 155                 160

Ala Gly Met Pro Leu Gly Asn Phe Lys Tyr Tyr Met Ile Met Ala Thr
                165                 170                 175

Glu Gly Tyr Arg Ser Ser Gly Asn Ser Ser Ile Arg Val Gly Ser
            180                 185                 190
```

```
<210> SEQ ID NO 40
<211> LENGTH: 191
<212> TYPE: PRT
<213> ORGANISM: Artificial Sequence
```

```
<220> FEATURE:
<223> OTHER INFORMATION: Variant of Streptomyces sp. NRRL B-1140

<400> SEQUENCE: 40

Asp Thr Cys Val Thr Ser Asn Gln Thr Gly Thr Asn Asn Gly Tyr Tyr
1               5                   10                  15

Tyr Ser Phe Trp Thr Asp Ala Pro Gly Thr Val Ser Met Cys Leu Ser
                20                  25                  30

Ser Gly Gly Ser Tyr Ser Thr Ser Trp Arg Asn Thr Gly Asn Phe Val
            35                  40                  45

Ala Gly Lys Gly Trp Ser Asn Gly Ala Arg Arg Thr Val Thr Tyr Ser
        50                  55                  60

Gly Ser Phe Asn Pro Ser Gly Asn Ala Tyr Leu Thr Leu Tyr Gly Trp
65                  70                  75                  80

Thr Ala Asn Pro Leu Val Glu Tyr Tyr Ile Val Asp Asn Trp Gly Thr
                85                  90                  95

Tyr Arg Pro Thr Gly Thr Tyr Lys Gly Thr Val Thr Ser Asp Gly Gly
                100                 105                 110

Thr Tyr Asp Ile Tyr Lys Thr Thr Arg Tyr Asn Ala Pro Ser Val Glu
            115                 120                 125

Gly Val Arg Thr Phe Asp Gln Tyr Trp Ser Val Arg Gln Ser Arg Arg
        130                 135                 140

Thr Gly Gly Thr Ile Thr Ala Gly Asn His Phe Asp Ala Trp Ala Arg
145                 150                 155                 160

Ala Gly Met Pro Leu Gly Asn Phe Lys Tyr Tyr Met Ile Met Ala Thr
                165                 170                 175

Glu Gly Tyr Arg Ser Ser Gly Asn Ser Ser Ile Arg Val Gly Ser
                180                 185                 190

<210> SEQ ID NO 41
<211> LENGTH: 191
<212> TYPE: PRT
<213> ORGANISM: Artificial Sequence
<220> FEATURE:
<223> OTHER INFORMATION: Variant of Streptomyces sp. NRRL B-1140

<400> SEQUENCE: 41

Asp Thr Cys Val Thr Ser Asn Gln Thr Gly Thr Asn Asn Gly Tyr Tyr
1               5                   10                  15

Tyr Ser Phe Trp Thr Asp Ser Pro Gly Thr Val Ile Met Cys Leu Ser
                20                  25                  30

Ser Gly Gly Ser Tyr Ser Thr Ser Trp Arg Asn Thr Gly Asn Phe Val
            35                  40                  45

Ala Gly Lys Gly Trp Ser Asn Gly Ala Arg Arg Thr Val Thr Tyr Ser
        50                  55                  60

Gly Ser Phe Asn Pro Ser Gly Asn Ala Tyr Leu Thr Leu Tyr Gly Trp
65                  70                  75                  80

Thr Ala Asn Pro Leu Val Glu Tyr Tyr Ile Val Asp Asn Trp Gly Thr
                85                  90                  95

Tyr Arg Pro Thr Gly Thr Tyr Lys Gly Thr Val Thr Ser Asp Gly Gly
                100                 105                 110

Thr Tyr Asp Ile Tyr Lys Thr Thr Arg Tyr Asn Ala Pro Ser Val Glu
            115                 120                 125

Gly Val Arg Thr Phe Asp Gln Tyr Trp Ser Val Arg Gln Ser Arg Arg
        130                 135                 140

Thr Gly Gly Thr Ile Thr Ala Gly Asn His Phe Asp Ala Trp Ala Arg
```

-continued

```
145             150             155             160

Ala Gly Met Pro Leu Gly Asn Phe Lys Tyr Tyr Met Ile Met Ala Thr
            165             170             175

Glu Gly Tyr Arg Ser Ser Gly Asn Ser Ser Ile Arg Val Gly Ser
            180             185             190

<210> SEQ ID NO 42
<211> LENGTH: 194
<212> TYPE: PRT
<213> ORGANISM: Actinomadura amylolytica

<400> SEQUENCE: 42

Ala Ala Pro Val Thr Ser Asn Gln Thr Gly Thr His Asp Gly Tyr Phe
1               5               10              15

Tyr Ser Phe Trp Thr Asp Ala Pro Gly Thr Val Ser Met Glu Leu Gly
            20              25              30

Ser Gly Gly Asn Tyr Ser Thr Ser Trp Arg Asn Thr Gly Asn Phe Val
            35              40              45

Ala Gly Lys Gly Trp Ser Thr Gly Gly Arg Arg Thr Val Thr Tyr Ser
    50              55              60

Gly Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Asp Asn Trp Gly Thr
            85              90              95

Tyr Arg Pro Thr Gly Thr Tyr Lys Gly Thr Val Thr Ser Asp Gly Gly
            100             105             110

Thr Tyr Asp Ile Tyr Glu Thr Thr Arg Tyr Asn Ala Pro Ser Ile Glu
            115             120             125

Gly Thr Arg Thr Phe Lys Gln Tyr Trp Ser Val Arg Gln Ser Arg Arg
            130             135             140

Thr Gly Gly Thr Ile Thr Ser Gly Asn His Phe Asp Ala Trp Ala Arg
145             150             155             160

Tyr Gly Met Ser Leu Gly Ser His Asp Tyr Met Ile Met Ala Thr Glu
            165             170             175

Gly Tyr Gln Ser Ser Gly Ser Ser Asn Ile Thr Val Gly Gly Ser Ser
            180             185             190

Asn Pro

<210> SEQ ID NO 43
<211> LENGTH: 194
<212> TYPE: PRT
<213> ORGANISM: Artificial Sequence
<220> FEATURE:
<223> OTHER INFORMATION: Variant of Actinomadura amylolytica

<400> SEQUENCE: 43

Ala Ala Cys Val Thr Ser Asn Gln Thr Gly Thr His Asp Gly Tyr Phe
1               5               10              15

Tyr Ser Phe Trp Thr Asp Ala Pro Gly Thr Val Ser Met Cys Leu Gly
            20              25              30

Ser Gly Gly Asn Tyr Ser Thr Ser Trp Arg Asn Thr Gly Asn Phe Val
            35              40              45

Ala Gly Lys Gly Trp Ser Thr Gly Gly Arg Arg Thr Val Thr Tyr Ser
    50              55              60

Gly Ser Phe Asn Pro Ser Gly Asn Ala Tyr Leu Thr Leu Tyr Gly Trp
65              70              75              80
```

Thr Arg Asn Pro Leu Val Glu Tyr Tyr Ile Val Asp Asn Trp Gly Thr
                85               90               95

Tyr Arg Pro Thr Gly Thr Tyr Lys Gly Thr Val Thr Ser Asp Gly Gly
            100             105             110

Thr Tyr Asp Ile Tyr Glu Thr Thr Arg Tyr Asn Ala Pro Ser Ile Glu
        115             120             125

Gly Thr Arg Thr Phe Lys Gln Tyr Trp Ser Val Arg Gln Ser Arg Arg
    130             135             140

Thr Gly Gly Thr Ile Thr Ser Gly Asn His Phe Asp Ala Trp Ala Arg
145             150             155             160

Tyr Gly Met Ser Leu Gly Ser His Asp Tyr Met Ile Met Ala Thr Glu
            165             170             175

Gly Tyr Gln Ser Ser Gly Ser Ser Asn Ile Thr Val Gly Gly Ser Ser
            180             185             190

Asn Pro

<210> SEQ ID NO 44
<211> LENGTH: 194
<212> TYPE: PRT
<213> ORGANISM: Artificial Sequence
<220> FEATURE:
<223> OTHER INFORMATION: Variant of Actinomadura amylolytica

<400> SEQUENCE: 44

Ala Ala Cys Val Thr Ser Asn Gln Thr Gly Thr His Asp Gly Tyr Phe
1               5               10              15

Tyr Ser Phe Trp Thr Asp Ser Pro Gly Thr Val Ile Met Cys Leu Gly
            20              25              30

Ser Gly Gly Asn Tyr Ser Thr Ser Trp Arg Asn Thr Gly Asn Phe Val
        35              40              45

Ala Gly Lys Gly Trp Ser Thr Gly Gly Arg Arg Thr Val Thr Tyr Ser
    50              55              60

Gly Ser Phe Asn Pro Ser Gly Asn Ala Tyr Leu Thr Leu Tyr Gly Trp
65              70              75              80

Thr Arg Asn Pro Leu Val Glu Tyr Tyr Ile Val Asp Asn Trp Gly Thr
                85               90               95

Tyr Arg Pro Thr Gly Thr Tyr Lys Gly Thr Val Thr Ser Asp Gly Gly
            100             105             110

Thr Tyr Asp Ile Tyr Glu Thr Thr Arg Tyr Asn Ala Pro Ser Ile Glu
        115             120             125

Gly Thr Arg Thr Phe Lys Gln Tyr Trp Ser Val Arg Gln Ser Arg Arg
    130             135             140

Thr Gly Gly Thr Ile Thr Ser Gly Asn His Phe Asp Ala Trp Ala Arg
145             150             155             160

Tyr Gly Met Ser Leu Gly Ser His Asp Tyr Met Ile Met Ala Thr Glu
            165             170             175

Gly Tyr Gln Ser Ser Gly Ser Ser Asn Ile Thr Val Gly Gly Ser Ser
            180             185             190

Asn Pro

<210> SEQ ID NO 45
<211> LENGTH: 191
<212> TYPE: PRT
<213> ORGANISM: Thermopolyspora flexuosa

<400> SEQUENCE: 45

```
Asp Thr Thr Ile Thr Gln Asn Gln Thr Gly Tyr Asp Asn Gly Tyr Phe
1               5                   10                  15

Tyr Ser Phe Arg Thr Asp Ala Pro Gly Thr Val Ser Met Thr Leu His
            20                  25                  30

Ser Gly Gly Ser Tyr Ser Thr Ser Trp Arg Asn Thr Gly Leu Phe Leu
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Arg Leu Thr Leu Tyr Gly Trp
65                  70                  75                  80

Thr Arg Asn Pro Leu Val Ser Tyr His Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Tyr Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
            165                 170                 175

Gly Tyr Gln Ser Ser Gly Ser Ser Thr Val Ser Ile Ser Glu Gly
            180                 185                 190
```

```
<210> SEQ ID NO 46
<211> LENGTH: 191
<212> TYPE: PRT
<213> ORGANISM: Artificial Sequence
<220> FEATURE:
<223> OTHER INFORMATION: Variant of Thermopolyspora flexuosa

<400> SEQUENCE: 46
```

```
Asp Thr Cys Ile Thr Gln Asn Gln Thr Gly Tyr Asp Asn Gly Tyr Phe
1               5                   10                  15

Tyr Ser Phe Arg Thr Asp Ala Pro Gly Thr Val Ser Met Cys Leu His
            20                  25                  30

Ser Gly Gly Ser Tyr Ser Thr Ser Trp Arg Asn Thr Gly Leu Phe Leu
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Arg Leu Thr Leu Tyr Gly Trp
65                  70                  75                  80

Thr Arg Asn Pro Leu Val Ser Tyr His Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Tyr Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
            165                 170                 175
```

```
Gly Tyr Gln Ser Ser Gly Ser Ser Thr Val Ser Ile Ser Glu Gly
        180             185             190
```

<210> SEQ ID NO 47
<211> LENGTH: 191
<212> TYPE: PRT
<213> ORGANISM: Artificial Sequence
<220> FEATURE:
<223> OTHER INFORMATION: Variant of Thermopolyspora flexuosa

<400> SEQUENCE: 47

```
Asp Thr Cys Ile Thr Gln Asn Gln Thr Gly Tyr Asp Asn Gly Tyr Phe
1               5               10              15

Tyr Ser Phe Arg Thr Asp Ser Pro Gly Thr Val Ile Met Cys Leu His
            20              25              30

Ser Gly Gly Ser Tyr Ser Thr Ser Trp Arg Asn Thr Gly Leu Phe Leu
        35              40              45

Ala Gly Lys Gly Trp Ser Thr Gly Gly Arg Arg Thr Val Thr Tyr Asn
    50              55              60

Ala Ser Phe Asn Pro Ser Gly Asn Ala Arg Leu Thr Leu Tyr Gly Trp
65              70              75              80

Thr Arg Asn Pro Leu Val Ser Tyr His Ile Val Glu Ser Trp Gly Thr
                85              90              95

Tyr Arg Pro Thr Gly Thr Tyr Lys Gly Thr Val Thr Thr Asp Gly Gly
            100             105             110

Thr Tyr Asp Ile Tyr Glu Thr Trp Arg Tyr Asn Ala Pro Ser Ile Glu
        115             120             125

Gly Thr Arg Thr Tyr Gln Gln Phe Trp Ser Val Arg Gln Gln Lys Arg
    130             135             140

Thr Ser Gly Thr Ile Thr Ile Gly Asn His Phe Asp Ala Trp Ala Arg
145             150             155             160

Ala Gly Met Asn Leu Gly Ser His Asp Tyr Gln Ile Met Ala Thr Glu
            165             170             175

Gly Tyr Gln Ser Ser Gly Ser Ser Thr Val Ser Ile Ser Glu Gly
        180             185             190
```

<210> SEQ ID NO 48
<211> LENGTH: 663
<212> TYPE: DNA
<213> ORGANISM: Artificial Sequence
<220> FEATURE:
<223> OTHER INFORMATION: AM24

<400> SEQUENCE: 48

```
gacaccacca tcacccagaa ccagaccggc tacgacaacg gctacttcta ctcgttctgg      60
accgacgccc ccggcaccgt ctccatgacc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
```

-continued

```
ggcaaccccg gcaaccccgg taacccgggt aaccccggcg gtggctgcgt cgcgaccctc      660
taa                                                                    663

<210> SEQ ID NO 49
<211> LENGTH: 663
<212> TYPE: DNA
<213> ORGANISM: Artificial Sequence
<220> FEATURE:
<223> OTHER INFORMATION: variant

<400> SEQUENCE: 49
gacacctgca tcacccagaa ccagaccggc tacgacaacg gctacttcta ctcgttctgg       60
accgactccc ccggcaccgt catcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgcgaccctc      660
taa                                                                    663

<210> SEQ ID NO 50
<211> LENGTH: 663
<212> TYPE: DNA
<213> ORGANISM: Artificial Sequence
<220> FEATURE:
<223> OTHER INFORMATION: variant

<400> SEQUENCE: 50
gacacctgca tcacccagaa ccagaccggc tacgacaacg gctacttcta ctcgttctgg       60
accgacgcgc ccggcaccgt ctccatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgcgaccctc      660
taa                                                                    663

<210> SEQ ID NO 51
<211> LENGTH: 663
<212> TYPE: DNA
<213> ORGANISM: Artificial Sequence
<220> FEATURE:
<223> OTHER INFORMATION: variant
```

<400> SEQUENCE: 51
gacacctgca tcacccagaa ccagaccggc tacgacaacg gctacttcta ctcgttctgg      60
accgactccc ccggcaccgt ctccatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagc ggggcaccta ccggcccacc      300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
taa                                                                   663

<210> SEQ ID NO 52
<211> LENGTH: 663
<212> TYPE: DNA
<213> ORGANISM: Artificial Sequence
<220> FEATURE:
<223> OTHER INFORMATION: variant

<400> SEQUENCE: 52
gacacctgca tcacccagaa ccagaccggc tacgacaacg gctacttcta ctcgttctgg      60
accgacgcgc ccggcaccgt catcatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagc ggggcaccta ccggcccacc      300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
taa                                                                   663

<210> SEQ ID NO 53
<211> LENGTH: 663
<212> TYPE: DNA
<213> ORGANISM: Artificial Sequence
<220> FEATURE:
<223> OTHER INFORMATION: variant

<400> SEQUENCE: 53
gacaccacca tcacccagaa ccagaccggc tacgacaacg gctacttcta ctcgttctgg      60
accgactccc ccggcaccgt ctccatgacc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240

```
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
taa                                                                    663

<210> SEQ ID NO 54
<211> LENGTH: 663
<212> TYPE: DNA
<213> ORGANISM: Artificial Sequence
<220> FEATURE:
<223> OTHER INFORMATION: variant

<400> SEQUENCE: 54
gacaccacca tcacccagaa ccagaccggc tacgacaacg gctacttcta ctcgttctgg      60
accgacgcgc ccggcaccgt catcatgacc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
taa                                                                    663

<210> SEQ ID NO 55
<211> LENGTH: 663
<212> TYPE: DNA
<213> ORGANISM: Artificial Sequence
<220> FEATURE:
<223> OTHER INFORMATION: variant

<400> SEQUENCE: 55
gacaccacca tcacccagaa ccagaccggc tacgacaacg gctacttcta ctcgttctgg      60
accgactccc ccggcaccgt catcatgacc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
```

```
ggcaaccccg gcaaccccgg taacccgggt aaccccggcg gtggctgcgt cgcgaccctc      660
taa                                                                       663

<210> SEQ ID NO 56
<211> LENGTH: 663
<212> TYPE: DNA
<213> ORGANISM: Artificial Sequence
<220> FEATURE:
<223> OTHER INFORMATION: variant

<400> SEQUENCE: 56
gacaccacca tcacccagaa ccagaccggg tacgacaacg gctacttcta ctcgttctgg       60
accgacgcgc ccgggaccgt ctccatgacc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                       663

<210> SEQ ID NO 57
<211> LENGTH: 663
<212> TYPE: DNA
<213> ORGANISM: Artificial Sequence
<220> FEATURE:
<223> OTHER INFORMATION: variant

<400> SEQUENCE: 57
gacacctgca tcacccagaa ccagaccggg tacgacaacg gctacttcta ctcgttctgg       60
accgactccc ccgggaccgt catcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                       663

<210> SEQ ID NO 58
<211> LENGTH: 663
<212> TYPE: DNA
<213> ORGANISM: Artificial Sequence
<220> FEATURE:
```

<223> OTHER INFORMATION: variant

<400> SEQUENCE: 58
gacacctgca tcacccagaa ccagaccggg tacgacaacg gctacttcta ctcgttctgg      60
accgactacc ccgggaccgt catcatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgccaccctc     660
taa                                                                    663

<210> SEQ ID NO 59
<211> LENGTH: 663
<212> TYPE: DNA
<213> ORGANISM: Artificial Sequence
<220> FEATURE:
<223> OTHER INFORMATION: variant

<400> SEQUENCE: 59
gacacctgca tcacccagaa ccagaccggg tacgacaacg gctacttcta ctcgttctgg      60
accgaccacc ccgggaccgt catcatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgccaccctc     660
taa                                                                    663

<210> SEQ ID NO 60
<211> LENGTH: 663
<212> TYPE: DNA
<213> ORGANISM: Artificial Sequence
<220> FEATURE:
<223> OTHER INFORMATION: variant

<400> SEQUENCE: 60
gacacctgca tcacccagaa ccagaccggg tacgacaacg gctacttcta ctcgttctgg      60
accgacaccc ccgggaccgt catcatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240

```
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 61
<211> LENGTH: 663
<212> TYPE: DNA
<213> ORGANISM: Artificial Sequence
<220> FEATURE:
<223> OTHER INFORMATION: variant

<400> SEQUENCE: 61
```

```
gacacctgca tcacccagaa ccagaccggg tacgacaacg gctacttcta ctcgttctgg       60
accgacatgc ccgggaccgt catcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 62
<211> LENGTH: 663
<212> TYPE: DNA
<213> ORGANISM: Artificial Sequence
<220> FEATURE:
<223> OTHER INFORMATION: variant

<400> SEQUENCE: 62
```

```
gacacctgca tcacccagaa ccagaccggg tacgacaacg gctacttcta ctcgttctgg       60
accgaccgcc ccgggaccgt catcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
```

```
agcggtagct ccaccgtctc catcagcgag ggtggcaacc ccggcaaccc gggtaacccc      600
ggcaaccccg gcaaccccgg taacccgggt aacccggcg gtggctgcgt cgccaccctc      660
taa                                                                    663
```

```
<210> SEQ ID NO 63
<211> LENGTH: 663
<212> TYPE: DNA
<213> ORGANISM: Artificial Sequence
<220> FEATURE:
<223> OTHER INFORMATION: variant

<400> SEQUENCE: 63
gacacctgca tcacccagaa ccagaccggg tacgacaacg gctacttcta ctcgttctgg       60
accgactccc ccgggaccgt cctcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aacccggcg gtggctgcgt cgccaccctc      660
taa                                                                    663
```

```
<210> SEQ ID NO 64
<211> LENGTH: 663
<212> TYPE: DNA
<213> ORGANISM: Artificial Sequence
<220> FEATURE:
<223> OTHER INFORMATION: variant

<400> SEQUENCE: 64
gacacctgca tcacccagaa ccagaccggg tacgacaacg gctacttcta ctcgttctgg       60
accgactccc ccgggaccgt ccgcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aacccggcg gtggctgcgt cgccaccctc      660
taa                                                                    663
```

```
<210> SEQ ID NO 65
<211> LENGTH: 663
<212> TYPE: DNA
<213> ORGANISM: Artificial Sequence
```

-continued

```
<220> FEATURE:
<223> OTHER INFORMATION: variant

<400> SEQUENCE: 65
gacacctgca tcacccagaa ccagaccggg tacgacaacg gctacttcta ctcgttctgg      60
accgactccc ccgggaccgt catgatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgccaccctc     660
taa                                                                   663

<210> SEQ ID NO 66
<211> LENGTH: 663
<212> TYPE: DNA
<213> ORGANISM: Artificial Sequence
<220> FEATURE:
<223> OTHER INFORMATION: variant

<400> SEQUENCE: 66
gacacctgca tcacccagaa ccagaccggg tacgacaacg gctacttcta ctcgttctgg      60
accgactccc ccgggaccgt ccagatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgccaccctc     660
taa                                                                   663

<210> SEQ ID NO 67
<211> LENGTH: 663
<212> TYPE: DNA
<213> ORGANISM: Artificial Sequence
<220> FEATURE:
<223> OTHER INFORMATION: variant

<400> SEQUENCE: 67
gacacctgca tcacccagaa ccagaccggg tacgacaacg gctacttcta ctcgttctgg      60
accgactccc ccgggaccgt ctacatgtgc ctccactcgg gcggcagcta cagcacctcg     120
tggcgcaaca ccggcaactt cgtcgccggc aagggctggt ccaccggcgg ccgccgcacc     180
```

-continued

```
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                     663
```

<210> SEQ ID NO 68
<211> LENGTH: 663
<212> TYPE: DNA
<213> ORGANISM: Artificial Sequence
<220> FEATURE:
<223> OTHER INFORMATION: variant

<400> SEQUENCE: 68

```
gacacctgca tcacccagaa ccagaccggg tacgacaacg gctacttcta ctcgttctgg       60
accgactccc ccgggaccgt ctggatgtgc ctccactcgg gcggcagcta cagcaccctcg     120 tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                     663
```

<210> SEQ ID NO 69
<211> LENGTH: 663
<212> TYPE: DNA
<213> ORGANISM: Artificial Sequence
<220> FEATURE:
<223> OTHER INFORMATION: variant

<400> SEQUENCE: 69

```
gacacctgca tcacccagaa ccagaccggg tacgacaacg gctacttcta ctcgttctgg       60
accgactccc ccgggaccgt caccatgtgc ctccactcgg gcggcagcta cagcaccctcg     120 tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
```

```
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663

<210> SEQ ID NO 70
<211> LENGTH: 663
<212> TYPE: DNA
<213> ORGANISM: Artificial Sequence
<220> FEATURE:
<223> OTHER INFORMATION: variant

<400> SEQUENCE: 70
gacacctgca tcacccagaa ccagaccggg tacgacaacg gctacttcta ctcgttctgg       60
accgactccc ccgggaccgt caacatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgc acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663

<210> SEQ ID NO 71
<211> LENGTH: 663
<212> TYPE: DNA
<213> ORGANISM: Artificial Sequence
<220> FEATURE:
<223> OTHER INFORMATION: variant

<400> SEQUENCE: 71
gacacctgca tcacccagaa ccagaccggg tacgacaacg gctacttcta ctcgttctgg       60
accgactccc ccgggaccgt cgtcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgc acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663

<210> SEQ ID NO 72
<211> LENGTH: 663
<212> TYPE: DNA
```

```
<213> ORGANISM: Artificial Sequence
<220> FEATURE:
<223> OTHER INFORMATION: variant

<400> SEQUENCE: 72
gacacctgca tcacccagaa ccagaccggg tacgacaacg gctacttcta ctcgttctgg      60
accgaccgcc ccgggaccgt cctcatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgccaccctc     660
taa                                                                    663

<210> SEQ ID NO 73
<211> LENGTH: 663
<212> TYPE: DNA
<213> ORGANISM: Artificial Sequence
<220> FEATURE:
<223> OTHER INFORMATION: variant

<400> SEQUENCE: 73
gacacctgca tcacccagaa ccagaccggg tacgacaacg gctacttcta ctcgttctgg      60
accgaccgcc ccgggaccgt ccagatgtgc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgccaccctc     660
taa                                                                    663

<210> SEQ ID NO 74
<211> LENGTH: 663
<212> TYPE: DNA
<213> ORGANISM: Artificial Sequence
<220> FEATURE:
<223> OTHER INFORMATION: variant

<400> SEQUENCE: 74
gacacctgca tcacccagaa ccagaccggg tacgacaacg gctacttcta ctcgttctgg      60
accgaccacc ccgggaccgt cctcatgtgc ctccactcgg gcggcagcta cagcacctcg     120
tggcgcaaca ccggcaactt cgtcgccggc aagggctggt ccaccggcgg ccgccgcacc     180
```

-continued

```
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 75
<211> LENGTH: 663
<212> TYPE: DNA
<213> ORGANISM: Artificial Sequence
<220> FEATURE:
<223> OTHER INFORMATION: variant

<400> SEQUENCE: 75
```

```
gacacctgca tcacccagaa ccagaccggg tacgacaacg gctacttcta ctcgttctgg       60
accgacaccc ccgggaccgt cctcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 76
<211> LENGTH: 663
<212> TYPE: DNA
<213> ORGANISM: Artificial Sequence
<220> FEATURE:
<223> OTHER INFORMATION: variant

<400> SEQUENCE: 76
```

```
gacacctgca tcacccagaa ccagaccggg tacgacaacg gctacttcta ctcgttctgg       60
accgactggc ccgggaccgt catcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
```

-continued

```
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 77
<211> LENGTH: 663
<212> TYPE: DNA
<213> ORGANISM: Artificial Sequence
<220> FEATURE:
<223> OTHER INFORMATION: variant

<400> SEQUENCE: 77
gacacctgca tcacccagaa ccagaccggg tacgacaacg gctacttcta ctcgttctgg       60 accgacccccc ccgggaccgt catcatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 78
<211> LENGTH: 663
<212> TYPE: DNA
<213> ORGANISM: Artificial Sequence
<220> FEATURE:
<223> OTHER INFORMATION: variant

<400> SEQUENCE: 78
gacacctgca tcacccagaa ccagaccggg tacgacaacg gctacttcta ctcgttctgg       60
accgactccc ccgggaccgt ccccatgtgc ctccactcgg gcggcagcta cagcacctcg      120
tggcgcaaca ccggcaactt cgtcgccggc aagggctggt ccaccggcgg ccgccgcacc      180
gtcacctaca acgcctcctt caacccgtcg ggtaacgcct acctcacgct ctacggctgg      240
accaggaacc cgctcgtcga gtactacatc gtcgagagct ggggcaccta ccggcccacc      300
ggcacctaca agggcaccgt caccaccgac ggcggcacgt acgacatcta cgagacctgg      360
cggtacaacg cgccgtccat cgagggcacc cggaccttcc agcagttctg gagcgtccgg      420
cagcagaagc ggaccagcgg caccatcacc atcggcaacc acttcgacgc ctgggcccgc      480
gccggcatga acctgggcag ccacgactac cagatcatgg cgaccgaggg ctaccagagc      540
agcggtagct ccaccgtctc catcagcgag ggtggcaacc ccggcaaccc gggtaacccc      600
ggcaaccccg gcaaccccgg taacccgggt aaccccggcg gtggctgcgt cgccaccctc      660
taa                                                                    663
```

```
<210> SEQ ID NO 79
<211> LENGTH: 585
```

```
<212> TYPE: DNA
<213> ORGANISM: Herbidospora sp. NEAU-GS84

<400> SEQUENCE: 79
caggctgccg tcaccactaa ccagaccggc actaacaacg gctactggta cagcttctgg      60
accgacgccc agggcaccgt ctctatggag ctcggcagcg gcggcaacta cagcacctcg     120
tggcgcaaca ccggcaactt cgtcgctggc aagggctggc agactggcgg gcgccgcacg     180
gtctcttact cgggctcttt caaccccagc ggcaacgcct acctcactct gtacggctgg     240
acccgcaacc ctctcatcga gtactacatc gtcgacaact ggggcactta ccgccctacc     300
ggcagcttca agggcactgt caccagcgac ggcggcacct acgacatcta cgagaccact     360
cgcaccaacg cccttctat cgagggcact cgcaccttca agcagttctg gagcgtccgc      420
cagcagaaga agactggcgg caccatcact gccggcaacc acttcgacgc ctggtctcgc     480
gccggcatgc agctgggcaa ccacgactac atgatcatgg ccaccgaggg ctaccagagc     540
tctggctcca gcaacatcac catcggcggc ggcacgaacc cttaa                     585

<210> SEQ ID NO 80
<211> LENGTH: 585
<212> TYPE: DNA
<213> ORGANISM: Artificial Sequence
<220> FEATURE:
<223> OTHER INFORMATION: Variant of Herbidospora sp. NEAU-GS84

<400> SEQUENCE: 80
caggcttgcg tcaccactaa ccagaccggc actaacaacg gctactggta cagcttctgg      60
accgacgccc agggcaccgt ctctatgtgc ctcggcagcg gcggcaacta cagcacctcg     120
tggcgcaaca ccggcaactt cgtcgctggc aagggctggc agactggcgg gcgccgcacg     180
gtctcttact cgggctcttt caaccccagc ggcaacgcct acctcactct gtacggctgg     240
acccgcaacc ctctcatcga gtactacatc gtcgacaact ggggcactta ccgccctacc     300
ggcagcttca agggcactgt caccagcgac ggcggcacct acgacatcta cgagaccact     360
cgcaccaacg cccttctat cgagggcact cgcaccttca agcagttctg gagcgtccgc      420
cagcagaaga agactggcgg caccatcact gccggcaacc acttcgacgc ctggtctcgc     480
gccggcatgc agctgggcaa ccacgactac atgatcatgg ccaccgaggg ctaccagagc     540
tctggctcca gcaacatcac catcggcggc ggcacgaacc cttaa                     585

<210> SEQ ID NO 81
<211> LENGTH: 585
<212> TYPE: DNA
<213> ORGANISM: Artificial Sequence
<220> FEATURE:
<223> OTHER INFORMATION: Variant of Herbidospora sp. NEAU-GS84

<400> SEQUENCE: 81
caggcttgcg tcaccactaa ccagaccggc actaacaacg gctactggta cagcttctgg      60
accgacagcc agggcaccgt cattatgtgc ctcggcagcg gcggcaacta cagcacctcg     120
tggcgcaaca ccggcaactt cgtcgctggc aagggctggc agactggcgg gcgccgcacg     180
gtctcttact cgggctcttt caaccccagc ggcaacgcct acctcactct gtacggctgg     240
acccgcaacc ctctcatcga gtactacatc gtcgacaact ggggcactta ccgccctacc     300
ggcagcttca agggcactgt caccagcgac ggcggcacct acgacatcta cgagaccact     360
cgcaccaacg cccttctat cgagggcact cgcaccttca agcagttctg gagcgtccgc      420
```

```
cagcagaaga agactggcgg caccatcact gccggcaacc acttcgacgc ctggtctcgc          480
gccggcatgc agctgggcaa ccacgactac atgatcatgg ccaccgaggg ctaccagagc          540
tctggctcca gcaacatcac catcggcggc ggcacgaacc cttaa                          585

<210> SEQ ID NO 82
<211> LENGTH: 576
<212> TYPE: DNA
<213> ORGANISM: Nocardiopsis

<400> SEQUENCE: 82
tctgctgcca tcacctccaa ccagactggc acccacaacg gctacttcta cagcttctgg           60
actgacagcc ctggcaccgt cagcatggag ctcggcagcg gcggcaacta cagcacctct          120
tggcgcaaca ccggcaactt cgtcgctggc accggctgga gcaccggcgg cgcccgcagc          180
gtcacttact ccgccagctt taacccgtcg ggcaacagct acctgaccct ctacggctgg          240
acccgcaacc ctctggtcga gtactacatc gtcgacaact ggggcaccta ccgccctacc          300
ggcactcaca tgggcactgt cacgaccgac ggcggcacgt acgacatcta ccgcactcgc          360
cgcactaacg cccctagcat cgagggcact cgcagcttcg accagtactg gagcgtccgc          420
cagtctcgcc gcagctccgg caccatcact tcgggcaacc acttcgacgc ctgggctcgc          480
gccggcatga acctgggcag ccacgactac atgatcatgg ccactgaggg ctaccagagc          540
tctggctcga gcaacgtcac tctgggctcg tcctaa                                    576

<210> SEQ ID NO 83
<211> LENGTH: 576
<212> TYPE: DNA
<213> ORGANISM: Artificial Sequence
<220> FEATURE:
<223> OTHER INFORMATION: Varian of Nocardiopsis, unclassified

<400> SEQUENCE: 83
tctgcttgca tcacctccaa ccagactggc acccacaacg gctacttcta cagcttctgg           60
actgacagcc ctggcaccgt cagcatgtgc ctcggcagcg gcggcaacta cagcacctct          120
tggcgcaaca ccggcaactt cgtcgctggc accggctgga gcaccggcgg cgcccgcagc          180
gtcacttact ccgccagctt taacccgtcg ggcaacagct acctgaccct ctacggctgg          240
acccgcaacc ctctggtcga gtactacatc gtcgacaact ggggcaccta ccgccctacc          300
ggcactcaca tgggcactgt cacgaccgac ggcggcacgt acgacatcta ccgcactcgc          360
cgcactaacg cccctagcat cgagggcact cgcagcttcg accagtactg gagcgtccgc          420
cagtctcgcc gcagctccgg caccatcact tcgggcaacc acttcgacgc ctgggctcgc          480
gccggcatga acctgggcag ccacgactac atgatcatgg ccactgaggg ctaccagagc          540
tctggctcga gcaacgtcac tctgggctcg tcctaa                                    576

<210> SEQ ID NO 84
<211> LENGTH: 576
<212> TYPE: DNA
<213> ORGANISM: Artificial Sequence
<220> FEATURE:
<223> OTHER INFORMATION: Variant of Nocardiopsis, unclassified

<400> SEQUENCE: 84
tctgcttgca tcacctccaa ccagactggc acccacaacg gctacttcta cagcttctgg           60
actgacagcc ctggcaccgt cattatgtgc ctcggcagcg gcggcaacta cagcacctct          120
tggcgcaaca ccggcaactt cgtcgctggc accggctgga gcaccggcgg cgcccgcagc          180
```

-continued

```
gtcacttact ccgccagctt taacccgtcg ggcaacagct acctgaccct ctacggctgg      240
acccgcaacc ctctggtcga gtactacatc gtcgacaact ggggcaccta ccgccctacc      300
ggcactcaca tgggcactgt cacgaccgac ggcggcacgt acgacatcta ccgcactcgc      360
cgcactaacg ccctagcat cgagggcact cgcagcttcg accagtactg gagcgtccgc       420
cagtctcgcc gcagctccgg caccatcact tcgggcaacc acttcgacgc ctgggctcgc      480
gccggcatga acctgggcag ccacgactac atgatcatgg ccactgaggg ctaccagagc      540
tctggctcga gcaacgtcac tctgggctcg tcctaa                                 576
```

```
<210> SEQ ID NO 85
<211> LENGTH: 588
<212> TYPE: DNA
<213> ORGANISM: Nonomuraea longispora

<400> SEQUENCE: 85
aacgccgcca tcaccagcaa ccagaccggc acgaacaacg gctacttcta ctcgttctgg       60
acggacgctc ctggcaccgt ctccatggag ctcggcagcg gcggcaacta ctccaccagc      120
tggcgcaaca cgggcaactt cgtcgctggc aagggctggt ccaccggcgg ccgacgcacg      180
gtctcgtact ccggcagctt caaccccagc ggcaacgcct acctcaccct gtacggctgg      240
acgcgcaacc ctctgatcga gtactacatc gtcgacaact ggggcaccta ccgccctacc      300
ggcgagtatc gcggcacggt caccagcgac ggtggcacct acgacatcta caagaccacg      360
cgctacgacg ctcctagcat cgagggcacc cgcacgttcg accagtactg gtcggtccgc      420
cagagcaagc gcaccggcgg ctcgatcacc tcgggcaacc actttgacgc ttgggctcgc      480
cagggcatga acctgggcaa ccacgactac atgatcctgg ccaccgaggg ctaccagagc      540
agcggcaact cgaacatcac catcggcagc ggcggcggca acccttaa                   588
```

```
<210> SEQ ID NO 86
<211> LENGTH: 588
<212> TYPE: DNA
<213> ORGANISM: Artificial Sequence
<220> FEATURE:
<223> OTHER INFORMATION: Variant of Nonomuraea longispora

<400> SEQUENCE: 86
aacgcctgca tcaccagcaa ccagaccggc acgaacaacg gctacttcta ctcgttctgg       60
acggacgctc ctggcaccgt ctccatgtgc ctcggcagcg gcggcaacta ctccaccagc      120
tggcgcaaca cgggcaactt cgtcgctggc aagggctggt ccaccggcgg ccgacgcacg      180
gtctcgtact ccggcagctt caaccccagc ggcaacgcct acctcaccct gtacggctgg      240
acgcgcaacc ctctgatcga gtactacatc gtcgacaact ggggcaccta ccgccctacc      300
ggcgagtatc gcggcacggt caccagcgac ggtggcacct acgacatcta caagaccacg      360
cgctacgacg ctcctagcat cgagggcacc cgcacgttcg accagtactg gtcggtccgc      420
cagagcaagc gcaccggcgg ctcgatcacc tcgggcaacc actttgacgc ttgggctcgc      480
cagggcatga acctgggcaa ccacgactac atgatcctgg ccaccgaggg ctaccagagc      540
agcggcaact cgaacatcac catcggcagc ggcggcggca acccttaa                   588
```

```
<210> SEQ ID NO 87
<211> LENGTH: 588
<212> TYPE: DNA
<213> ORGANISM: Artificial Sequence
<220> FEATURE:
```

```
<223> OTHER INFORMATION: Variant of Nonomuraea longispora

<400> SEQUENCE: 87
aacgcctgta tcaccagcaa ccagaccggc acgaacaacg gctacttcta ctcgttctgg      60
acggactccc ctggcaccgt catcatgtgt ctcggcagcg gcggcaacta ctccaccagc     120
tggcgcaaca cgggcaactt cgtcgctggc aagggctggt ccaccggcgg ccgacgcacg     180
gtctcgtact ccggcagctt caaccccagc ggcaacgcct acctcaccct gtacggctgg     240
acgcgcaacc ctctgatcga gtactacatc gtcgacaact ggggcaccta ccgccctacc     300
ggcgagtatc gcggcacggt caccagcgac ggtggcacct acgacatcta caagaccacg     360
cgctacgacg ctcctagcat cgagggcacc cgcacgttcg accagtactg gtcggtccgc     420
cagagcaagc gcaccggcgg ctcgatcacc tcgggcaacc actttgacgc ttgggctcgc     480
cagggcatga acctgggcaa ccacgactac atgatcctgg ccaccgaggg ctaccagagc     540
agcggcaact cgaacatcac catcggcagc ggcggcggca acccttaa                 588

<210> SEQ ID NO 88
<211> LENGTH: 576
<212> TYPE: DNA
<213> ORGANISM: Streptomyces sp. NRRL B-1140

<400> SEQUENCE: 88
gacaccgtcg tcactagcaa ccagaccggc actaacaacg gctactacta cagcttttgg      60
accgacgccc ctggcaccgt cagcatgacc ctgagctctg gcggcagcta ctctaccagc     120
tggcgcaaca ccggcaactt cgtcgccggc aagggctggt ctaacggcgc ccgccgcacc     180
gtcacgtact ctggcagctt caaccctagc ggcaacgcct acctcaccct gtacggctgg     240
accgctaacc cctggtcga gtactacatc gtcgacaact ggggcactta ccgccccacc     300
ggcacgtaca agggcaccgt cacttctgac ggcggcacct acgacatcta caagaccacg     360
cgctacaacg ccctagcgt cgagggcgtc cgcacctttg accagtactg gagcgtccgc     420
cagagccgcc gcactggcgg caccatcact gccggcaacc acttcgacgc ctgggctcgc     480
gccggcatgc ctctgggcaa ctttaagtac tacatgatca tggccaccga gggctaccgc     540
tcgagcggca actcgtctat ccgcgtcggc tcctaa                             576

<210> SEQ ID NO 89
<211> LENGTH: 576
<212> TYPE: DNA
<213> ORGANISM: Artificial Sequence
<220> FEATURE:
<223> OTHER INFORMATION: Variant of Streptomyces sp. NRRL B-1140

<400> SEQUENCE: 89
gacacctgcg tcactagcaa ccagaccggc actaacaacg gctactacta cagcttttgg      60
accgacgccc ctggcaccgt cagcatgtgc ctgagctctg gcggcagcta ctctaccagc     120
tggcgcaaca ccggcaactt cgtcgccggc aagggctggt ctaacggcgc ccgccgcacc     180
gtcacgtact ctggcagctt caaccctagc ggcaacgcct acctcaccct gtacggctgg     240
accgctaacc cctggtcga gtactacatc gtcgacaact ggggcactta ccgccccacc     300
ggcacgtaca agggcaccgt cacttctgac ggcggcacct acgacatcta caagaccacg     360
cgctacaacg ccctagcgt cgagggcgtc cgcacctttg accagtactg gagcgtccgc     420
cagagccgcc gcactggcgg caccatcact gccggcaacc acttcgacgc ctgggctcgc     480
gccggcatgc ctctgggcaa ctttaagtac tacatgatca tggccaccga gggctaccgc     540
```

-continued

```
tcgagcggca actcgtctat ccgcgtcggc tcctaa                              576

<210> SEQ ID NO 90
<211> LENGTH: 576
<212> TYPE: DNA
<213> ORGANISM: Artificial Sequence
<220> FEATURE:
<223> OTHER INFORMATION: Variant of Streptomyces sp. NRRL B-1140

<400> SEQUENCE: 90
gacacctgcg tcactagcaa ccagaccggc actaacaacg gctactacta cagcttttgg      60
accgacagcc ctggcaccgt cattatgtgc ctgagctctg gcggcagcta ctctaccagc     120
tggcgcaaca ccggcaactt cgtcgccggc aagggctggt ctaacggcgc ccgccgcacc     180
gtcacgtact ctggcagctt caaccctagc ggcaacgcct acctcaccct gtacggctgg     240
accgctaacc ccctggtcga gtactacatc gtcgacaact ggggcactta ccgccccacc     300
ggcacgtaca agggcaccgt cacttctgac ggcggcacct acgacatcta caagaccacg     360
cgctacaacg ccctagcgt cgagggcgtc cgcacctttg accagtactg gagcgtccgc      420
cagagccgcc gcactggcgg caccatcact gccggcaacc acttcgacgc ctgggctcgc     480
gccggcatgc ctctgggcaa ctttaagtac tacatgatca tggccaccga gggctaccgc     540
tcgagcggca actcgtctat ccgcgtcggc tcctaa                              576

<210> SEQ ID NO 91
<211> LENGTH: 585
<212> TYPE: DNA
<213> ORGANISM: Actinomadura amylolytica

<400> SEQUENCE: 91
gctgctcctg tcaccagcaa ccagacgggc acgcacgacg gctacttcta ctccttctgg      60
acggacgctc ctggcaccgt ctccatggag ctgggcagcg gcggcaacta cagcacctcg     120
tggcgcaaca cgggcaactt cgtcgctggc aagggctgga gcaccggcgg ccgacgcacc     180
gtcacgtact ccggcagctt caacccctcg ggcaacgcct acctcaccct gtacggctgg     240
acgcgcaacc ctctggtcga gtactacatc gtcgacaact ggggcaccta ccgccctacg     300
ggcacctaca agggcaccgt cacgtccgac ggtggcacgt acgacatcta cgagaccacg     360
cgctacaacg ctcctagcat cgagggcacc cgcacgttca agcagtactg gtcggtccgc     420
cagtcgcgcc gcaccggcgg caccatcacc tcgggcaacc actttgacgc ttgggctcgc     480
tacggcatga gcctcggctc ccacgactac atgatcatgg ctacggaggg ctaccagagc     540
agcggctcca gcaacatcac ggtcggcggc tcgtccaacc cctaa                   585

<210> SEQ ID NO 92
<211> LENGTH: 585
<212> TYPE: DNA
<213> ORGANISM: Artificial Sequence
<220> FEATURE:
<223> OTHER INFORMATION: Variant of Actinomadura amylolytica

<400> SEQUENCE: 92
gctgcttgcg tcaccagcaa ccagacgggc acgcacgacg gctacttcta ctccttctgg      60
acggacgctc ctggcaccgt ctccatgtgc ctgggcagcg gcggcaacta cagcacctcg     120
tggcgcaaca cgggcaactt cgtcgctggc aagggctgga gcaccggcgg ccgacgcacc     180
gtcacgtact ccggcagctt caacccctcg ggcaacgcct acctcaccct gtacggctgg     240
```

```
acgcgcaacc ctctggtcga gtactacatc gtcgacaact ggggcaccta ccgccctacg      300
ggcacctaca agggcaccgt cacgtccgac ggtggcacgt acgacatcta cgagaccacg      360
cgctacaacg ctcctagcat cgagggcacc cgcacgttca agcagtactg gtcggtccgc      420
cagtcgcgcc gcaccggcgg caccatcacc tcgggcaacc actttgacgc ttgggctcgc      480
tacggcatga gcctcggctc ccacgactac atgatcatgg ctacggaggg ctaccagagc      540
agcggctcca gcaacatcac ggtcggcggc tcgtccaacc cctaa                      585
```

<210> SEQ ID NO 93
<211> LENGTH: 585
<212> TYPE: DNA
<213> ORGANISM: Artificial Sequence
<220> FEATURE:
<223> OTHER INFORMATION: Variant of Actinomadura amylolytica

<400> SEQUENCE: 93

```
gctgcttgtg tcaccagcaa ccagacgggc acgcacgacg gctacttcta ctccttctgg       60
acggactccc ctggcaccgt catcatgtgt ctgggcagcg gcggcaacta cagcacctcg      120
tggcgcaaca cgggcaactt cgtcgctggc aagggctgga gcaccggcgg ccgacgcacc      180
gtcacgtact ccggcagctt caacccctcg ggcaacgcct acctcaccct gtacggctgg      240
acgcgcaacc ctctggtcga gtactacatc gtcgacaact ggggcaccta ccgccctacg      300
ggcacctaca agggcaccgt cacgtccgac ggtggcacgt acgacatcta cgagaccacg      360
cgctacaacg ctcctagcat cgagggcacc cgcacgttca agcagtactg gtcggtccgc      420
cagtcgcgcc gcaccggcgg caccatcacc tcgggcaacc actttgacgc ttgggctcgc      480
tacggcatga gcctcggctc ccacgactac atgatcatgg ctacggaggg ctaccagagc      540
agcggctcca gcaacatcac ggtcggcggc tcgtccaacc cctaa                      585
```

<210> SEQ ID NO 94
<211> LENGTH: 576
<212> TYPE: DNA
<213> ORGANISM: Thermopolyspora flexuosa

<400> SEQUENCE: 94

```
gacaccacga tcacccagaa ccagaccggc tacgacaacg gctacttcta cagcttccgc       60
actgacgccc ctggcaccgt ctctatgacc ctccactcgg gcggctctta ctcgacctct      120
tggcgcaaca ctggcctctt tctggccggc aagggctgga gcaccggcgg gcgccgcacc      180
gtcacgtaca acgcctcctt taaccctagc ggcaacgccc gcctcaccct gtacggctgg      240
acccgcaacc ctctcgtcag ctaccacatc gtcgagagct ggggcacgta ccgcccaact      300
ggcacctaca agggcaccgt cacgactgac ggcggcacct acgacatcta cgagacctgg      360
cgctacaacg ccccttctat cgagggcacg cgcacttacc agcagttctg gtctgtccgc      420
cagcagaagc gcacctcggg cacgatcacc atcggcaacc acttcgacgc ttgggcccgc      480
gctggcatga acctcggctc ccacgactac cagatcatgg ccaccgaggg ctaccagtcc      540
tcgggcagct ctaccgtcag catctctgag ggctaa                                576
```

<210> SEQ ID NO 95
<211> LENGTH: 576
<212> TYPE: DNA
<213> ORGANISM: Artificial Sequence
<220> FEATURE:
<223> OTHER INFORMATION: Variant of Thermopolyspora flexuosa

<400> SEQUENCE: 95

-continued

```
gacacctgca tcacccagaa ccagaccggc tacgacaacg gctacttcta cagcttccgc      60
actgacgccc ctggcaccgt ctctatgtgc ctccactcgg gcggctctta ctcgacctct     120
tggcgcaaca ctggcctctt tctggccggc aagggctgga gcaccggcgg cgccgcacc     180 gtcacgtaca acgcctcctt taaccctagc ggcaacgccc gcctcaccct gtacggctgg     240
acccgcaacc ctctcgtcag ctaccacatc gtcgagagct ggggcacgta ccgcccaact     300
ggcacctaca agggcaccgt cacgactgac ggcggcacct acgacatcta cgagacctgg     360
cgctacaacg ccccttctat cgagggcacg cgcacttacc agcagttctg gtctgtccgc     420
cagcagaagc gcacctcggg cacgatcacc atcggcaacc acttcgacgc ttgggcccgc     480
gctggcatga acctcggctc ccacgactac cagatcatgg ccaccgaggg ctaccagtcc     540
tcgggcagct ctaccgtcag catctctgag ggctaa                              576
```

<210> SEQ ID NO 96
<211> LENGTH: 576
<212> TYPE: DNA
<213> ORGANISM: Artificial Sequence
<220> FEATURE:
<223> OTHER INFORMATION: Variant of Thermopolyspora flexuosa

<400> SEQUENCE: 96

```
gacacctgca tcacccagaa ccagaccggc tacgacaacg gctacttcta cagcttccgc      60
actgacagcc ctggcaccgt cattatgtgc ctccactcgg gcggctctta ctcgacctct     120
tggcgcaaca ctggcctctt tctggccggc aagggctgga gcaccggcgg cgccgcacc     180 gtcacgtaca acgcctcctt taaccctagc ggcaacgccc gcctcaccct gtacggctgg     240
acccgcaacc ctctcgtcag ctaccacatc gtcgagagct ggggcacgta ccgcccaact     300
ggcacctaca agggcaccgt cacgactgac ggcggcacct acgacatcta cgagacctgg     360
cgctacaacg ccccttctat cgagggcacg cgcacttacc agcagttctg gtctgtccgc     420
cagcagaagc gcacctcggg cacgatcacc atcggcaacc acttcgacgc ttgggcccgc     480
gctggcatga acctcggctc ccacgactac cagatcatgg ccaccgaggg ctaccagtcc     540
tcgggcagct ctaccgtcag catctctgag ggctaa                              576
```

<210> SEQ ID NO 97
<211> LENGTH: 301
<212> TYPE: PRT
<213> ORGANISM: Actinomadura flexuosa

<400> SEQUENCE: 97

```
Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110
```

-continued

```
Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
        130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
                180                 185                 190

Asn Pro Gly Asn Pro Gly Asn Pro Gly Asn Pro Gly Asn Pro Gly Asn
                195                 200                 205

Pro Gly Asn Pro Gly Gly Gly Cys Val Ala Thr Leu Ser Ala Gly Gln
        210                 215                 220

Gln Trp Ser Asp Arg Tyr Asn Leu Asn Val Ser Val Ser Gly Ser Asn
225                 230                 235                 240

Asn Trp Thr Val Arg Met Asp Val Pro Tyr Pro Ala Arg Ile Ile Ala
                245                 250                 255

Thr Trp Asn Ile His Ala Gln Trp Pro Glu Ser Gln Val Leu Ile Ala
                260                 265                 270

Arg Pro Asn Gly Asn Gly Asn Asn Trp Gly Val Thr Ile Gln His Asn
        275                 280                 285

Gly Asn Trp Thr Trp Pro Thr Val Thr Cys Thr Ala Asn
        290                 295                 300
```

<210> SEQ ID NO 98
<211> LENGTH: 906
<212> TYPE: DNA
<213> ORGANISM: Actinomadura flexuosa

<400> SEQUENCE: 98

```
gacaccacca tcacccagaa ccagaccggg tacgacaacg gctacttcta ctcgttctgg      60
accgacgcgc ccgggaccgt ctccatgacc ctccactcgg gcggcagcta cagcacctcg     120
tggcggaaca ccgggaactt cgtcgccggc aagggctggt ccaccggcgg acggcggacc     180
gtgacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
tccgccggcc agcagtggag cgaccgctac aacctcaacg tctcggtcag cggctcgaac     720
aactggacgg tccggatgga cgtgccctac ccggcccgca tcatcgccac ctggaacatc     780
cacgcccagt ggcccgagtc ccaggtgctc atcgccagac ccaacggcaa cggcaacaac     840
tggggcgtga cgatccagca caacggcaac tggacctggc cgacggtcac ctgtaccgcg     900
aactga                                                                906
```

XYLANASE VARIANTS

TECHNICAL FIELD

The present disclosure generally relates to field of enzyme technology. The disclosure relates particularly, though not exclusively, to xylanase variants which exhibit an improved xylan degrading performance and stability in different chemical and thermal environments, making them useful in various applications where degradation of xylan is desired, such as pulp or silage processing and feedstuff or foodstuff preparation.

BACKGROUND

This section illustrates useful background information without admission of any technique described herein representative of the state of the art.

Plant cell walls consist mainly of a complex mixture of polysaccharides, primarily cellulose, lignin and hemicellulose. Xylan is the major hemicellulose component in most materials originating from plants, consisting of a polysaccharide backbone of β-1,4-linked xylose residues that often carry acetyl, arabinosyl and glucuronosyl substituents. Endo-β-1,4-xylanases (EC 3.2.1.8) are enzymes that act on xylans and xylo-oligosaccharides, by degrading the linear polysaccharide, resulting in mixtures of smaller xylooligosaccharides and xylose (monosaccharide).

The demand of industrially applicable xylanases hydrolyzing xylans has markedly increased, and there is a constant need for enzymes with improved properties. Xylanases that are active and stable at high temperature, as well as in alkaline pH, are especially desirable in many industrial processes. Such processes include, for example, enzyme-aided bleaching of pulp, wherein xylanases are used as simple and cost-effective alternatives to toxic chlorine-containing chemicals.

Xylanases are also useful as animal feed additives, because of their beneficial effects in improving feed nutrient utilization. Plant-based animal feed contains xylan, which in larger quantities may compromise nutrient digestion, microbial colonization and growth in the livestock. Xylanase enzyme addition in animal feed has beneficial effects, such as increased growth rate of the livestock, increased feed conversion ratio, and increased feed efficiency. Xylan solubilization and degradation by xylanases results in reduced intestinal viscosity of the livestock and increased release of nutrients from grain endosperm and aleurone layers. Also, sugar oligomers, xylooligosaccharides (XOSs) made up of xylose units have been suggested to act as prebiotics, giving a variety of health benefits to livestock animals.

Other industrial or commercial applications in which xylanases are utilized are for instance, silage processing, biomass conversion for biofuel production, as well as starch, food, baking (such as bread making), and beverage (such as clarification of fruit juice and wine, or alcoholic fermentation) industries.

Actinomycetes are known to produce xylanases and some of them produce very thermostable alkaline-tolerant xylanase enzymes. Thermophilic actinomycete strains are useful sources of xylanases for industrial processes. Xylanase polypeptides comprise a catalytic module (core) and many of them also contain a carbohydrate binding module (CBM) separated from the core by a linker region. Xylan degrading enzymes with the modular structure defined above are produced by fungi and bacteria, such as strains of actinomycete, including *Actinomadura (Nonomuraea) flexuosa* (e.g. *N. flexuosa* Xyn11A and Xyn10A consist of a core, linker and CBM).

The present disclosure describes variants of actinomycete xylanases and variants of a truncated *Actinomadura (Nonomuraea) flexuosa* Xyn11 xylanase (Nf Xyn11A, also named as AM35), named as AM24. The AM24 xylanase and method for its production was described in EP 1737951 1. AM24 is a truncated xylanase from the full-length xylanase AM35 originating from *Actinomadura (Nonomuraea) flexuosa*. AM24 differs from the full-length xylanase AM35, in that the carbohydrate binding domain (CBM) and part of the linker between core and CBM has been genetically removed. The full length *Actinomadura (Nonomuraea) flexuosa* Xyn11A (Nf Xyn11A, AM35) xylanase protein has also been described before (EP 1737951 B1).

It is an object of the present disclosure to provide variants of xylanase that exhibit xylanase activity and that have performance and stability that allows their use in industrial processes. Another object of the present disclosure is to provide variants of xylanase with improved properties when used in industrial processes. Yet another object of the present disclosure is to provide variants that can be used in enzyme compositions for xylan degradation or modification.

SUMMARY

The present application concerns the inventions defined in the appended independent claims, and their embodiments disclosed below.

The invention is based on development of xylanase variants by modifying a parent xylanase polypeptide AM24 or another actinomycete xylanase polypeptide homologous to AM24. The inventors have surprisingly found, and show in the examples below, that by incorporating at least one disulfide bridge, as well as an amino acid substitution at the position corresponding to the position 23, or 28, or at both of the positions 23 and 28, in the parent xylanase variant polypeptide, it is possible to obtain a variant which has improved, i.e. increased, performance in xylan degradation as well as improved stability, compared to the parent xylanase AM24 or parent AM24 xylanase homologue. The performance and stability is improved particularly when the reaction conditions require high temperature. The novel variant polypeptides of xylanase have a high performance and stability in wide range of industrial processes, and provide thus improved properties for enzyme compositions for xylan degradation and modification in those processes.

According to a first aspect is provided a variant polypeptide comprising an amino acid sequence having at least 79%, but less than 100% amino acid sequence identity with amino acids 1-191 of SEQ ID NO: 1, wherein the amino acid sequence has:

xylanase activity,
  at least one disulfide bridge between two Cys residues in the 1-191 amino acid region, and
  an amino acid substitution at the position 23 or 28, or at the positions 23 and 28, the positions corresponding to the positions 23 and 28 of the SEQ ID NO: 1.

The present variant polypeptide is advantageous in having improved thermostability, pH stability and performance i.e. xylan degrading activity, these features being measurable as described in example 4 and 5.

In an embodiment is provided a functional fragment of the present variant polypeptide of xylanase.

According to a second aspect is provided a fusion protein, comprising the amino acid sequence of the variant polypeptide of the first aspect, and at least one:

amino acid sequence providing a secretory signal sequence;

amino acid sequence which facilitates purification, such as an affinity tag or His-tag; amino acid sequence controlling and enhancing the production of the recombinant polypeptide, such as a carrier polypeptide;

amino acid sequence encoding a protease cleavage site;

amino acid sequence having an enzyme activity; and/or amino acid sequence providing for the fusion protein with binding affinity, such as a carbohydrate binding moiety.

According to a third aspect is provided an enzyme composition comprising the variant polypeptide of the first aspect, or the fusion protein of the second aspect.

The enzyme composition is particularly good for pulp processing, such as boosting the bleaching process and enhancing the refining efficiency of pulp, as well as for industrial feedstuff or foodstuff preparation, as the variant of xylanase has a good stability and specific activity when used to degrade xylan in such processes.

According to a fourth aspect is provided a recombinant host cell comprising genetic elements that allow producing at least one recombinant polypeptide comprising the variant polypeptide of the first aspect, or the fusion protein of the second aspect.

The variant polypeptide according to the disclosure has properties that make the variant polypeptide useful in enzyme compositions for industrial applications.

In an embodiment is provided an enzyme preparation comprising the variant polypeptide having xylanase activity and obtainable by using the present host cell.

According to a fifth aspect is provided a method for producing the variant polypeptide of the first aspect or the fusion protein of the second aspect, comprising:

a. cultivating the recombinant host cell of the fourth aspect in conditions allowing production of the recombinant polypeptide; and optionally b. recovering the recombinant polypeptide.

The method provides an efficient way to produce the variant polypeptide of xylanase or the fusion protein comprising the variant polypeptide of xylanase and at least one amino acid sequence according to the second aspect. Because the variant polypeptide is produced in a recombinant host cell, a production system is provided which can be optimized, tailored, and controlled in a desired manner. The variant polypeptide produced by the method differs from parent xylanase at a structural and functional level.

According to a sixth aspect is provided a method for degrading or modifying xylan containing material, comprising treating said xylan containing material with an effective amount of the variant polypeptide of the first aspect, the fusion protein of the second aspect, or the enzyme composition of the third aspect. In an embodiment the treating comprises bringing the xylan containing material in contact with the variant polypeptide, the fusion protein, or the enzyme composition in an aqueous medium.

According to a seventh aspect is provided a use of the variant polypeptide of the first aspect, or the fusion protein of the second aspect, or the enzyme composition of the third aspect, in industrial processes or commercial applications, such as pulp or silage processing.

According to an eighth aspect is provided a use of the variant polypeptide of the first aspect, or the fusion protein of the second aspect, or the enzyme composition of the third aspect, in feedstuff or foodstuff preparation.

In an embodiment is provided a use of the variant polypeptide of the first aspect, or the fusion protein of the second aspect, or the enzyme composition of the third aspect in pulp processing, such as promoting lignin removal and/or cellulose hydrolysis and enhancing the susceptibility of pulp to refining.

In an embodiment is provided a use of the variant polypeptide of the first aspect, or the fusion protein of the second aspect, or the enzyme composition of the third aspect in animal feed, wherein the feed is optionally used for feeding animals, improving weight gain and feeding efficiency of the animals.

In an embodiment is provided a use of the variant polypeptide of the first aspect, or the fusion protein of the second aspect, or the enzyme composition of the third aspect in foodstuff preparation. The variant polypeptide can be used in extraction of coffee, in processing of plant oils or starch, in degumming of plant fiber sources, in baking, in dough conditioning, in bread making, and in beverage industries (such as clarification of fruit juice and wine, or alcoholic fermentation).

The present variant of xylanase is advantageous in having an improved performance in degrading xylan in the process conditions that require increased stability. As shown in the examples provided below, the claimed variant polypeptide of xylanase has a performance and stability, which are improved when compared to the parent AM24 xylanase or parent AM24 xylanase homologue, depending on the origin of the variant.

Different non-binding example aspects and embodiments have been illustrated in the foregoing. The embodiments in the foregoing are used merely to explain selected aspects or steps that may be utilized in different implementations. Some embodiments may be presented only with reference to certain example aspects. It should be appreciated that corresponding embodiments may apply to other example aspects as well.

BRIEF DESCRIPTION OF THE FIGURES

Some example embodiments will be described with reference to the accompanying figures, in which:

FIG. 2. Shows alignment of amino acid sequences of AM24 and mature deduced core regions of its close homologues selected for production in *Trichoderma reesei*. The alignment of sequences was performed using Clustal Omega (1.2.4) multiple sequence alignment. The mature core region of AM24 consists of amino acids 1-191 from SEQ ID NO:1, basing on information published in Leskinen et al. (2005). The alignment of FIG. 2 displays the following symbols denoting the degree of conservation observed in each vertical column: An*(asterisk) indicates positions which have a single, fully conserved residue. A:(colon) indicates positions which have conservation between groups of strongly similar properties. A. (period) indicates positions which have conservation between groups of weakly similar properties.

FIG. 3A: Results from 5 min reaction time assay; FIG. 3B: Results from 60 min reaction time assay. The activity values were related to the activity of the corresponding xylanase analyzed at 80° C. using 5 min reaction time. This activity was set as 100. The values presented are averages from two parallel reactions. AM24 denotes the parent xylanase, the other samples denote the different AM24 variants.

FIG. 4A: Reaction conditions pH 8, 5 min reaction; FIG. 4B: Reaction conditions pH 8, 60 min reaction; FIG. 4C: Reaction conditions pH 9, 5 min reaction; FIG. 4D: Reaction conditions pH 9, 60 min reaction. The activity values were related to the activity of the corresponding xylanase analyzed at pH 7, 80° C. using 5 min reaction time. This value was set as 100. The values are averages from two parallel reactions.

SEQUENCE LISTING

Figure 1A:
FIGS. 1A and 1B. show a phylogenetic tree of AM24 core sequence and its homologues. The tree is divided into two FIGS. 1A and 1B, the arrows representing the connecting link between the two figures. The family tree from 100 closest homologues to AM24 core, designed using blastp search (blast.ncbi.nlm.nih.gov/Blast.cgi?PAGE=Proteins) and the Phylogenetic Tree option in the Clustal Omega multiple sequence alignment program (www.ebi.ac.uk/Tools/msa/clustalo/). The amino acid sequence of AM24 (Nf_Xyn11A core, amino acids 1-191 from SEQ ID NO:1, core region according to Leskinen et al., 2005) was used as the query sequence. The algorithm parameters used are explained in more detail in the Example 2.

The sequence listing submitted via EFS, in compliance with 37 CFR § 1.821(c)(1), is incorporated herein by reference. The sequence listing ASCII text file submitted via EFS contains the file "60253010US SeqListingCorrected.txt", created on Dec. 19, 2023, which is 141,415 bytes in size.

SEQ ID NO: 1 AM24, amino acid sequence of the truncated form of *Nonomuraea flexuosa* Xyn11A protein (AM35). AM24 contains the amino acids D44-L263 of the full-length wild-type NfXyn11A, encoded by am24 nucleotide sequence.

SEQ ID NO: 2 Amino acid sequence of the AM24 variant C31-4 comprising the mutations T3C, A23S, S28I, T30C SEQ ID NO: 3 Amino acid sequence of the AM24 variant comprising the mutations T3C, T30C SEQ ID NO: 4 Amino acid sequence of the AM24 variant comprising the mutations T3C, A23S, T30C SEQ ID NO: 5 Amino acid sequence of the AM24 variant comprising the mutations T3C, S28I, T30C SEQ ID NO: 6 Amino acid sequence of the AM24 variant comprising the mutation A23S SEQ ID NO: 7 Amino acid sequence of the AM24 variant comprising the mutation S28I SEQ ID NO: 8 Amino acid sequence of the AM24 variant comprising the mutations A23S, S28I SEQ ID NO: 9 Amino acid sequence of the AM24 variant comprising the mutations T3C, A23Y, S28I, T30C SEQ ID NO: 10 Amino acid sequence of the AM24 variant comprising the mutations T3C, A23H, S28I, T30C SEQ ID NO: 11 Amino acid sequence of the AM24 variant comprising the mutations T3C, A23T, S28I, T30C SEQ ID NO: 12 Amino acid sequence of the AM24 variant comprising the mutations T3C, A23M, S28I, T30C SEQ ID NO: 13 Amino acid sequence of the AM24 variant comprising the mutations T3C, A23R, S28I, T30C SEQ ID NO: 14 Amino acid sequence of the AM24 variant comprising the mutations T3C, A23S, S28L, T30C SEQ ID NO: 15 Amino acid sequence of the AM24 variant comprising the mutations T3C, A23S, S28R, T30C SEQ ID NO:16 Amino acid sequence of the AM24 variant comprising the mutations T3C, A23S, S28M, T30C SEQ ID NO: 17 Amino acid sequence of the AM24 variant comprising the mutations T3C, A23S, S28Q, T30C SEQ ID NO: 18 Amino acid sequence of the AM24 variant comprising the mutations T3C, A23S, S28Y, T30C SEQ ID NO: 19 Amino acid sequence of the AM24 variant comprising the mutations T3C, A23S, S28W, T30C SEQ ID NO: 20 Amino acid sequence of the AM24 variant comprising the mutations T3C, A23S, S28T, T30C SEQ ID NO: 21 Amino acid sequence of the AM24 variant comprising the mutations T3C, A23S, S28N, T30C SEQ ID NO: 22 Amino acid sequence of the AM24 variant comprising the mutations T3C, A23S, S28V, T30C SEQ ID NO: 23 Amino acid sequence of the AM24 variant comprising the mutations T3C, A23R, S28L, T30C SEQ ID NO: 24 Amino acid sequence of the AM24 variant comprising the mutations T3C, A23R, S28Q, T30C SEQ ID NO: 25 Amino acid sequence of the AM24 variant comprising the mutations T3C, A23H, S28L, T30C SEQ ID NO: 26 Amino acid sequence of the AM24 variant comprising the mutations T3C, A23T, S28L, T30C SEQ ID NO: 27 Amino acid sequence of the AM24 variant comprising the mutations T3C, A23W, S28I, T30C SEQ ID NO: 28 Amino acid sequence of the AM24 variant comprising the mutations T3C, A23P, S28I, T30C SEQ ID NO: 29 Amino acid sequence of the AM24 variant comprising the mutations T3C, A23S, S28P, T30C SEQ ID NO: 30 XB1, amino acid sequence of the 1st xylanase homologue of AM24, comprising the trimmed amino acids 26-219

SEQ ID NO: 31 XB1M1, amino acid sequence of the 1st xylanase homologue variant of XB1 comprising the mutations A3C, E30C SEQ ID NO: 32 XB1M2, amino acid sequence of the 1st xylanase homologue variant of XB1 comprising the mutations A3C, A23S, S28I, E30C SEQ ID NO: 33 XB2, amino acid sequence of the 2nd xylanase homologue of AM24, comprising the trimmed amino acids 39-229

SEQ ID NO: 34 XB2M1, amino acid sequence of the 2nd xylanase homologue variant of XB2 comprising the mutations A3C, E30C SEQ ID NO: 35 XB2M2, amino acid sequence of the 2nd xylanase homologue variant of XB2 comprising the mutations A3C, S28I, E30C SEQ ID NO: 36 XB3, amino acid sequence of the 3rd xylanase homologue of AM24, comprising the trimmed amino acids 37-231

SEQ ID NO: 37 XB3M1, amino acid sequence of the 3rd xylanase homologue variant of XB3 comprising the mutations A3C, E30C SEQ ID NO: 38 XB3M2, amino acid sequence of the 3rd xylanase homologue variant of XB3 comprising the mutations A3C, A23S, S28I, E30C SEQ ID NO: 39 XB4, amino acid sequence of the 4th xylanase homologue of AM24, comprising the trimmed amino acids 35-225

SEQ ID NO: 40 XB4M1, amino acid sequence of the 4th xylanase homologue variant of XB4 comprising the mutations V3C, T30C SEQ ID NO: 41 XB4M2, amino acid sequence of the 4th xylanase homologue variant of XB4 comprising the mutations V3C, A23S, S28I, T30C SEQ ID NO: 42 XB5, amino acid sequence of the 5th xylanase homologue of AM24, comprising the trimmed amino acids 43-236

SEQ ID NO: 43 XB5M1, amino acid sequence of the 5th xylanase homologue variant of XB5 comprising the mutations P3C, E30C SEQ ID NO: 44 XB5M2, amino acid sequence of the 5th xylanase homologue variant of XB5 comprising the mutations P3C, A23S, S28I, E30C SEQ ID NO: 45 XB6, amino acid sequence of the 6th xylanase homologue of AM24, comprising the trimmed amino acids 3-193

SEQ ID NO: 46 XB6M1, amino acid sequence of the 6th xylanase homologue variant of XB6 comprising the mutations T3C, T30C SEQ ID NO: 47 XB6M2, amino acid sequence of the 6th xylanase homologue variant of XB6 comprising the mutations T3C, A23S, S28I, T30C SEQ ID NO: 48 am24*, nucleotide sequence for the truncated form of Nf xyn11A encoding the truncated form (AM24) of the Nf Xyn11A protein (AM35). am24*has nine codon changes compared to wild type Nf xyn11A, described in more detail in Paloheimo et al. (2007).

SEQ ID NO: 49 nucleotide sequence encoding the AM24 variant C31-4 comprising the mutations T3C, A23S, S28I, T30C SEQ ID NO: 50 nucleotide sequence encoding the AM24 variant comprising the mutations T3C, T30C SEQ ID NO: 51 nucleotide sequence encoding the AM24 variant comprising the mutations T3C, A23S, T30C SEQ ID NO: 52 nucleotide sequence encoding the AM24 variant comprising the mutations T3C, S28I, T30C SEQ ID NO: 53 nucleotide sequence encoding the AM24 variant comprising the mutation A23S SEQ ID NO: 54 nucleotide sequence encoding the AM24 variant comprising the mutation S28I SEQ ID NO: 55 nucleotide sequence encoding the AM24 variant comprising the mutations A23S, S28I SEQ ID NO: 56 am24*, nucleotide sequence for the truncated form of Nf xyn11A encoding the truncated form (AM24) of the Nf Xyn11A protein (AM35). am24**has six of the nine codon changes of SEQ ID NO: 48 compared to wild-type Nf xyn11A, and in addition an internal NruI site has been removed by changing the alanine codon in position 218 from GCG to GCC. These same codon differences compared to wild type Nf xyn11A and removal of the internal NruI site are also included in AM24 variant encoding sequence in SEQ ID NO: 57-78.

SEQ ID NO: 57 nucleotide sequence encoding the AM24 variant C31-4 comprising the mutations T3C, A23S, S28I, T30C SEQ ID NO: 58 nucleotide sequence encoding the AM24 variant comprising the mutations T3C, A23Y, S28I, T30C SEQ ID NO: 59 nucleotide sequence encoding the AM24 variant comprising the mutations T3C, A23H, S28I, T30C SEQ ID NO: 60 nucleotide sequence encoding the AM24 variant comprising the mutations T3C, A23T, S28I, T30C SEQ ID NO: 61 nucleotide sequence encoding the AM24 variant comprising the mutations T3C, A23M, S28I, T30C SEQ ID NO: 62 nucleotide sequence encoding the AM24 variant comprising the mutations T3C, A23R, S28I, T30C SEQ ID NO: 63 nucleotide sequence encoding the AM24 variant comprising the mutations T3C, A23S, S28L, T30C SEQ ID NO: 64 nucleotide sequence encoding the AM24 variant comprising the mutations T3C, A23S, S28R, T30C SEQ ID NO: 65 nucleotide sequence encoding the AM24 variant comprising the mutations T3C, A23S, S28M, T30C SEQ ID NO: 66 nucleotide sequence encoding the AM24 variant comprising the mutations T3C, A23S, S28Q, T30C SEQ ID NO: 67 nucleotide sequence encoding the AM24 variant comprising the mutations T3C, A23S, S28Y, T30C SEQ ID NO: 68 nucleotide sequence encoding the AM24 variant comprising the mutations T3C, A23S, S28W, T30C SEQ ID NO: 69 nucleotide sequence encoding the AM24 variant comprising the mutations T3C, A23S, S28T, T30C SEQ ID NO: 70 nucleotide sequence encoding the AM24 variant comprising the mutations T3C, A23S, S28N, T30C SEQ ID NO: 71 nucleotide sequence encoding the AM24 variant comprising the mutations T3C, A23S, S28V, T30C SEQ ID NO: 72 nucleotide sequence encoding the AM24 variant comprising the mutations T3C, A23R, S28L, T30C SEQ ID NO: 73 nucleotide sequence encoding the AM24 variant comprising the mutations T3C, A23R, S28Q, T30C SEQ ID NO: 74 nucleotide sequence encoding the AM24 variant comprising the mutations T3C, A23H, S28L, T30C SEQ ID NO: 75 nucleotide sequence encoding the AM24 variant comprising the mutations T3C, A23T, S28L, T30C SEQ ID NO: 76 nucleotide sequence encoding the AM24 variant comprising the mutations T3C, A23W, S28I, T30C SEQ ID NO: 77 nucleotide sequence encoding the AM24 variant comprising the mutations T3C, A23P, S28I, T30C SEQ ID NO: 78 nucleotide sequence encoding the AM24 variant comprising the mutations T3C, A23S, S28P, T30C SEQ ID NO: 79 nucleotide sequence encoding the amino acids 26-219 of 1st xylanase homologue of AM24, XB1

SEQ ID NO: 80 nucleotide sequence encoding the 1st xylanase homologue variant XB1M1 comprising the mutations A3C, E30C SEQ ID NO: 81 nucleotide sequence encoding the 1st xylanase homologue variant XB1M2 comprising the mutations A3C, A23S, S28I, E30C SEQ ID NO: 82 nucleotide sequence encoding the amino acids 39-229 of 2nd xylanase homologue of AM24, XB2

SEQ ID NO: 83 nucleotide sequence encoding the 2nd xylanase homologue variant XB2M1 comprising the mutations A3C, E30C SEQ ID NO: 84 nucleotide sequence encoding the 2nd xylanase homologue variant XB2M2 comprising the mutations A3C, S28I, E30C SEQ ID NO: 85 nucleotide sequence encoding the amino acids 37-231 of 3rd xylanase homologue of AM24, XB3

SEQ ID NO: 86 nucleotide sequence encoding the 3rd xylanase homologue variant XB3M1 comprising the mutations A3C, E30C SEQ ID NO: 87 nucleotide sequence encoding the 3rd xylanase homologue variant XB3M2 comprising the mutations A3C, A23S, S28I, E30C SEQ ID NO: 88 nucleotide sequence encoding the amino acids 35-225 of 4th xylanase homologue of AM24, XB4

SEQ ID NO: 89 nucleotide sequence encoding the 4th xylanase homologue variant XB4M1 comprising the mutations V3C, T30C SEQ ID NO: 90 nucleotide sequence encoding the 4th xylanase homologue variant XB4M2 comprising the mutations V3C, A23S, S28I, T30C SEQ ID NO: 91 nucleotide sequence encoding the amino acids 43-236 of 5th xylanase homologue of AM24, XB5

SEQ ID NO: 92 nucleotide sequence encoding the 5th xylanase homologue variant XB5M1 comprising the mutations P3C, E30C SEQ ID NO: 93 nucleotide sequence encoding the 5th xylanase homologue variant XB5M2 comprising the mutations P3C, A23S, S28I, E30C SEQ ID NO: 94 nucleotide sequence encoding amino acids 3-193 of the 6th xylanase homologue of AM24, XB6

SEQ ID NO: 95 nucleotide sequence encoding the 6th xylanase homologue variant XB6M1 comprising the mutations T3C, T30C SEQ ID NO: 96 nucleotide sequence encoding the 6th xylanase homologue variant XB6M2 comprising the mutations T3C, A23S, S28I, T30C SEQ ID NO: 97 AM35 amino acid sequence for the full length mature Nf Xyn11A protein encoded by am35 nucleotide sequence (comprising amino acids 44-344 of the full-length Nt Xyn11A; Leskinen et al., 2005)

SEQ ID NO: 98 am35, nucleotide sequence encoding the full length mature Nf Xyn11A AM35 protein

DETAILED DESCRIPTION

The invention relates to variant polypeptides of xylanase having introduced substitutions in their amino acid sequence, resulting in improved properties, such as improved thermostability and pH stability.

As used herein, the term "homologue" or "xylanase homologue" refers to a xylanase sequence of DNA, RNA, or amino acids, which has a certain level of biological homology i.e. similarity to another xylanase sequence of DNA, RNA, or amino acids, wherein the similarity is expressed as % of identical residues in the sequence, or as % of sequence identity/similarity In an embodiment, the xylanase homologue is an AM24 xylanase homologue.

The term "Xylan" refers to matrix polysaccharides or heteropolymers, composed of a repeating β-1,4-linked xylose residue backbone, with various side-chain groups. Xylan polysaccharides can be categorized into classes O-acetylglucuronoxylans (AcGX), O-acetylarabinoxylans (AcAX), O-acetylglucuronoarabinoxylans (AcGAX), and arabinoglucuronoxylans (AGX), based on the substituted side-chain groups. The xylan containing material comprises plant-based or plant-originating material.

As used herein, the term "xylanase" denotes a xylanase enzyme defined according to that known in the art as endo-1,4-β-xylanase, or 4-β-D-xylan xylanohydrolase, known to catalyze the endohydrolysis of (1→4)-β-D-xylosidic linkages in xylans. Xylans have the alternative names endo-(1→4)-β-xylan 4-xylanohydrolase, endo-1,4-xylanase, xylanase, β-1,4-xylanase, endo-1,4-xylanase, endo-β-1,4-xylanase, endo-1,4-β-D-xylanase, 1,4-β-xylan xylanohydrolase, β-xylanase, β-1,4-xylan xylanohydrolase, endo-1,4-β-xylanase and β-D-xylanase. Xylanases are classified according to the Enzyme Nomenclature as EC 3.2.1.8.

As used herein, Nf xyn11A denotes a *Nonomuraea flexuosa* xylanase gene encoding a xylanase Nf Xyn11A from the family 11, also named as AM35.

As used herein, AM35 denotes the wild-type mature xylanase, which is the parent polypeptide used for the AM24 polypeptide. The amino acids of the mature AM35 protein correspond to the amino acid sequence of SEQ ID NO: 97.

As used herein, the AM24 (also called AM24 protein herein) is the parent polypeptide for the AM24 variant polypeptides according to the disclosure. The AM24 is encoded by a shortened DNA sequence encoding a truncated form of the xylanase AM35 (Nf Xyn11A). The AM24 protein comprises the catalytic module (core), and lacks the carbohydrate binding module (CBM) and part of the linker region between core and CBM. The amino acids of the mature polypeptide of AM24 correspond to the amino acid sequence of SEQ ID NO: 1, comprising the amino acids D1-L220, whereas the "mature core polypeptide" of AM24 comprises the amino acids D1-G191 of SEQ ID NO:1.

As used herein, the term "variant" means a sequence or a fragment of a sequence (nucleotide or amino acid) inserted, substituted or deleted by one or more nucleotides/amino acids, or which is chemically modified. The term variant may in some embodiments also include the variant polypeptide of xylanase, the fusion protein including the variant polypeptide of xylanase, or the recombinant xylanase enzyme.

The term "xylanase variant" and "variant xylanase" and "variant of xylanase" means any xylanase molecule obtained by site-directed or random mutagenesis, insertion, substitution, deletion, recombination and/or any other protein engineering method, which leads to xylanases that differ in their amino acid sequence from the parent xylanase, the parent xylanase being a wild-type xylanase or a xylanase variant itself. The terms "wild type xylanase", "wild type enzyme", "wild type", or "wt" in accordance with the disclosure, describe a xylanase enzyme with an amino acid sequence found in nature or a fragment thereof. The variant encoding gene can be synthesised or the parent gene be modified using genetic methods, e.g. by site-directed mutagenesis, a technique in which one or more than one mutations are introduced at one or more defined sites in a polynucleotide encoding the parent polypeptide.

The term "variant polypeptide" of xylanase according to the first aspect, may also be referred to by using the name given to variant, e.g. C31-4 or variant C31-4.

As used herein, the term "homologue variant" or "variant of a homologue" refers to any variant molecule from AM24 xylanase homologue, obtained by synthesizing the corresponding gene or by modifying the parent gene by site-directed or random mutagenesis, insertion, substitution, deletion, recombination and/or any other protein engineering method, which leads to a AM24 xylanase homologue variant which differs in its amino acid sequence from the parent xylanase homologue, the parent xylanase homologue being a wild-type xylanase or a xylanase variant itself. In an embodiment, the expression "xylanase homologue variant of XB1", or similar, refers to a variant of AM24 xylanase homologue, the homologue being XB1.

As used herein, the term "mature polypeptide" means any polypeptide wherein at least one signal sequence or signal peptide or signal peptide and a putative pro-peptide is cleaved off. For example, the "mature polypeptide" of AM24 comprises the amino acids D1-L220 of SEQ ID NO:1 and the "mature core polypeptide" of AM24 comprises the amino acids D1-G191 of SEQ ID NO:1.

As used herein, a "peptide" and a "polypeptide" are amino acid sequences including a plurality of consecutive polymerized amino acid residues. For purpose of this disclosure, peptides are molecules including up to 20 amino acid residues, and polypeptides include more than 20 amino acid residues. The peptide or polypeptide may include modified amino acid residues, naturally occurring amino acid residues not encoded by a codon, and non-naturally occurring amino acid residues. As used herein, a "protein" may refer to a peptide or a polypeptide of any size. A protein may be an enzyme, a protein, an antibody, a membrane protein, a peptide hormone, regulator, or any other protein.

As used herein, "sequence identity" means the percentage of exact matches of amino acid residues between two optimally aligned sequences over the number of positions where there are residues present in both sequences. When one sequence has a residue with no corresponding residue in the other sequence, the alignment program allows a gap in the alignment, and that position is not counted in the denominator of the identity calculation.

As used herein, "sequence alignment" of the amino acid sequences means, aligning the sequences using Clustal Omega (1.2.4) multiple sequence alignment program (https://www.ebi.ac.uk/Tools/msa/clustalo/) as described by Sievers et al 2011, and using the default settings.

Unless otherwise specified, all references to a certain amino acid position refer to an amino acid of the SEQ ID NO: 1 in said position, or to an amino acid present or missing in the corresponding position of an amino acid sequence aligned with SEQ ID NO: 1.

As used herein, the term "disulfide bridge", or "disulfide bond", or "SS bridge" refers to a bond formed between the sulfur atoms of cysteine residues in a polypeptide or a protein. Disulfide bridges can be naturally occurring, or non-naturally occurring, and, for example, introduced by way of amino acid substitution(s).

As used herein, the term "corresponding positions" or "corresponding amino acid position" means aligning at least two amino acid sequences according to identified regions of similarity or identity as pairwise alignment or as multiple sequence alignment, thereby pairing up the corresponding amino acids. An example of corresponding positions is given in the FIG. 2, wherein the amino acids presented in the same vertical column are corresponding amino acids. For example, at the position 1, the amino acid D1 of AM24 and Q1 of XB1 are corresponding amino acids.

As used herein, "amino acid substitution" means an amino acid residue replacement with an amino acid residue that is different than the original amino acid in that specific replacement position. The term "amino acid substitution" can refer to both, conservative amino acid substitutions and non-conservative amino acid substitutions, which means the amino acid residue is replaced with an amino acid residue having a similar side chain (conservative), or a different side chain (non-conservative), as the original amino acid residue in that place.

The term "functional fragment" means a fragment or portion of the current variant polypeptide of xylanase, which retains about the same enzymatic function or effect.

"Xylanase activity" as used herein, refers to the xylan degrading activity. Degrading or modifying as used herein means that the xylan polysaccharide is hydrolyzed by a xylanase to xylose oligosaccharides or disaccharides. The xylan degrading activity of the polypeptides according to present disclosure can be tested according to test procedures known in the art. Examples 4 and 5 provide examples of a method for determining xylanase activity. By the term "xylanase activity retention" is meant the enzyme's ability to retain its xylanase activity when it is exposed to specific process conditions. In an embodiment, with increased activity retention of a xylanase enzyme is meant that the xylanase enzyme retains better its xylanase activity in the specified process conditions when compared to the parent xylanase AM24 in the same conditions.

In an embodiment the term "enzyme composition" means an enzymatic fermentation product, possibly isolated and purified, from a single species of a microorganism. The enzyme composition usually comprises a number of different enzymatic activities produced by the microorganism. In another embodiment the enzyme composition is a mixture of monocomponent enzymes, preferably enzymes derived from bacterial or fungal species by using conventional recombinant techniques. The enzymes are derived from fermentation of a microorganism or microorganisms, and are possibly isolated and purified. The enzymes in a mixture may originate from different species, preferably fungal or bacterial species, or they are present in a fermentation product of a microorganism which acts as a host cell for their production, such as in the production of a recombinant xylanase, when the microorganism simultaneously produces other enzymes in addition to the recombinant xylanase.

The term "stability" in context of enzyme or xylanase stability, describes the enzyme's property to withstand and/or function in process conditions that are not optimal for the activity and function of the enzyme in question, such process conditions being, for example, high temperature, pH or radiation, a certain concentration of inorganic salt or an organic solvent, or a specific reaction mixture compositions comprising e.g. proteases, stabilizers, builders, surfactants etc.

The term "stability" reflects the stability of the xylanase according to the disclosure as a function of time, e.g. how much activity is retained when the xylanase is exposed process conditions that are not optimal for the activity and function of the enzyme in question. Different methods are used to analyze the stability of xylanase variants. The unfolding temperatures of xylanases can be measured to assess the thermostability of a xylanase, as described in the Example 5. Also, the xylanase stability and residual activity can be measured using the "activity assay" with adjusted parameters as described in the Examples 4 and 5. The term "stability" includes stability during use in a process with high temperature conditions.

As used herein, "host cell" means any cell type that is susceptible to transformation, transfection, transduction, mating, crossing or the like with a nucleic acid construct or expression vector comprising a polynucleotide. The term "host cell" encompasses any progeny that is not identical due to mutations that occur during replication. Non-limiting examples of a host cell are fungal cells, preferably a filamentous fungal cell (e.g. *Trichoderma* or *Trichoderma reesei, Aspergillus* or *Aspergillus oryzae* or *Aspergillus niger, Thermothelomyces* or *Thermothelomyces heterothallica* or *Humicola* or *Humicola insolens* or *Fusarium* or *Fusarium venenatum*), bacterial cells, preferably gram-positive Bacilli (e.g. *Bacillus subtilis, B. licheniformis, B. megaterium, B. amyloliquefaciens, B. pumilus*), gram-negative bacteria (e.g. *Escherichia coli*), actinomycetales (e.g. *Streptomyces* sp., *Nonomuraea flexuosa*) and yeasts (e.g. *Saccharomyces cerevisiae, Pichia pastoris, Yarrowia lipolytica*).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" or "signal sequence" or a "secretory peptide" refers to an amino acid sequence which is a component or a part of a larger polypeptide, and which directs the larger polypeptide through a secretory pathway of a host cell in which it is produced. The secretory signal sequence can be native or it can be obtained from another source. Depending on the host cell, the larger polypeptide may be cleaved from the secretory peptide during transit through the secretory pathway, thereby forming a mature polypeptide lacking the secretory peptide.

The term "propeptide" or "pro-peptide" is a part of a protein that is cleaved during maturation or activation. Once cleaved, a propeptide generally has no independent biological function.

As used herein, the terms "domain" and "region" can be used interchangeably with the term "module".

The term "catalytic domain" or "catalytic module" or "core" denotes a domain of an enzyme, which may or may not have been modified or altered, but which has retained at least part of its original activity. The catalytic module region of a variant polypeptide of a xylanase according to the disclosure corresponds to the amino acids aligned with the amino acids 1-191 of SEQ ID NO: 1.

By the term "linker" or "spacer" is meant a polypeptide comprising at least two amino acids which may be present between the domains of a multidomain protein, for example an enzyme comprising a catalytic domain and a binding domain such as a carbohydrate binding module (CBM), or any other enzyme hybrid, or between two proteins or polypeptides produced as a fusion polypeptide, for example a fusion protein comprising two core enzymes. For example, the fusion protein of a catalytic domain with a CBM is provided by fusing a DNA sequence encoding the catalytic domain, a DNA sequence encoding the linker and a DNA sequence encoding the CBM sequentially into one open reading frame and expressing this construct.

The following abbreviations are used for amino acids:

| A | Ala | Alanine |
|---|-----|---------|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Substitutions are described using of the following nomenclature: amino acid residue in the protein scaffold; position; substituted amino acid residue(s). According to this nomenclature the substitution of, for instance, a single residue of alanine to tyrosine residue at position 23 is indicated as Ala23Tyr or A23Y.

As used herein, the term "comprising" includes the broader meanings of "including", "containing", and "comprehending", as well as the narrower expressions "consisting of" and "consisting only of".

As used herein, "expression" includes any step involved in the production of a polypeptide in a host cell including, but not limited to, transcription, translation, post-translational modification, and secretion. Expression may be followed by harvesting, i.e. recovering, the host cells or the expressed product.

As used herein, the term "silage" is a type of fodder or animal feed made from plant based material which has been preserved.

In an embodiment the variant polypeptide has xylanase activity, and an amino acid sequence with at least 79%, at least 81%, at least 82%, at least 84%, at least 87%, at least 90%, at least 93%, at least 95%, at least 96%, at least 97%, at least 98%, or at least 99% sequence identity with amino acids 1-191 of SEQ ID NO: 1. In an embodiment the variant polypeptide does not have 100% sequence identity with amino acids 1-191 of SEQ ID NO: 1. In an embodiment, the amino acid numbering of the variant polypeptide corresponds to that of SEQ ID NO: 1. In an alternative embodiment, the amino acid numbering of the variant polypeptide corresponds to that of SEQ ID NO: 1 partially.

In an embodiment the amino acid sequence of the variant polypeptide has at least 84%, preferably at least 85%, more preferably at least 86%, more preferably at least 87%, more preferably at least 88%, even more preferably at least 89%, most preferably at least 90%, but less than 100% amino acid sequence identity with amino acids 1-191 of SEQ ID NO: 1.

In an embodiment is disclosed a variant polypeptide comprising an amino acid sequence having at least 84%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 85%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 86%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 87%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 88%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 89%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 90%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment is disclosed a variant polypeptide comprising an amino acid sequence having at least 91%, 92%, 93%, 94% or 95%, but less than 100% amino acid sequence identity with amino acids 1-191 of SEQ ID NO: 1, wherein the amino acid sequence has: xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment, the variant polypeptide comprises an amino acid sequence having at least 79%, preferably at least 82%, more preferably at least 84%, even more preferably at least 87%, most preferably at least 90%, but less than 100% amino acid sequence identity with amino acids 1-191 of SEQ ID NO: 1, wherein the amino acids of the variant polypeptide corresponding to the amino acids 31-191 of SEQ ID NO: 1 have at least 90%, preferably at least 95%, more preferably at least 99%, even more preferably 100% sequence identity with amino acids 31-191 of SEQ ID NO: 1.

In an embodiment the variant polypeptide has: xylanase activity; the amino acids 1-191 of SEQ ID NO: 1, wherein an amino acid at the position 23 or 28, or at the positions 23 and 28 is/are substituted, the positions corresponding to the positions 23 and 28 of the SEQ ID NO: 1; and at least one further amino acid substitution resulting in a disulfide bridge between two Cys residues in the 1-191 amino acid region.

In an embodiment the variant polypeptide has xylanase activity, and an amino acid sequence with at least 79%, at least 81%, at least 82%, at least 84%, at least 87%, at least 90%, at least 93%, at least 95%, at least 96%, at least 97%, at least 98%, or at least 99% sequence identity with amino acids D1-L220 of SEQ ID NO: 1 of the parent AM24 xylanase polypeptide. In an embodiment the variant polypeptide has xylanase activity, and an amino acid sequence with less than 79% sequence identity with amino acids D1-L220 of SEQ ID NO: 1 of the parent AM24 xylanase polypeptide.

In an embodiment the variant polypeptide comprises the residues 3C and 30C, the positions corresponding to the positions 3 and 30 of the SEQ ID NO: 1, and the disulfide bridge of the variant polypeptide is formed between the residues 3C and 30C.

In an embodiment the variant polypeptide comprises the amino acid substitutions T3C or T30C, the positions corresponding to the positions 3 and 30 of the SEQ ID NO: 1, and the at least one disulfide bridge of the variant polypeptide is formed between the said substituted residues.

In an embodiment the variant polypeptide comprises a combination of the amino acid substitutions:

T3C and T30C, or T3C and N30C, or T3C and E30C, or T3C and Y30C, or T3C and D30C, or V3C and T30C, or V3C and N30C, or V3C and E30C, or V3C and Y30C, or V3C and D30C, or A3C and T30C, or A3C and N30C, or A3C and E30C, or A3C and Y30C, or A3C and D30C, or P3C and T30C, or P3C and N30C, or P3C and E30C, or P3C and Y30C, or P3C and D30C, wherein the substituted positions correspond to the positions 3 and 30 of the SEQ ID NO: 1, and the at least one disulfide bridge of the variant polypeptide is formed between the said two substituted residues.

In another embodiment the variant polypeptide comprises a disulfide bridge between Cys residues in the 1-191 amino acid region of the variant polypeptide, the positions of the Cys residues being different from the positions corresponding to positions 3 and 30 of the SEQ ID NO: 1.

In an embodiment the variant polypeptide comprises at least one disulfide bridge between Cys residues in the 1-30 amino acid region of the variant polypeptide, the positions of the amino acid region corresponding to positions 1 and 30 of the SEQ ID NO: 1.

In an embodiment the cysteine residues in the amino acid region of the variant polypeptide having at least 79%, but less than 100% amino acid sequence identity with amino acids 1-191 of SEQ ID NO: 1, are obtained, for example, through variant gene synthesis, the disulfide bridge thereby obtained between the said cysteine residues being non-naturally occurring. In an embodiment the cysteine residues are obtained through genetic modification of the parent gene. e.g. with site directed mutagenesis, the disulfide bridge thereby obtained between the said cysteine residues being also non-naturally occurring. Many protein engineering approaches or alternatively gene synthesis can be used to create amino acid substitutions at a specific location in an amino acid chain, allowing the natural or wild-type amino acid at a specific location, to be substituted with another amino acid residue. In an embodiment, at least two amino acid residues of the variant polypeptide 1-191 amino acid region are substituted with cysteines, thereby enabling a disulfide bond formation between the sulfur atoms of the substituent cysteine residues. In an another embodiment, the variant polypeptide comprises cysteine residues enabling the formation of a disulfide bridge in the 1-191 amino acid region of the variant polypeptide, in at least two alternative positions. In yet another embodiment, the variant polypeptide comprises cysteine residues enabling the formation of more than one disulfide bridge in the 1-191 amino acid region of the variant polypeptide.

In an embodiment, the at least one disulfide bridge in the 1-191 amino acid region stabilizes the variant polypeptide, thereby increasing the pH stability and thermostability of the variant polypeptide compared to variant AM24 without a disulfide bridge.

In an embodiment the variant polypeptide comprises at least one amino acid substitution at the position 23 or 28, or at the positions 23 and 28.

In an embodiment the variant polypeptide comprises at least one disulfide bridge between Cys residues in the 1-30 amino acid region of the variant polypeptide, and at least one amino acid substitution at the position 23 or 28, or at the positions 23, and 28 the positions corresponding to positions 1-30 of the SEQ ID NO: 1.

In an embodiment the variant polypeptide comprises at least one amino acid substitution at the position A23, S23 or S28, or at the positions A23 or S23, and S28.

In an embodiment the variant polypeptide comprises together with the at least one disulfide bridge between two Cys residues in the 1-191 region, at least one amino acid substitution at the position A23, or S28, or at the positions A23 and S28, the positions corresponding to the positions 23 and 28 of the SEQ ID NO: 1.

In an alternative embodiment the variant polypeptide comprises, together with the at least one disulfide bridge between two Cys residues in the 1-191 region, at least one amino acid substitution at the position S23 or S28, or at the positions S23 and S28, the positions corresponding to the positions 23 and 28 of the SEQ ID NO: 1.

In an embodiment, the substituted amino acid residues at position 23 or 28, or at the positions 23 and 28, are different from the original amino acid residues in these positions. In an embodiment, the substituent amino acid(s) is/are selected from the group consisting of H, I, L, M, N, P, Q, R, S, T, V, W or Y, with the provision that the substituent amino acid residue is different from the naturally-occurring amino acid residue in that position.

In an embodiment the variant polypeptide comprises:
a substitution of an amino acid at the position 23 to H, M, P, S, T, R, W or Y; or
a substitution of an amino acid at the position 28 to I, L, M, N, P, Q, R, T, V, W or Y; or
any combination thereof.

In an embodiment the variant polypeptide comprises:
a substitution of an amino acid at the position 23 to H, M, P, S, T, R, W or Y; or
a substitution of an amino acid at the position 28 to I, L, M, N, Q, R, T, V, W or Y; or
any combination thereof.

In an embodiment the variant polypeptide comprises the amino acid substitution, A23H, A23M, A23P, A23S, A23T, A23R, A23W or A23Y.

In an embodiment the variant polypeptide comprises the amino acid substitution S23H, S23M, S23P, S23T, S23R, S23W or S23Y.

In an embodiment the variant polypeptide comprises the amino acid substitution S28I, S28L, S28M, S28N, S28P, S28Q, S28R, S28T, S28V, S28W or S28Y.

In an embodiment the variant polypeptide comprises a combination of the amino acid substitutions: A23H and S28I, A23H and S28L, A23H and S28M, A23H and S28N, A23H and S28P, A23H and S28Q, A23H and S28R, A23H and S28T, A23H and S28V, A23H and S28W, A23H and S28Y, A23M and S28I, A23M and S28L, A23M and S28M, A23M and S28N, A23M and S28P, A23M and S28Q, A23M and S28R, A23M and S28T, A23M and S28V, A23M and S28W, A23M and S28Y, A23P and S28I, A23P and S28L, A23P and S28M, A23P and S28N, A23P and S28P, A23P and S28Q, A23P and S28R, A23P and S28T, A23P and S28V, A23P and S28W, A23P and S28Y, A23S and S28I, A23S and S28L, A23S and S28M, A23S and S28N, A23S and S28P, A23S and S28Q, A23S and S28R, A23S and S28T, A23S and S28V, A23S and S28W, A23S and S28Y, A23T and S28I, A23T and S28L, A23T and S28M, A23T and S28N, A23T and S28P, A23T and S28Q, A23T and S28R, A23T and S28T, A23T and S28V, A23T and S28W, A23T and S28Y, A23R and S28I, A23R and S28L, A23R and S28M, A23R and S28N, A23R and S28P, A23R and S28Q, A23R and S28R, A23R and S28T, A23R and S28V, A23R and S28W, A23R and S28Y, A23W and S28I, A23W and S28L, A23W and S28M, A23W and S28N, A23W and S28P, A23W and S28Q, A23W and S28R, A23W and S28T, A23W and S28V, A23W and S28W, A23W and S28Y, A23Y and S28I, A23Y and S28L, A23Y and S28M, A23Y and S28N, A23Y and S28P, A23Y and S28Q, A23Y and S28R, A23Y and S28T, A23Y and S28V, A23Y and S28W, A23Y and S28Y, S23H and S28I, S23H and S28L, S23H and S28M, S23H and S28N, S23H and S28P, S23H and S28Q, S23H and S28R, S23H and S28T, S23H and S28V, S23H and S28W, S23H and S28Y, S23M and S28I, S23M and S28L, S23M and S28M, S23M and S28N, S23M and S28P, S23M and S28Q, S23M and S28R, S23M and S28T, S23M and S28V, S23M and S28W, S23M and S28Y, S23P and S28I, S23P and S28L, S23P and S28M, S23P and S28N, S23P and S28P, S23P and S28Q, S23P and S28R, S23P and S28T, S23P and S28V, S23P and S28W, S23P and S28Y, S23T and S28I, S23T and S28L, S23T and S28M, S23T and S28N, S23T and S28P, S23T and S28Q, S23T and S28R, S23T and S28T, S23T and S28V, S23T and S28W, S23T and S28Y, S23R and S28I, S23R and S28L, S23R and S28M, S23R and S28N, S23R and S28P, S23R and S28Q, S23R and S28R, S23R and S28T, S23R and S28V, S23R and S28W, S23R and S28Y, S23W and S28I, S23W and S28L, S23W and S28M, S23W and S28N, S23W and S28P, S23W and S28Q, S23W and S28R, S23W and S28T, S23W and S28V, S23W and S28W, S23W and S28Y, S23Y and S28I, S23Y and S28L, S23Y and S28M, S23Y and S28N, S23Y and S28P, S23Y and S28Q, S23Y and S28R, S23Y and S28T, S23Y and S28V, S23Y and S28W, or S23Y and S28Y.

In a preferred embodiment the variant polypeptide has improved stability at high temperature. In a preferred embodiment the variant polypeptide has improved thermo-stability and/or pH-stability at high temperature.

In a preferred embodiment the variant polypeptide comprises an amino acid substitutions A23S and S28I together with the at least one disulfide bridge between two Cys residues in the 1-191 amino acid region, and has improved stability and/or activity compared to the parent xylanase AM24.

In a preferred embodiment the variant polypeptide comprises an amino acid substitutions A23S and S28I together with the at least one disulfide bridge between two Cys residues in the 1-191 amino acid region, and has improved thermostability and/or pH-stability compared to the parent xylanase AM24. In an embodiment the variant polypeptide comprises an amino acid substitutions A23S and S28I together with the at least one disulfide bridge between two Cys residues in the 1-191 amino acid region, and has higher xylanase activity at a high temperature of at least 70° C. preferably at least 80° C., more preferably at least 90° C., when compared to the parent xylanase AM24. In an embodiment the variant polypeptide comprises an amino acid substitutions A23S and S28I together with the at least one disulfide bridge between two Cys residues in the 1-191 amino acid region, and has an improved xylanase activity retention at pH of at least 7 and temperature of at least 70° C., preferably at least 80° C., more preferably at least 90° C., when compared to the parent xylanase AM24.

In a preferred embodiment the variant polypeptide comprises an amino acid substitutions A23S and S28I together with the at least one disulfide bridge between two Cys residues in the 1-30 amino acid region, and has improved stability and/or activity compared to the parent xylanase AM24. In a preferred embodiment the variant polypeptide comprises an amino acid substitutions A23S and S28I together with the at least one disulfide bridge between two Cys residues in the 1-30 amino acid region, and has improved thermostability and/or pH-stability compared to the parent xylanase AM24. In a preferred embodiment the variant polypeptide comprises an amino acid substitutions A23S and S28I together with the at least one disulfide bridge between two Cys residues in the 1-30 amino acid region, and has higher xylanase activity at a high temperature of at least 70° C. preferably at least 80° C., more preferably at least 90° C., when compared to the parent xylanase AM24. In an embodiment the variant polypeptide comprises an amino acid substitutions A23S and S28I together with the at least one disulfide bridge between two Cys residues in the 1-30 amino acid region, and has an improved xylanase activity retention at pH of at least 7, and temperature of at least 70° C., preferably at least 80° C., more preferably at least 90° C., when compared to the parent xylanase AM24.

In an embodiment the variant polypeptide comprises only one amino acid substitution A23S or S28I, together with the at least one disulfide bridge between two Cys residues in the 1-191 amino acid region, and has improved stability and/or activity compared to the parent xylanase AM24. In an embodiment the variant polypeptide comprises only one amino acid substitution A23S or S28I, together with the at least one disulfide bridge between two Cys residues in the 1-191 amino acid region, and has improved thermostability and/or pH-stability compared to the parent xylanase AM24. In an embodiment the variant polypeptide comprises only one amino acid substitution A23S or S28I, together with the at least one disulfide bridge between two Cys residues in the 1-191 amino acid region, and has higher xylanase activity at a high temperature of at least 70° C. preferably at least 80° C., more preferably at least 90° C., when compared to the parent xylanase AM24. In an embodiment the variant polypeptide comprises only one amino acid substitution A23S or S28I, together with the at least one disulfide bridge between two Cys residues in the 1-191 amino acid region, and has an improved xylanase activity retention at pH of at least 7 and temperature of at least of at least 70° C., preferably at least 80° C., more preferably at least 90° C., when compared to the parent xylanase AM24.

In an embodiment the variant polypeptide comprises an amino acid substitution at position 23 and/or 28, and lacks a disulfide bridge in the 1-191 amino acid region, and has improved stability and/or activity compared to the parent xylanase AM24. In an embodiment the variant polypeptide comprises an amino acid substitution at position 23 and/or 28, and lacks a disulfide bridge in the 1-191 amino acid region, and has improved thermostability and/or pH-stability compared to the parent xylanase AM24. In an embodiment the variant polypeptide comprises an amino acid substitution at position 23 and/or 28, and lacks a disulfide bridge in the 1-191 amino acid region, and has higher xylanase activity at a high temperature of at least 70° C. preferably at least 80° C., more preferably at least 90° C., when compared to the parent xylanase AM24. In an embodiment the variant polypeptide comprises an amino acid substitution at position 23 and/or 28, and lacks a disulfide bridge in the 1-191 amino acid region, and has an improved xylanase activity retention at pH of at least 7 and temperature of at least 70° C., preferably at least 80° C., more preferably at least 90° C., when compared to the parent xylanase AM24.

In an embodiment the variant polypeptide comprises at least one disulfide bridge between two Cys residues in the 1-191 amino acid region, without any further substitutions in the amino acid chain, and has improved stability and/or activity compared to the parent xylanase AM24. Such a variant may have a lower stability and/or activity than the variant polypeptide comprising additional substitution at position 23 or 28, or at positions 23 and 28. In an embodiment, the variant comprises disulfide bridge between the substituted residues T3C, T30C, and has improved stability and/or activity compared to the parent xylanase AM24. In an embodiment the variant polypeptide comprises at least one disulfide bridge between two Cys residues in the 1-191 amino acid region, without any further substitutions in the amino acid chain, and has improved thermostability and/or pH-stability compared to the parent xylanase AM24. In an embodiment the variant polypeptide comprises at least one disulfide bridge between two Cys residues in the 1-191 amino acid region, without any further substitutions in the amino acid chain, and has higher xylanase activity at a high temperature of at least 70° C. preferably at least 80° C., more preferably at least 90° C., when compared to the parent xylanase AM24. In an embodiment the variant polypeptide comprises at least one disulfide bridge between two Cys residues in the 1-191 amino acid region, without any further substitutions in the amino acid chain, and has an improved xylanase activity retention at pH of at least 7 and temperature of at least 70° C., preferably at least 80° C., more preferably at least 90° C., when compared to the parent xylanase AM24.

In an embodiment the variant polypeptide has xylanase activity and comprises at least one further amino acid substitution at a position other than position 23 or 28. In an embodiment the at least one further substitution further improves the stability and/or activity of the variant polypeptide. Thus, the claimed substitution(s) at positions 23 and/or 28 in the amino acid chain, together with the disulfide bridge between two Cys residues in the 1-191 region, can be used either as such, or with additional substituted positions to improve the performance and stability of the parent xylanase AM24. In an embodiment the variant polypeptide has xylanase activity and comprises at least one further amino acid substitution at a position other than position 23 or 28, wherein the at least one further substitution further improves the thermostability and/or pH-stability, and/or the xylanase activity retention of the variant polypeptide. Thus, the claimed substitution(s) at positions 23 and/or 28 in the amino acid chain, together with the disulfide bridge between two Cys residues in the 1-191 region, can be used either as such, or with additional substituted positions to improve the performance and thermostability and/or pH-stability of the parent xylanase AM24.

In an embodiment the total number of substitutions in the variant polypeptide compared to SEQ ID NO: 1, is 3-10, or 4-10. In an embodiment the variant has 3 substitutions, or the variant has 4 substitutions, or the variant has 5 substitutions, or the variant has 6 substitutions, or the variant has 7 substitutions, or the variant has 8 substitutions, or the variant has 9 substitutions, or the variant has 10 substitutions.

In an embodiment the variant polypeptide, or the functional fragment, has a predicted molecular weight between 19 and 26 kDa, preferably between 20 and 25 kDa, comprising the amino acids constituting the core region of the variant polypeptide, and without including a signal sequence which is cleaved off from the secretory variant polypeptide and putative pro-sequence which is cleaved off during the maturation of variant polypeptide. The predicted molecular weight can be determined by calculating the sum of the molecular weights of the individual amino acids in the variant polypeptide, or in its functional fragment.

In an embodiment the variant polypeptide has improved thermostability and/or pH-stability compared to the polypeptide having the sequence SEQ ID NO: 1. In an embodiment the variant polypeptide has an improved thermostability and pH-stability when compared to the polypeptide having the sequence SEQ ID NO: 1. In an embodiment the variant polypeptide has an improved thermostability or improved pH-stability, when compared to the polypeptide having the sequence SEQ ID NO: 1.

In an embodiment the variant polypeptide has higher xylanase activity, when compared to the polypeptide having the sequence SEQ ID NO: 1. In an embodiment the variant polypeptide has an improved xylanase activity retention, when compared to the polypeptide having the sequence SEQ ID NO: 1. In an embodiment the variant polypeptide has an improved pH and temperature dependent xylanase activity retention, when compared to the polypeptide having the sequence SEQ ID NO: 1.

In an embodiment, the at least one disulfide bridge between two Cys residues in the 1-191 amino acid region, and an amino acid substitution at the position 23 or 28, or at the positions 23 and 28 of the variant polypeptide result in an improved thermostability and/or pH-stability of the variant polypeptide, when compared to the polypeptide having the sequence SEQ ID NO: 1. In an embodiment, the at least one disulfide bridge between two Cys residues in the 1-191 amino acid region of the variant polypeptide result in an improved thermostability and/or pH-stability of the variant polypeptide, when compared to the polypeptide having the sequence SEQ ID NO: 1. In an embodiment, the amino acid substitution at the position 23 or 28, or at the positions 23 and 28 of the variant polypeptide result in an improved thermostability and/or pH-stability of the variant polypeptide when compared to the polypeptide having the sequence SEQ ID NO: 1. In an embodiment, the at least one disulfide bridge between two Cys residues in the 1-191 amino acid region, and an amino acid substitution at the position 23 or 28, or at the positions 23 and 28 of the variant polypeptide result in an improved xylanase activity retention of the variant polypeptide, when compared to the polypeptide having the sequence SEQ ID NO: 1.

In an embodiment the variant polypeptide has an improved stability and/or activity compared to the polypeptide having the sequence SEQ ID NO: 1 at reaction conditions wherein the temperature is at least 70° C., preferably at least 80° C., more preferably at least 90° C., most preferably at least 96° C. In an embodiment the variant polypeptide has an improved thermostability and/or pH-stability when compared to the polypeptide having the sequence SEQ ID NO: 1 at reaction conditions wherein the temperature is at least 70° C., preferably at least 80° C., more preferably at least 90° C., most preferably at least 96° C. In an embodiment the variant polypeptide has an improved xylanase activity retention when compared to the polypeptide having the sequence SEQ ID NO: 1 at reaction conditions wherein the temperature is at least 70° C., preferably at least 80° C., more preferably at least 90° C., most preferably at least 96° C. In an embodiment the variant polypeptide has an improved stability and/or activity compared to the polypeptide having the sequence SEQ ID NO: 1 at reaction conditions wherein the pH is at least 2, at least 3, at least 3.5, at least 4, at least 4.5, at least 5, at least 6, at least 7, at least 8, at least 9, at least 10, or at least 11. In an embodiment the variant polypeptide has an improved thermostability and/or pH-stability when compared to the polypeptide having the sequence SEQ ID NO: 1 at reaction conditions wherein the pH is at least 2, at least 3, at least 3.5, at least 4, at least 4.5, at least 5, at least 6, at least 7, at least 8, at least 9, at least 10, or at least 11. In an embodiment the variant polypeptide has an improved xylanase activity retention when compared to the polypeptide having the sequence SEQ ID NO: 1 at reaction conditions wherein the pH is at least 2, at least 3, at least 3.5, at least 4, at least 4.5, at least 5, at least 6, at least 7, at least 8, at least 9, at least 10, or at least 11. In an embodiment the variant polypeptide has improved thermostability and/or pH-stability at a temperature of at least 90° C. and/or at pH of at least 7, when compared to the parent xylanase AM24.

Providing xylanases that retain activity in temperatures above ambient temperature is advantageous for applications wherein xylan degradation is required in such process conditions. High temperature tolerance of xylanase has the benefits of increased specific activity, and the enzyme stability. Use of high reaction temperature also e.g. prevents growth of contaminants, and increases mass transfer rate as the fluid viscosity is lowered when substrate concentration is high. Using xylanase with a high stability reduces or avoids the need to change the process conditions commonly used.

Furthermore, the xylanases according to disclosure have improved stability, and xylanase activity in acid and/or neutral and/or alkaline conditions, which is advantageous, for instance, in bleaching of pulp in the alkaline or acid process conditions. In an embodiment, the xylanases according to disclosure have improved thermostability and/or pH-stability, and/or improved xylanase activity retention in acid and/or neutral and/or alkaline conditions, which is advantageous, for instance, in bleaching of pulp in the alkaline or acid process conditions.

In an embodiment, xylan degradation or modifying is carried out in an aqueous environment wherein xylanase shows activity.

In an embodiment the variant polypeptide of xylanase hydrolyses randomly the accessible β-1,4-D-xylosidic linkages.

Figure 1B:
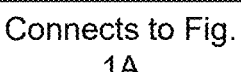

In an embodiment, the parent xylanase of the variant polypeptide according to first aspect, is one of the AM24 xylanase homologues of FIGS. 1A and 1B. In an embodiment the parent of the variant polypeptide of xylanase having at least 79%, but less than 100% amino acid sequence identity with amino acids 1-191 of SEQ ID NO: 1, is any of the homologues of the xylanase AM24 of FIGS. 1A and 1B.

In an embodiment, the variant polypeptide according to the first aspect comprises also variants of the AM24 xylanase homologues, wherein the variant of the AM24 xylanase homologue has at least 79%, but less than 100% amino acid sequence identity with amino acids 1-191 of SEQ ID NO: 1.

In an embodiment, a variant of AM24 xylanase homologue, has at least 79%, but less than 100% amino acid sequence identity with amino acids 1-191 of SEQ ID NO: 1, the amino acid sequence of the variant of AM24 xylanase homologue has xylanase activity, at least one disulfide bridge between two Cys residues in the 1-191 amino acid region, and an amino acid substitution at the position 23 or 28, or at the positions 23 and 28, the positions corresponding to the positions 23 and 28 of the SEQ ID NO: 1.

In an embodiment the variant of AM24 xylanase homologue has an improved stability and/or xylanase activity compared to the parent AM24 xylanase homologue. In an embodiment the variant of AM24 xylanase homologue has an improved stability and/or xylanase activity compared to the polypeptide having the sequence SEQ ID NO: 1. In an embodiment the variant of AM24 xylanase homologue has an improved thermostability and/or pH-stability, and/or improved xylanase activity retention when compared to the parent AM24 xylanase homologue. In an embodiment the variant of AM24 xylanase homologue has an improved thermostability and/or pH-stability and/or improved xylanase activity retention when compared to the polypeptide having the sequence SEQ ID NO: 1.

In an embodiment the variant of AM24 xylanase homologue has an improved stability and/or xylanase activity compared to the polypeptide having the sequence SEQ ID NO: 1 and/or compared to the parent AM24 xylanase homologue, at reaction conditions wherein the temperature is at least 70° C., preferably at least 80° C., more preferably at least 90° C., most preferably at least 96° C. In an embodiment the variant of AM24 xylanase homologue has an improved stability and/or xylanase activity compared to the polypeptide having the sequence SEQ ID NO: 1 and/or compared to the parent AM24 xylanase homologue, at reaction conditions wherein the pH is at least 2, at least 3, at least 3.5, at least 4, at least 4.5, at least 5, at least 6, at least 7, at least 8, at least 9, at least 10, or at least 11. In an embodiment the variant of AM24 xylanase homologue has an improved thermostability and/or pH-stability and/or improved xylanase activity retention when compared to the polypeptide having the sequence SEQ ID NO: 1 and/or when compared to the parent AM24 xylanase homologue, at reaction conditions wherein the temperature is at least 70° C., preferably at least 80° C., more preferably at least 90° C., most preferably at least 96° C. In an embodiment the variant of AM24 xylanase homologue has an improved thermostability and/or pH-stability and/or improved xylanase activity retention when compared to the polypeptide having the sequence SEQ ID NO: 1 and/or when compared to the parent AM24 xylanase homologue, at reaction conditions wherein the pH is at least 2, at least 3, at least 3.5, at least 4, at least 4.5, at least 5, at least 6, at least 7, at least 8, at least 9, at least 10, or at least 11.

In an embodiment of the second aspect of the disclosure, the present variant polypeptide of xylanase is part of a recombinant polypeptide, which is a fusion protein. The fusion protein may have other catalytic or binding activities in addition to those of xylanase. In an embodiment the variant polypeptide of xylanase is connected to the further peptides and/or polypeptides with a linker.

In an embodiment, the fusion protein comprises a signal sequence which is advantageous in the translocation of the recombinant polypeptide within and out of the host cell. In an embodiment, the signal sequence is with, or without a carrier polypeptide sequence. In an embodiment, the fusion protein comprises a carbohydrate binding moiety (CBM) as a carrier polypeptide, which is optionally a fragment of another protein or enzyme derived from the same or different organism as the variant polypeptide of xylanase. The signal sequence and carrier polypeptide may be derived from a same host, or alternatively derived from different hosts. In an embodiment, the fusion protein comprises a signal sequence originating from the same host cell, wherein the fusion protein comprising the xylanase variant polypeptide is produced in. In an embodiment the signal sequence originates from the same filamentous fungal host, wherein the fusion protein comprising the xylanase variant polypeptide is produced in. In another embodiment, the signal sequence originates from another organism.

In an embodiment, the fusion protein comprises an amino acid sequence which facilitates purification, such as His-tag or polyhistidine tag, wherein in the tag comprises a string of histidine residues.

In an embodiment, the fusion protein comprises an amino acid sequence having an enzyme activity, the said sequence with enzyme activity not being the same sequence as the amino acid sequence encoding the variant polypeptide with xylanase activity.

In an embodiment, the fusion protein comprises a carbohydrate binding moiety amino acid sequence, which provides the fusion protein with binding affinity.

In an embodiment the enzyme composition further comprises:
  a. at least one stabilizer selected from polyol, propylene glycol, polyethylene glycol, hexylene glycol, glycerol, a sugar, sugar alcohol, polysaccharide, lactic acid, peptide, surfactant, or a combination thereof; or at least one preservative or buffering agent selected from organic acid, citric acid, ascorbic acid, benzoic acid and their salts and derivatives, sodium benzoate, benzoate, hydroxybenzoate and derivatives, phosphate, sorbic acid, sodium sorbate, sorbate, salts, sodium chloride or potassium chloride, 1,2-Benzisothiazolin-3-one (BIT) or a combination thereof;
  b. optionally at least one inhibitor selected from boric acid, boric acid derivative, aromatic borate ester, 4-formylphenyl boronic acid, phenyl boronic acid derivative, a peptide compound with inhibitorial function, or a combination thereof;

c. optionally at least one enzyme selected from protease, amylase, cellulase, lipase, xylanase, mannanase, cutinase, esterase, phytase, nuclease, pectinase, pectinolytic enzyme, pectate lyase, carbohydrase, arabinase, galactanase, xanthanase, xyloglucanase, laccase, peroxidase and oxidase with or without a mediator, or a combination thereof; and d. optionally at least one filler selected from maltodextrin, flour, sodium chloride, sulfate, sodium sulfate, or a combination thereof.

The components a-d provide improved properties for the present enzyme composition. The enzyme composition is compatible with the components a-d and improves applicability of the enzyme composition in various uses. Salts, such as sodium chloride and sodium sulfate function as drying aids.

In an embodiment the enzyme composition comprising the variant polypeptide of xylanase and an additional enzyme is advantageous in providing a synergistic effect. Such additional enzymes are desired when the present enzyme composition comprising variant polypeptide of xylanase is used in e.g. pulp or silage processing or in feedstuff or foodstuff preparation. Particularly advantageous synergistic enzymes that work with xylanase in pulp or silage processing are cellulases, hemicellulases, phytases and amylases. Particularly advantageous synergistic enzymes that work with feedstuff or foodstuff preparation are cellulases, hemicellulases, phytases and amylases.

In an embodiment, the enzyme composition is provided in the form of a liquid composition or a solid composition, such as solution, dispersion, paste, powder, granule, granulate, coated granulate, tablet, cake, crystal, crystal slurry, gel, or pellet.

In an embodiment, the enzyme preparation or the enzyme composition further comprises other suitable additives selected from the group consisting of bleaching agents, anticorrosion agents, builders, anti-redeposition agents, optical brighteners, dyes, pigments, perfumes, caustics, abrasives and preservatives.

The present disclosure further relates to the use of, and a method of using the enzyme composition as herein disclosed, for degrading xylan.

In an embodiment is provided a recombinant host cell, wherein the host cell is selected from the group consisting of a. filamentous fungal cells from Division Ascomycota, Subdivision Pezizomycotina; preferably from the group consisting of members of the Class Sordariomycetes or Eurotiomycetes, Subclass Hypocreomycetidae or Sordariomycetidae or Eurotiomycetidae, Orders Hypocreales or Sordariales or Eurotiales, Families Hypocreacea or Nectriacea or Chaetomiaceae or Aspergillaceae, Genera *Trichoderma* (anamorph of *Hypocrea*) or *Fusarium* or *Acremonium* or *Humicola* or *Thermothelomyces* or *Myceliophthora* or *Aspergillus;* more preferably from the group consisting of species *Trichoderma reesei (Hypocrea jecorina), T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Acremonium (Cephalosporium) chrysogenum, Humicola insolens, Humicola grisea, Thermothelomyces thermophilus, Myceliophthora thermophila, Aspergillus niger, Aspergillus niger* var. *awamori* and *Aspergillus oryzae;*

26 b. bacterial cells, preferably gram-positive Bacilli such as *B. subtilis, B. licheniformis, B. megaterium, B. amyloliquefaciens, B. pumilus,* gram negative bacteria such as *Escherichia coli, actinomycetales* such as *Streptomyces* sp.; and c. yeasts, such as *Saccharomyces cerevisiae, Pichia pastoris, Yarrowia lipolytica;* preferably the host cell is selected from filamentous fungal cells such as *Trichoderma* or from gram-positive Bacilli such as *Bacillus;* most preferably from *Trichoderma reesei* or from *Bacillus subtilis* or *B. pumilus* or *B. licheniformis.*

In an embodiment, the recombinant host cell is selected from the group consisting of filamentous fungal cells (e.g. *Trichoderma* or *Trichoderma reesei, Aspergillus* or *Aspergillus oryzae* or *Aspergillus niger, Thermothelomyces* or *Thermothelomyces heterothallica* or *Humicola* or *Humicola insolens* or *Fusarium* or *Fusarium venenatum*), bacterial cells, preferably gram-positive Bacilli (e.g. *Bacillus subtilis, B. licheniformis, B. megaterium, B. amyloliquefaciens, B. pumilus*), gram-negative bacteria (e.g. *Escherichia coli*), actinomycetales (e.g. *Streptomyces* sp., *Nonomuraea flexuosa*) or yeasts (e.g. *Saccharomyces cerevisiae, Pichia pastoris, Yarrowia lipolytica*).

The recombinant host cell can be used to produce the variant polypeptide of xylanase and to contain a polynucleotide encoding it. The recombinant host cell can be operably linked to one or more control sequences that direct the production of the variant polypeptide of xylanase. The recombinant host cell is useful also in preparation of variants of xylanase with different properties. For example, a host cell can be selected, which provides post-translational modifications beneficial for stability or activity, or which facilitates post-processing of the variant polypeptide of xylanase produced in the host cell.

In an embodiment the host cell is non-pathogenic. This is particularly advantageous for using the host cell or its products for animal feed.

In an embodiment of the sixth aspect, the xylan containing material is plant based material or partly plant based material. In another embodiment the xylan containing material is recycled waste paper; mechanical pulp, chemical pulp, semi chemical pulp, kraft- or other paper-making pulp, wood pulp or non-wood pulp, or fibers subjected to a retting process; or guar gum or locust bean gum containing material.

In an embodiment, the present variant polypeptide of xylanase or the present enzyme composition is used in pulp processing, like pulp bleaching, promoting cellulose hydrolysis and enhancing the refining efficiency of pulp. The present variant polypeptide of xylanase is useful in facilitating the release of lignin from paper pulp and reducing the usage of the harmful bleaching agents, such as chlorine-based chemicals and sodium hydrosulfite.

In an embodiment the variant polypeptide of xylanase, or the fusion protein, or the enzyme composition according to the disclosure, is used in biomass processing and biomass hydrolysis, and in drainage improvement. The use of the present variant polypeptide of xylanase is useful in generation of biological fuels wherein xylanase can be used for the conversion of lignocellulosic raw materials to biofuel such as ethanol, from lignocellulosic biomass.

In an embodiment, wherein the present variant polypeptide of xylanase or the present enzyme is used in an animal feed, the animal is a monogastric animal or a ruminant. In another embodiment the animal is a broiler chicken, egg-laying chicken, pig, piglet, turkey, or an aquaculture organism such as fish.

In an embodiment the feed is animal feed and comprises or consists of grains and cereal such as maize and soybean meal, or wheat, oats, barley, and/or rice. In an embodiment, wherein the present variant polypeptide of xylanase or the present enzyme is used in an animal feed, at least one xylan containing product or by-product is provided in the feed. The feed, wherein the present variant polypeptide of xylanase or the present enzyme is used, has improved nutritional value compared to a feed without the variant polypeptide of xylanase. The present enzyme composition and the present variant polypeptide of xylanase degrade xylan present in the feed and thereby make it more easily digestible for the animals. In particular, the present enzyme composition and the present variant polypeptide of xylanase can digest xylans present in the feed, for example, in maize soybean containing feeds, which has beneficial effects on the intestinal microbes, and consequently on the performance of the animals. The animal feed, wherein the present variant polypeptide of xylanase or the present enzyme is used, can be formulated in the form of a wet composition or a dry composition.

In an embodiment, wherein the variant polypeptide, or the fusion protein, or the enzyme composition according to the disclosure is used in food industrial process or commercial application, the said process or application comprises, for example, extraction of coffee, plant oils, xylose (for conversion into xylitol) and starch, degumming of plant fiber sources, baking and dough conditioner industries (e.g. bread making), and beverage industries (alcoholic fermentation).

Using the present variant polypeptide, the present fusion protein and the present enzyme composition is advantageous, for example, in baking where it transforms water-insoluble xylan to soluble form, increasing binding of water resulting to decreased dough firmness and increased volume. Also, the present fusion protein and the present enzyme composition is advantageous, for example, in processing and manufacturing soya milk products because it improves yield, colour, protein content and taste of soya milk products. Using the present variant polypeptide, the present fusion protein and the present enzyme composition is advantageous in beverage industry because it improves the clarification process of drinks, such as fruit juice and wine.

EXAMPLES

Example 1. AM24 (Truncated Nf_Xyn11A) Variant Design

Variants were designed from the thermophilic AM24 xylanase (SEQ ID NO:1) with the aim to further improve its stability. AM24 is a name used for a truncated form of *Nonomuraea flexuosa* Xyn11A, Nf_Xyn11A. AM24 contains the amino acids D44-L263 of the full-length wild-type Nf_Xyn11A and thus its carbohydrate binding domain (CBM) and most of the linker region of the full-length wild-type Nf_Xyn11A have been deleted (Leskinen et al., 2005; Paloheimo et al., 2007).

In the variants, the native amino acids at positions 3 and 30 of AM24 were changed to cysteine (C) to construct a disulfide (SS) bridge to the N-terminal end. Mutations were also designed into two additional positions in the N-terminal part of the molecule, at the amino acid positions 23 and/or 28.

Table 1. contains a list of variants designed, including the names of variants, the mutations in them compared to AM24 and the SEQ ID NOs of the amino acid and nucleotide sequences. The details on construction of the expression plasmids/cassettes are described in Example 3.

TABLE 1

| AM24 variants designed | | | |
|---|---|---|---|
| Xylanase/variant code | Amino acid sequence SEQ ID NO: | Nucleotide sequence SEQ ID NO: | Mutations |
| AM24 | 1 | 48 [a] | none |
| C31-4 | 2 | 49 | T3C, A23S, S28I, T30C |
| AM24-CC | 3 | 50 | T3C, T30C |
| AM24-CC + AS | 4 | 51 | T3C, A23S, T30C |
| AM24-CC + SI | 5 | 52 | T3C, T30C, S28I |
| AM24-AS | 6 | 53 | A23S |
| AM24-SI | 7 | 54 | S28I |
| AM24-AS + SI | 8 | 55 | A23S, S28I |
| AM24 | 1 | 56 [b] | none |
| C31-4 | 2 | 57 | T3C, A23S, S28I, T30C |
| NFX1 | 9 | 58 | T3C, A23Y, S28I, T30C |
| NFX2 | 10 | 59 | T3C, A23H, S28I, T30C |
| NFX3 | 11 | 60 | T3C, A23T, S28I, T30C |
| NFX4 | 12 | 61 | T3C, A23M, S28I, T30C |
| NFX5 | 13 | 62 | T3C, A23R, S28I, T30C |
| NFX6 | 14 | 63 | T3C, A23S, S28L, T30C |
| NFX7 | 15 | 64 | T3C, A23S, S28R, T30C |
| NFX8 | 16 | 65 | T3C, A23S, S28M, T30C |
| NFX9 | 17 | 66 | T3C, A23S, S28Q, T30C |
| NFX10 | 18 | 67 | T3C, A23S, S28Y, T30C |
| NFX11 | 19 | 68 | T3C, A23S, S28W, T30C |
| NFX12 | 20 | 69 | T3C, A23S, S28T, T30C |
| NFX13 | 21 | 70 | T3C, A23S, S28N, T30C |
| NFX14 | 22 | 71 | T3C, A23S, S28V, T30C |
| NFX15 | 23 | 72 | T3C, A23R, S28L, T30C |
| NFX16 | 24 | 73 | T3C, A23R, S28Q, T30C |
| NFX17 | 25 | 74 | T3C, A23H, S28L, T30C |
| NFX18 | 26 | 75 | T3C, A23T, S28L, T30C |
| NFX21 | 27 | 76 | T3C, A23W, S28I, T30C |
| NFX22 | 28 | 77 | T3C, A23P, S28I, T30C |
| NFX23 | 29 | 78 | T3C, A23S, S28P, T30C |

[a] The nucleotide sequence SEQ ID NO: 48 is expressed from cassette pALK1502, described in details in Paloheimo et al. (2007).
[b] The nucleotide sequence SEQ ID NO: 56 contains some minor modifications in codons compared to SEQ ID NO: 48 but the encoded amino acid sequences from SEQ ID NO: 48 and SEQ ID NO: 56 are identical.

Example 2. Variant Design from Close Nf Xyn11A Homologues

A blastp (protein-protein BLAST) search of the sequences with closest homology to Nf Xyn11A (AM24) core region was performed from the NCBI protein database of non-redundant protein sequences (blast.ncbi.nlm.nih.gov/Blast.cgi?PAGE=Proteins). The amino acid sequence of Nf_Xyn11A core (amino acids 1-191 from SEQ ID NO: 1, representing the mature core region according to Leskinen et al., 2005) was used as the query sequence. The algorithm parameters were as follows: Max target sequences: 100; expect threshold: 10; word size: 6; Matrix BLOSUM62; Gap Costs: Existence: 11, Extension: 1; Compositional adjustment: Conditional compositional score matrix adjustment. The sequences of the 100 homologues were downloaded and aligned using Clustal Omega multiple sequence alignment with default settings (www.ebi.ac.uk/Tools/msa/clustalo/). The lowest identity in the sequences to AM24 core sequence was 79.0%.

An identity matrix (phylogenetic tree) was prepared from AM24 core and the 100 closest homologues of AM24. The phylogenetic tree was prepared from the aligned sequences using the Phylogenetic Tree program in the Clustal Omega web site (www.ebi.ac.uk/Tools/msa/clustalo/) and is shown in FIGS. 1A and 1B. The database codes for each xylanase sequence are included. The default settings were used in the alignment.

From the 100 AM24 xylanase homologues, six xylanases were chosen to be produced in *Trichoderma reesei*. In addition, two variants from each of the six AM24 homologues were designed. The xylanases chosen for production are shown in Table 2. Basing on the alignment of the above six amino acid sequences with AM24 sequence (SEQ ID NO:1), the amino acid sequences of the six AM24 homologues were trimmed from the N and/or C terminal end(s) to represent the putative core region of each xylanase. The alignment of AM24 and the trimmed (core) sequences of the six AM24 xylanase homologues selected to be produced is shown in FIG. 2. The AM24 core sequence includes the amino acids 1-191 from SEQ ID NO:1.

Two types of AM24 xylanase homologue variants were designed from the core sequences of each of the above-mentioned six xylanases. In the first type of variants, an SS bridge was added to the N-terminal end of the xylanase by changing the native amino acids in positions 3 and 30 to cysteines. The second type of variants were designed using the same strategy as was used for the design of AM24 variant C31-4 (Example 1, Table 1). These AM24 homologue variants contained an SS bridge (C in the positions 3 and 30) and, in addition, the amino acid at the position 23 was changed to serine and the amino acid at the position 28 to isoleucine, when these were not the native amino acids at these positions originally. The variants designed and details of the mutations made are listed in Table 2.

TABLE 2

AM24 homologues chosen for production and variants designed from them. The xylanase/variant codes, database accession number, SEQ ID NOs of the xylanase amino acid sequences (core regions) chosen for production and the SEQ ID NOs of nucleotide sequences included in the expression cassettes and the mutations in the variant sequence are listed.

| Xylanase/variant code | Database accession no | Amino acid sequence produced SEQ ID NO: | Nucleotide sequence expressed SEQ ID NO: | Mutations |
|---|---|---|---|---|
| XB1 | WP_161479642 | 30 | 79 | none |
| XB1M1 | | 31 | 80 | A3C, E30C |
| XB1M2 | | 32 | 81 | A3C, A23S, S28I, E30C |
| XB2 | WP_159945040 | 33 | 82 | none |
| XB2M1 | | 34 | 83 | A3C, E30C |
| XB2M2 | | 35 | 84 | A3C, S28I, E30C |
| XB3 | WP_132341876 | 36 | 85 | none |
| XB3M1 | | 37 | 86 | A3C, E30C |
| XB3M2 | | 38 | 87 | A3C, A23S, S28I, E30C |
| XB4 | WP_053672865 | 39 | 88 | none |
| XB4M1 | | 40 | 89 | V3C, T30C |
| XB4M2 | | 41 | 90 | V3C, A23S, S28I, T30C |
| XB5 | WP_119728792 | 42 | 91 | none |
| XB5M1 | | 43 | 92 | P3C, E30C |
| XB5M2 | | 44 | 93 | P3C, A23S, S28I, E30C |
| XB6 | 3MF6_A | 45 | 94 | none |
| XB6M1 | | 46 | 95 | T3C, T30C |
| XB6M2 | | 47 | 96 | T3C, A23S, S28I, T30C |

The identity percentages of the above amino acid sequences (SEQ ID NO:30, 33, 36, 39, 42 and 45) with AM24 core region (amino acids 1-191 from SEQ ID NO:1) were from 79.0 to 96.3%. The identity matrix was created using EMBOSS Needle Pairwise Sequence Alignment program (https://www.ebi.ac.uk/Tools/psa/emboss_needle/) with default settings (Matrix BLOSUM62, Gap Open 10, Gap Extend 0. 5, End Gap Penalty false, End Gap Open 10, End Gap Extend 0.5). The percent identity matrix is shown in Table 3.

TABLE 3

Percent identity Needle pairwise sequence alignment matrix of AM24 homologues chosen for production and as backbones for variant design. The identity percentages between the sequences are shown. The core region of AM24 (amino acids 1-191 of SEQ ID NO: 1) was aligned with the amino acid sequences of the homologues (SEQ ID NOs: 30, 33, 36, 39, 42, 45) chosen for production in *T. reesei*.

|  | AM24 | XB1 | XB2 | XB3 | XB4 | XB5 | XB6 |
|---|---|---|---|---|---|---|---|
| 1: AM24 | 100.0 | 79.4 | 81.7 | 79.0 | 79.2 | 81.4 | 96.3 |
| 2: XB1 | 79.4 | 100.0 | 79.9 | 87.2 | 79.0 | 87.1 | 75.8 |
| 3: XB2 | 81.7 | 79.9 | 100.0 | 83.1 | 78.6 | 86.1 | 78.0 |
| 4: XB3 | 79.0 | 87.2 | 83.1 | 100.0 | 81.6 | 88.2 | 75.4 |
| 5: XB4 | 79.2 | 79.0 | 78.6 | 81.6 | 100.0 | 83.6 | 75.5 |
| 6: XB5 | 81.4 | 87.1 | 86.1 | 88.2 | 83.6 | 100.0 | 77.8 |
| 7: XB6 | 96.3 | 75.8 | 78.0 | 75.4 | 75.5 | 77.8 | 100.0 |

Example 3. Construction of Expression Cassettes and Plasmids for Production of Xylanases and Xylanase Variants AM24 was expressed from two constructions. The nucleotide sequence of SEQ ID NO:48 corresponds to that included in the expression cassette pALK1502 (Paloheimo et al., 2007). In SEQ ID NO:56 an internal NruI site in AM24 encoding gene has been silenced and there are also few other modifications in the codons (for more details, see the sequence listing table). The SEQ ID NO:48 and SEQ ID NO:56, however, encode identical amino acid sequence (SEQ ID NO:1). The AM24 variants were either synthesised by PCR using pALK1502 as a template and using restriction/ligation methods or were ordered as synthetic genes. All the genes encoding the AM24 homologues and their variants were ordered as synthetic genes. The codons used in the amino acid substitutions (i.e. in mutations) of the ordered synthetic AM24 variants were selected based on the *Trichoderma reesei* codon usage. The nucleotide sequences of genes encoding the AM24 homologues were codon optimized according to the *Trichoderma reesei* codon usage. To improve the yields of bacterial xylanases the mature xylanase encoding sequences were fused to a carrier polypeptide encoding sequence in the expression constructions. The carrier used was the *T. reesei* cellobiohydrolase II (CBHII) CBD (A) and hinge (B) region from the native CBHII, as described for pALK1502 in Paloheimo et al. (2007). A sequence encoding a Kex2 protease cleavage site (RDKR) was inserted between the carrier and xylanase encoding sequences. The SEQ ID NOs of xylanase nucleotide sequences included in the expression cassettes are listed in Tables 1 and 2. The genetic constructions were expressed using the *T. reesei* cbh1 (cellobiohydrolase 1) promoter. Either *T. reesei* cbh1 or cbh2 terminator was used to terminate the transcription. Either the native or a synthetic gene encoding the *Aspergillus nidulans* acetamidase was included as a transformation marker in the expression constructions.

Example 4. Production of Xylanase and Xylanase Variants in *Trichoderma reesei*

The xylanase expression constructions were transformed to *T. reesei* protoplasts as described in Penttils et al. (1987) and Karhunen et al. (1993) either as expression cassettes isolated from the expression plasmids or as expression plasmids. From each transformation, 3-20 transformants were picked and were sporulated in potato dextrose (PD) slants. The spores from the PD slants were used to inoculate shake flask cultivations (50 mL volume). The cultivations were performed in cellulase inducing medium for 7 days (30° C., 250 rpm). After the cultivations were finished, samples were taken, fungal mycelia were removed by centrifugation (4000 rpm, 10 min) and the culture supernatants were collected for analysis.

The xylanase production was analysed using SDS-PAGE analysis and activity assay. The xylanase activity was measured according to Bailey et al. (1992) but using pH 7 (instead of 5.3) and 70° C. (instead of 50° C.) as reaction conditions.

In the SDS-PAGE gels, a protein band of expected molecular mass of the corresponding xylanase and xylanase variant was visible in all the samples. From all the xylanases, also a glycosylated form or forms were visible in the gels.

Xylanase activity could be measured, with the analysis method used, from the culture supernatants of all produced xylanases and xylanase variants with the exception of XB6 and its variants. No xylanase activity was obtained or the activity was below the detection level when measured from the culture supernatants of XB6 and its variants.

Example 5. Analysis of Xylanases and Xylanase Variants

Three different analysis methods were used to study the stabilities of the xylanases and xylanase variants in the culture supernatants:

1) The unfolding temperatures of all xylanases were analyzed using Prometheus NT.48 (NanoTemper Technologies GmbH). The analysis of AM24 and AM24 variants was performed from samples containing purified xylanases in 0.2 M glycine-NaOH buffer, the pH of which was adjusted to 10. The pH of the buffer with samples was 9.92 (the pH of the samples ranged from 4.32 to 4.38). The unfolding temperatures of AM24 homologues and their variants were analyzed directly from the culture supernatants. The temperature range used in the analysis was from 20 to 110° C. (heating rate+1° C. per minute). In addition, the unfolding temperature of AM24 and AM24 variants was also analyzed at low pH (3.5 and 4.5) in 200 mM Na-acetate buffer.

2) The thermostability was analyzed from chosen samples by using a modified Bailey et al. (1992) activity assay method as follows: reaction times used were 5 min and 60 min, reaction pH was 7 and reaction temperatures were 70, 80, 90 and 96° C. In addition, from AM24 and AM24 variant samples the thermostabilities were analyzed at pH 8 and 9 using 5 min reaction time at 70, 80, 90 and 96° C. and 60 min reaction time at 70 and 80° C.

3) The residual xylanase activity was measured from AM24 and AM24 variant samples at pH 7, 70° C., using 5 min reaction time after incubation of the samples at pH 11, 90° C. for 60 min.

The unfolding temperature of AM24 xylanase at high pH (buffer pH adjusted to 10) was 84.8° C. (Table 4). All AM24 variants, with the exception of NFX23, had higher unfolding temperature than AM24. The unfolding temperatures of the AM24 variants at high pH were from 87.6-104.3° C. (for NFX23 67.5 8C).

TABLE 4

Unfolding temperatures of AM24 xylanases and AM24 xylanase variants.

| Xylanase/variant code | Mutations | Unfolding temperature |
|---|---|---|
| AM24 | none | 84.8 |
| C31-4 | T3C, A23S, S28I, T30C | 104.2 |
| AM24-CC | T3C, T30C | 97.4 |
| AM24-CC + AS | T3C, A23S, T30C | 100.6 |
| AM24-CC + SI | T3C, T30C, S28I | 102.0 |
| AM24-AS | A23S | 87.7 |
| AM24-SI | S28I | 85.8 |
| AM24-AS + SI | A23S, S28I | 88.1 |
| NFX1 | T3C, A23Y, S28I, T30C | 95.2 |
| NFX2 | T3C, A23H, S28I, T30C | 96.3 |
| NFX3 | T3C, A23T, S28I, T30C | 102.9 |
| NFX4 | T3C, A23M, S28I, T30C | 99.4 |
| NFX5 | T3C, A23R, S28I, T30C | 102.0 |
| NFX6 | T3C, A23S, S28L, T30C | 100.7 |
| NFX7 | T3C, A23S, S28R, T30C | 101.8 |
| NFX8 | T3C, A23S, S28M, T30C | 103.0 |
| NFX9 | T3C, A23S, S28Q, T30C | 101.7 |
| NFX10 | T3C, A23S, S28Y, T30C | 102.2 |
| NFX11 | T3C, A23S, S28W, T30C | 102.4 |
| NFX12 | T3C, A23S, S28T, T30C | 102.5 |
| NFX13 | T3C, A23S, S28N, T30C | 97.6 |
| NFX14 | T3C, A23S, S28V, T30C | 104.3 |
| NFX15 | T3C, A23R, S28L, T30C | 98.6 |
| NFX16 | T3C, A23R, S28Q, T30C | 98.8 |
| NFX17 | T3C, A23H, S28L, T30C | 92.0 |
| NFX18 | T3C, A23T, S28L, T30C | 99.5 |
| NFX21 | T3C, A23W, S28I, T30C | 93.9 |
| NFX22 | T3C, A23P, S28I, T30C | 87.6 |
| NFX23 | T3C, A23S, S28P, T30C | 67.5 |

At pH 3.5 the unfolding temperature of AM24 was 61.4° C. and at pH 4.5 75.2° C. The unfolding temperature of AM24 variant C31-4 was clearly better than that of AM24 at low pH, being 84.1° C. at pH 3.5 and 105.2° C. at pH 4.5. This result shows that the described mutations improve the stability of parent xylanase in wide pH range.

The unfolding temperatures of the AM24 homologues at high pH (buffer pH adjusted to 10) were from 63.6 to 78.1° C. (Table 5). The unfolding temperatures of the variants of the AM24 homologues were improved when SS bridge was added. However, even higher improvements in unfolding temperatures were obtained when both SS bridge and the additional mutation or mutations were included at positions 23 and/or 28. The highest increases in unfolding temperatures compared to the corresponding parent xylanase were +26.8° C. for XB3M2 and +33.5° C. for XB5M2 (Table 5).

TABLE 5

Unfolding temperatures of AM24 homologues and their variants.

| Xylanase/variant code | Mutations | Unfolding temperature |
|---|---|---|
| XB1 | none | 63.6 [a) |
| XB1M1 | A3C, E30C | 73.4 |
| XB1M2 | A3C, A23S, S28I, E30C | 79.3 |
| XB2 | none | 78.1 |
| XB2M1 | A3C, E30C | 93.7 |
| XB2M2 | A3C, S28I, E30C | 96.2 |
| XB3 | none | 66.2 |

TABLE 5-continued

Unfolding temperatures of AM24 homologues and their variants.

| Xylanase/variant code | Mutations | Unfolding temperature |
|---|---|---|
| XB3M1 | A3C, E30C | 87.6 |
| XB3M2 | A3C, A23S, S28I, E30C | 93.0 |
| XB4 | none | 77.4 |
| XB4M1 | V3C, T30C | 85.3 |
| XB4M2 | V3C, A23S, S28I, T30C | 93.7 |
| XB5 | none | 63.7 |
| XB5M1 | P3C, E30C | 88.0 |
| XB5M2 | P3C, A23S, S28I, E30C | 97.2 |
| XB6 | none | 73.1[b) |
| XB6M1 | T3C, T30C | 83.0[b) |
| XB6M2 | T3C, A23S, S28I, T30C | 92.0[b) |

[a) Production yield of XB1 was low which may lead to inaccuracy in the result.
[b)No xylanase activity or activity below the detection level with the method used.

Figure 3A:
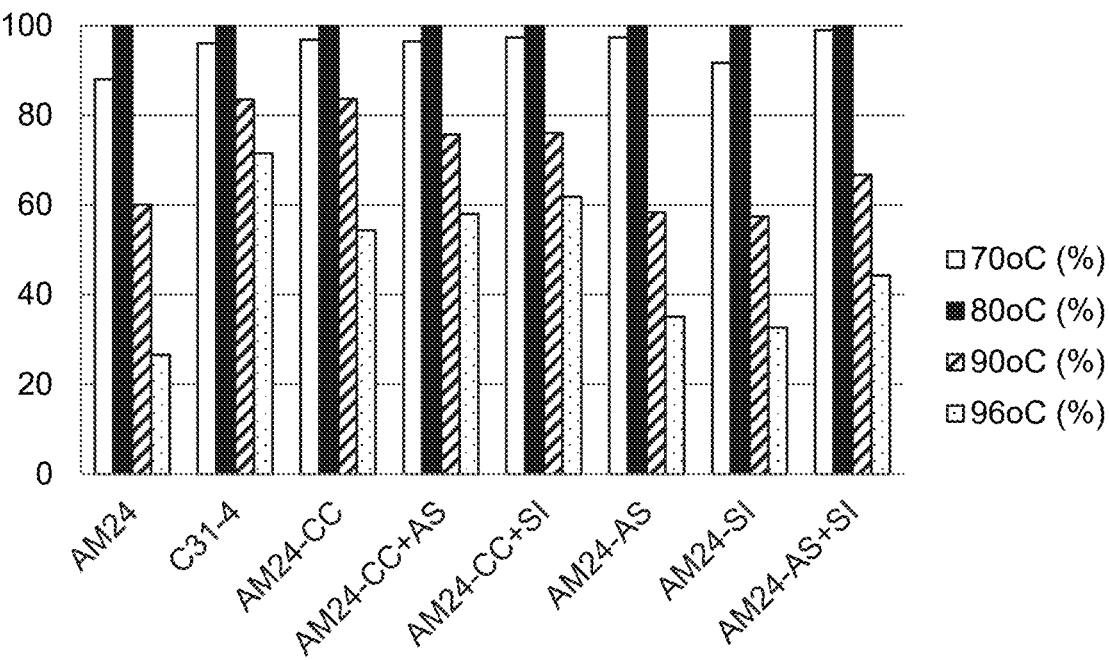
FIGS. 3A and 3B show relative thermostabilities of AM24 and its variants at pH 7. The xylanase activity analysis was performed at temperatures 70, 80, 90 and 96° C. using 5 min and 60 min reaction times.
Figure 3B:
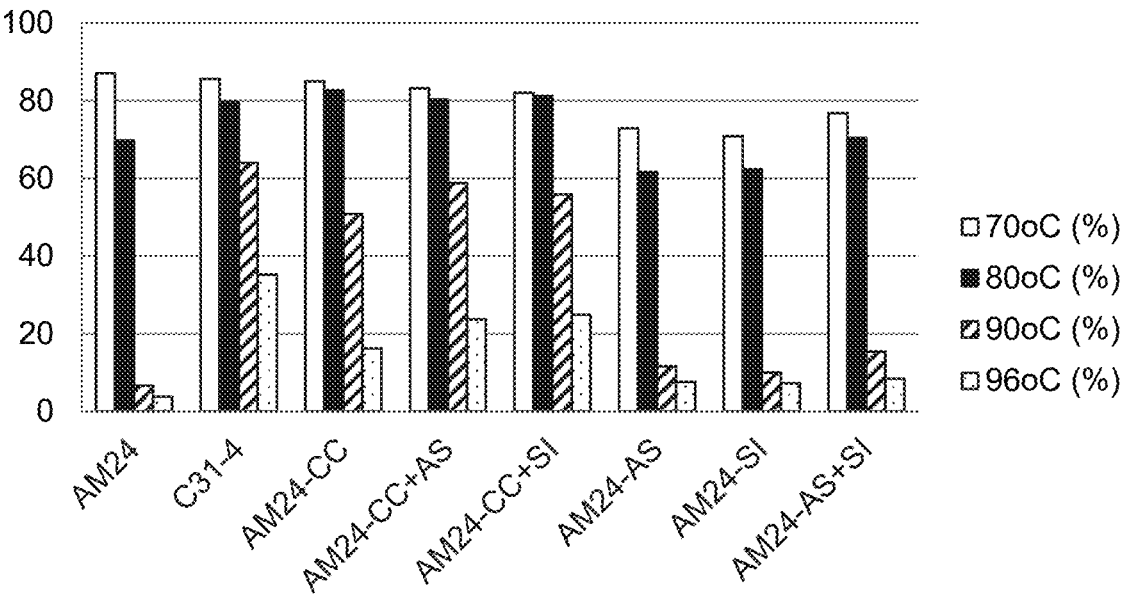

The thermostabilities were analyzed from the culture supernatants of AM24 and a selected set of its variants: the variant with the SS bridge forming mutations only (T3C and T30C; AM24-CC), variants with no SS bridge forming mutations but mutations at positions 23 and/or 28 (AM24-AS, AM24-SI, AM24-AS+SI) and variant with mutations at positions 23 and/or 28 combined with the SS bridge forming cysteine mutations (AM24-CC+AS, AM24-CC+SI, C31-4). The results from the analysis performed at pH 7 and using 5 min and 60 min reaction times are shown in FIGS. 3A and 3B, respectively. At the highest temperatures (90 and/or 96° C.) clear differences between the thermostabilities of AM24 and its variants were detected, the AM24 variants being more thermostable than AM24. Mutation at position 23 or 28 improved the thermostability of AM24. When these two mutations were combined, further improvement in thermostability was obtained. A clear improvement in the thermostability of AM24 was obtained when an SS bridge was included at the N-terminal end. However, further improvement in thermostability was detected when the position 23 or 28 mutation and the SS bridge were combined in one molecule. The best thermostability was achieved when both the position 23 and 28 mutations were combined with the SS bridge.

Figure 4A:
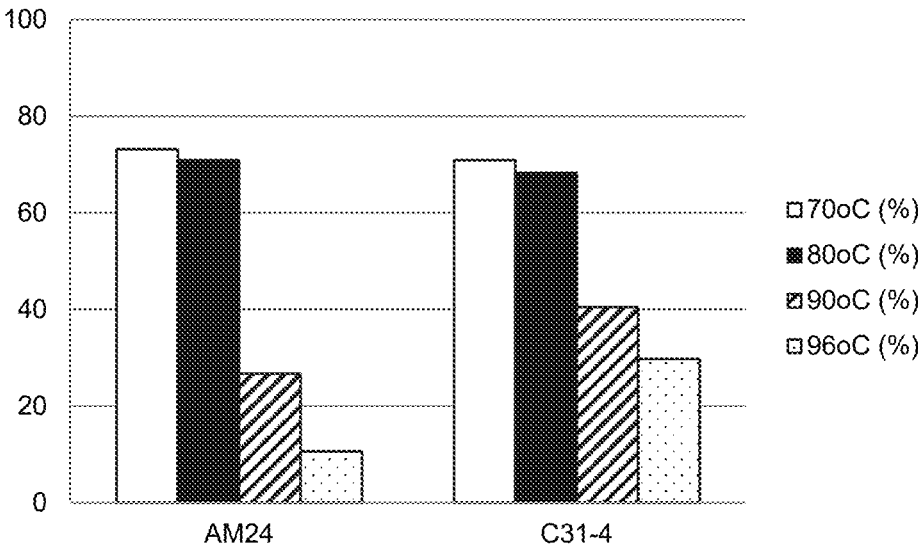
FIGS. 4A, 4B, 4C and 4D show relative thermostabilities of AM24 and its variant C31-4 at pH 8 and 9. The xylanase activity analysis was performed at 70, 80, 90 and 96° C. with 5 min reaction time and 70 and 80° C. with 60 min reaction time.
Figure 4B:
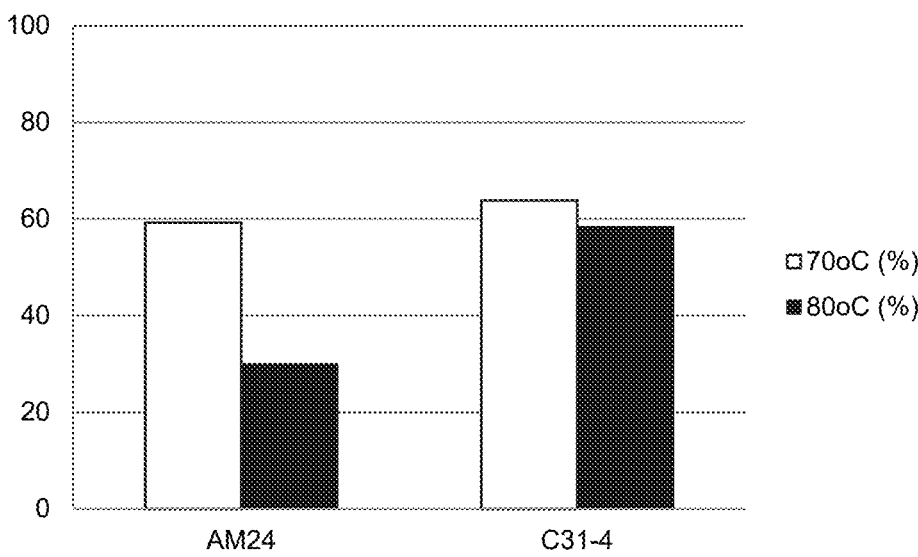
Figure 4C:
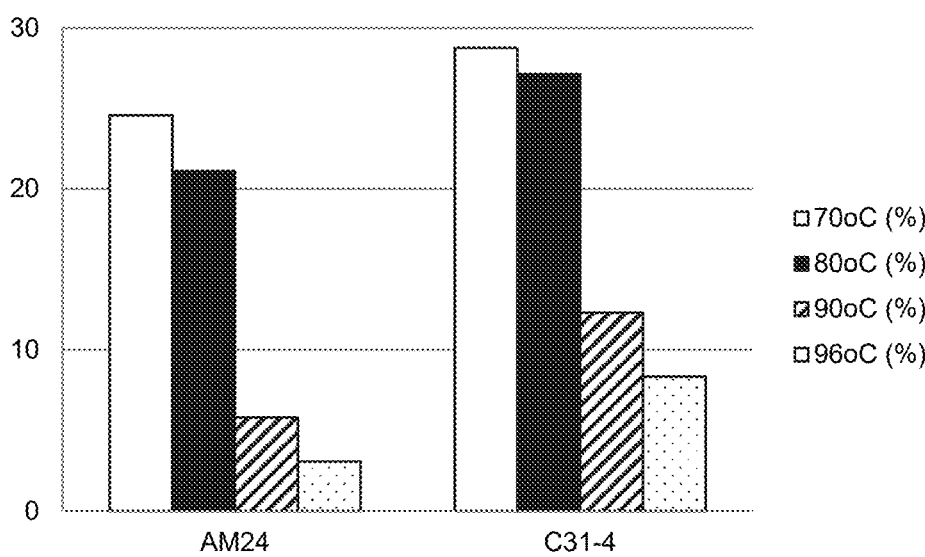
Figure 4D:
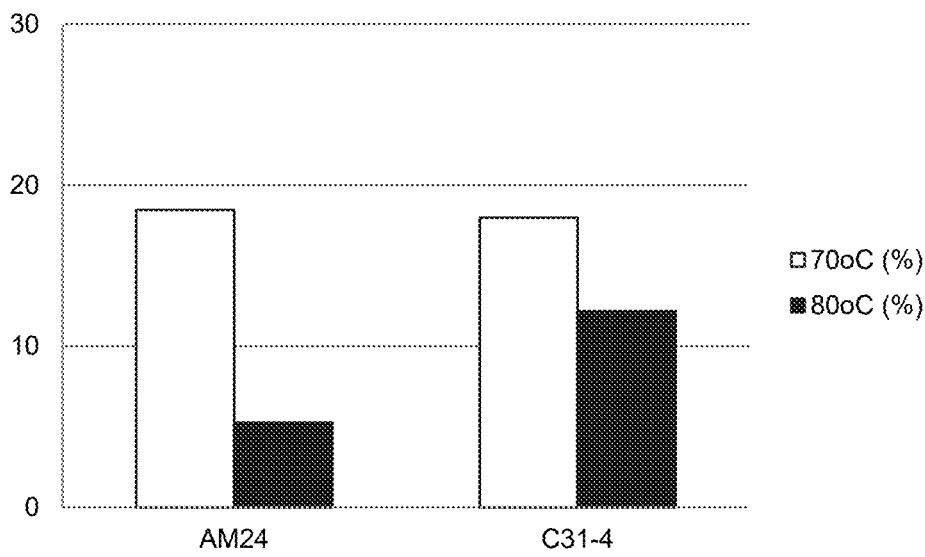

The thermostabilities of AM24 and variant C31-4 were further analyzed at higher pH values of pH 8 and 9 using 5 min and 60 min reaction times. The reaction temperatures were 70, 80, 90 and 96° C. in the 5 min assays (FIGS. 4A and 4C) and 70 and 80° C. in the 60 min assays (FIGS. 4B and 4D). In the analysis performed at pH 8 the thermostability of C31-4 in the 5 min assays was clearly better than that of AM24 in the highest tested temperatures, 90 and 96° C. (FIG. 4A) and in the 60 min assays at 80° C. (FIG. 4B). In the pH 9 analysis, the thermostability of C31-4 in the 5 min assays was clearly better in all tested temperatures (FIG. 4C), and in the 60 min assays at 80° C. (FIG. 4D).

Figure 5:
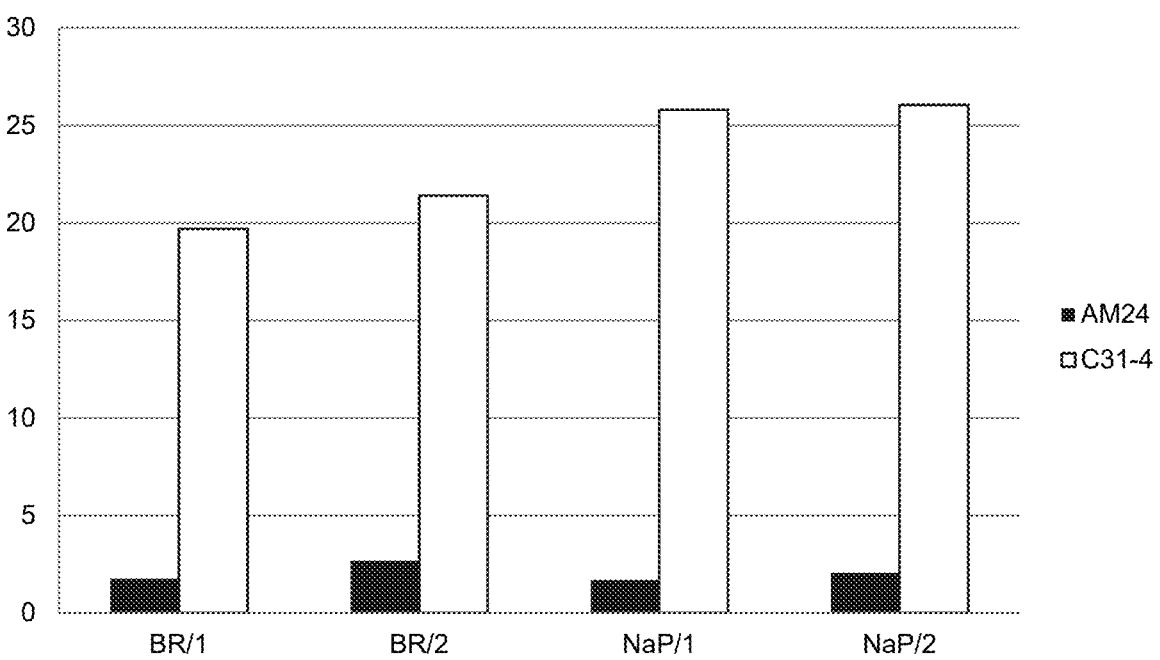
FIG. 5. Residual xylanase activities of AM24 and its variant C31-4 after 60 min incubation at pH 11, 90° C. The residual xylanase activity as percentage of the original activity in samples was analyzed at pH 7, 70° C. using 5 min reaction time. Results are from two different analysis, two parallel reactions in each. BR, Britton-Robinson buffer; NaP, natrium-phosphate buffer. The xylanase activity analyzed prior to the incubations at pH 7, 70° C. using 5 min reaction time was set as 100.

In the third thermostability test done the residual xylanase activities were measured from AM24 and C31-4 culture supernatants after incubation of the samples at pH 11, 90° C. for 60 min. The analysis was performed using two buffer systems, Britton-Robinson and Na-phosphate. The residual xylanase activity was measured using pH 7, 70° C., 5 min reaction time. C31-4 resisted the harsh conditions better than AM24. In Britton-Robinson buffer, approximately 20% (samples BR/1 and BR/2) and in the Na-phosphate buffer approximately 26% (samples NaP/1 and NaP/2) of the original activities were left in the C31-4 samples whereas only 2-3% of the original activities were left in the AM24 samples (FIG. 5).

Example 6. Production of AM24 and C31-4 Xylanases for Application Studies

The *Trichoderma* strains producing AM24 or C31-4 were cultivated in 30L bioreactors to produce material for application tests. Fermentations were performed as fed-batch cultivations in cellulase inducing medium. After the fermentations were finished, mycelia were removed by filtration steps and the culture supernatants were collected and concentrated. The resulting enzyme preparations were used in the bleaching trials.

The produced enzyme preparations of AM24 and C31-4 comprised equal amounts of corresponding xylanase enzyme, and more than half of the total protein in the said enzyme preparations consisted of the respective xylanase. Equal amounts of AM24 and C31-4 xylanases were used in the bleaching trials.

Example 7. Bleaching of *Eucalyptus* Kraft Pulp Using Xylanase Pre-Treatments at High pH and Temperature Short bleaching sequence $XD_0E$ (X, enzyme; $D_0$ (D zero), chlorine dioxide ($ClO_2$); E, extraction with sodium hydroxide) was used to compare the efficiency in bleaching of pre-treatments with AM24 and C31-4 xylanases at high temperature (90° C.). The pre-treatments were performed at two pH values, pH~8 and pH~10. The pulp used was oxygen delignified *Eucalyptus* Kraft pulp from Asian mill with kappa number 15.5 and brightness 38.0 ISO %. A constant $ClO_2$ dosage (0.2×kappa number) was used. Bleaching trials were carried out in bleaching reactors. Anchor type Kemu reactor (batch size 0.15-1.0 kg, T max 90° C., consistency 25%) was used in X- and E-stage and air heated Hellsten reactor (batch size 0.3-0.8 kg, T max 85° C., consistency 12%) in $D_0$-stage.

Approximately 2 g of total protein per ton of pulp was used. Both xylanase products contained similar relative amounts of xylanase protein (Example 6). The enzyme treatment time was 60 min.

After the enzyme stage the enzyme was deactivated by addition of hot water and immediately adjusting the pH of the pulp suspension to pH value 2.5-3. Brightness and kappa number were analysed after the E stage.

TABLE 6

Results of $XD_0E$ bleaching using eucalyptus pulp. In the REF samples, no enzyme was added. The enzyme pre-treatments were performed at 90° C. using 60 min reaction time. The aCl denotes active chlorine; ΔBr denotes difference in Brightness; and Δkappa denotes a difference in Kappa number.

| | pH 8 | | | pH 11 | | |
|---|---|---|---|---|---|---|
| | REF | AM24 | C31-4 | REF | AM24 | C31-4 |
| X | | | | | | |
| Initial pH | 8.3 | 8.3 | 8.6 | 11.0 | 10.6 | 10.6 |
| End pH | 8.3 | 8.3 | 8.3 | 10.4 | 10.4 | 10.5 |
| Kappa number | 15.1 | 14.4 | 14.7 | 14.8 | 16.6 | 16.4 |
| Brightness, % | 41.5 | 42.2 | 41.9 | 42.0 | 42.6 | 42.4 |
| $D_0$ | | | | | | |
| $ClO_2$ cons., kg aCl/t | 27.9 | 27.9 | 27.9 | 27.9 | 27.9 | 27.9 |
| Initial pH | 2.7 | 2.6 | 2.3 | 2.6 | 2.6 | 2.5 |
| End pH | 1.8 | 1.6 | 1.6 | 1.9 | 1.6 | 1.6 |
| Brightness, % | 55.6 | 56.1 | 57.0 | 56.1 | 55.3 | 57.8 |

TABLE 6-continued

Results of $XD_0E$ bleaching using eucalyptus pulp. In the REF samples, no enzyme was added. The enzyme pre-treatments were performed at 90° C. using 60 min reaction time. The aCl denotes active chlorine; ΔBr denotes difference in Brightness; and Δkappa denotes a difference in Kappa number.

| | pH 8 | | | pH 11 | | |
|---|---|---|---|---|---|---|
| | REF | AM24 | C31-4 | REF | AM24 | C31-4 |
| E1 | | | | | | |
| Initial pH | 10.8 | 11.0 | 10.9 | 11.0 | 11.0 | 10.9 |
| End pH | 10.9 | 10.9 | 10.9 | 11.0 | 10.9 | 10.9 |
| Kappa number | 6.7 | 6.4 | 5.7 | 6.2 | 6.4 | 5.9 |
| Brightness, % | 56.0 | 57.8 | 58.8 | 57.1 | 56.8 | 59.8 |
| aCl cons./ΔBr, kg/t* | 1.53 | 1.41 | 1.34 | 1.46 | 1.49 | 1.28 |
| aCl cons./Δkappa, kg/t* | 3.14 | 3.06 | 2.86 | 3.00 | 3.07 | 2.91 |

Pre-treatment with both the xylanases, AM24 and C31-4 improved the brightness of *eucalyptus* pulp. Pulp pre-treated with C31-4 at pH 8 had 2.8 units higher brightness than the reference pulp and had 1.0 units higher brightness than the pulp treated with AM24. The active chlorine (aCl) use at pH 8 per Δkappa was 0.2 kg/t and per ΔBr 0.07 kg/t lower in the C31-4 treated pulp than in AM24 treated pulp and 0.28 kg/t and 0.19 kg/t, respectively, lower than in the reference pulp (Table 6).

When the xylanase pre-treatments were performed at pH 11, AM24 treatment did not give benefits compared to reference pulp. However, C31-4 treated pulp had 2.7 units higher brightness and the active chlorine (aCl) use per Δkappa was 0.09 kg/t and per ΔBr 0.18 kg/t lower than in the reference pulp (Table 6).

The detected brightness (%) increase was significant and shows that the AM24 xylanase variant C31-4 can be used in pre-treatment or treatment of pulp and other materials at high pH and temperature.

Example 8. Bleaching of Softwood (SW) Kraft Pulp Using C31-4 at High pH and Temperature The efficiency of C31-4 in bleaching of softwood pulp at high temperature and pH was tested by using short bleaching sequence $XD_0E$ (X, enzyme; $D_0$ (D zero), $ClO_2$, chlorine dioxide; E, extraction with sodium hydroxide) with constant $ClO_2$ dosage (0.2×kappa number). Bleaching trials were carried out in bleaching reactors with whole sequence. Anchor type Kemu reactor (batch size 0.15-1.0 kg, T max 90° C., consistency 25%) was used in X- and E-stage and air heated Hellsten reactor (batch size 0.3-0.8 kg, T max 85° C., consistency 12%) in $D_0$-stage.

The pulp used in the trial was oxygen delignified SW Kraft from Scandinavian mill with following properties: kappa number 25.6, viscosity 1140 ml/g and brightness 26.8 ISO %. The dosing of C31-4 enzyme preparation was approximately 2 g of total protein per ton of pulp. The conditions used in different stages of bleaching are described in Tables 7-9.

The pulp was washed three times after the X stage. The first wash was done using water at reaction temperature (90° C.), followed by two washes with cold (4C) water. After the washing steps a centrifuge treatment (2600 rpm, 10) was performed to remove water and about 10-15 g (measured as oven dry) pulp samples were collected for analysis. In addition, dry matter analysis was done from the 31-4 treated samples using IR-dryer for better adjustment of pulp amount. Kappa number and brightness were analyzed from the pulp samples.

The results from the trial are shown in detail in Table 10.

TABLE 7

Conditions at X stage. The pH of pulp was measured in the beginning
(Target/Initial pH) and after the enzyme treatment (End pH).

| Pre-treatment | Enzyme dosage (g/t) | Pulp consistency (%) | Temperature (° C.) | Target/ Initial pH | Reaction time (min) | End pH |
|---|---|---|---|---|---|---|
| No enzyme | 0 | 10 | 90 | 10.5/10.6 | 60 | 10.7 |
| C31-4 | 75 | 9.2 | 90 | 10.5/10.8 | 60 | 10.6 |

TABLE 8

Bleaching conditions at $D_0$ stage. The amount of pulp was measured as oven dry.

| Pre-treatment | Target/ used pulp (g) | $D_0$ dosage target/used (active. Cl % of pulp) | Pulp consistency target/used (%) | Temperature (° C.) | Initial pH/end pH | Reaction time (min) | Act Cl consumption (% of pulp) |
|---|---|---|---|---|---|---|---|
| No enzyme | 215/200.3 | 5.1/5.5 | 9/8.4 | 70 | 2.6/2.1 | 30 | 5.5 |
| C31-4 | 200/178.2 | 5.1/5.7 | 9/8.0 | 70 | 3.1/2.1 | 30 | 5.6 |

TABLE 9

Bleaching condition at E stage.

| Pre-treatment | Target/ used pulp amount, g (as o.d.) | NaOH dosage target/used (% of pulp) | Pulp consistency, target/ used, % | Temperature (° C.) | Target Initial pH/ end pH | Reaction time, min |
|---|---|---|---|---|---|---|
| No enzyme | 200/185.2 | 2.3/2.5 | 10/9.3 | 80 | 10.8/10.7 | 90 |
| C31-4 | 185/159.7 | 2.3/2.7 | 10/8.6 | 80 | 10.7/10.7 | 90 |

TABLE 10

Results from the bleaching trial.

| Pre-treatment | Kappa after E-stage | Δ XDE kappa | Δ kappa/kg used act. Cl | Brightness after E-stage, ISO % | Δ XDE Brightness | Δ Brightness %/kg used act. Cl | Corrected end kappa number with the same 5.4% act. Cl consumption | Corrected end Brightness with the same 5.4% act. Cl consumption |
|---|---|---|---|---|---|---|---|---|
| No enzyme | 3.30 | 22.28 | 0.41 | 55.79 | 29.0 | 0.53 | 3.7 | 55.3 |
| C31-4 | 2.52 | 23.06 | 0.41 | 59.38 | 32.6 | 0.58 | 3.5 | 58.0 |

Softwood Kraft pulp pretreated with C31-4 at pH 10.5 had 2.7 units higher corrected end brightness with the same 5.4% active chlorine consumption compared to reference pulp (no enzyme used).

Example 9. Bleaching of Softwood (SW) Kraft Pulp Using C31-4 at High pH and Temperature in Comparison to AM24 Xylanase at Neutral pH and Lowered Temperature The bleaching test using softwood pulp and conditions like in Example 8 was repeated with the AM24 and C31-4 xylanases. The pulp was washed at pH 11 and 60° C. for about 30 minutes before its characterization and experiments. After the washing step the Kappa number of the pulp was 16.7, viscosity 1050 ml/g and brightness 32.6 ISO %. The dosing of both enzymes (C31-4 and AM24) was 2 g of total protein per ton of pulp. The conditions used in the xylanase treatment, bleaching and extraction stages are described in Tables 11-13. In the xylanase treatment stage (X-stage) the two enzymes were applied at different pH and temperature because the AM24 xylanase is known to be inactive at such pulp mill conditions while the C31-4 variant was expected, basing on previously done experiments, to be able to work at these conditions (pH 10.5/90° C.).

TABLE 11

| | Conditions X-stage. The pH of pulp was measured in the beginning (Target/Initial pH) and after the enzyme treatment (End pH). | | | | | |
|---|---|---|---|---|---|---|
| Enzyme | Enzyme dosage, g/t | Pulp consistency, % | Temperature, ° C. | Target/ Initial pH | Reaction time, min | End pH |
| 1. No enzyme | — | 10 | 90 | 10.5/10.4 | 60 | 10.4 |
| 2. AM24 | 75 | 10 | 80 | 7/7.1 | 60 | 7.1 |
| 3. C31-4 | 75 | 10 | 90 | 10.5/10.7 | 60 | 10.6 |

TABLE 12

| | Bleaching conditions Do-stage | | | | | |
|---|---|---|---|---|---|---|
| Enzyme | D0 dosage*, as act. Cl % on pulp | Pulp consistency, % | Temperature, ° C. | Initial pH/end pH | Reaction time, min | Act Cl consumption, % on pulp |
| 1. No enzyme | 3.3 | 9 | 70 | 2.8/2.1 | 30 | 3.3 |
| 2. AM24 | 3.3 | 9 | 70 | 2.5/1.6 | 30 | 3.3 |
| 3. C31-4 | 3.3 | 9 | 70 | 2.7/1.7 | 30 | 3.3 |

TABLE 13

| | Conditions E-stage | | | | |
|---|---|---|---|---|---|
| Enzyme | NaOH dosage, % on pulp | Pulp consistency, % | Temperature ° C. | Target Initial pH/ end pH | Reaction time, min |
| 1. No enzyme | 1.5 | 10 | 80 | 10.6/10.6 | 90 |
| 2. AM24 | 1.5 | 10 | 80 | 10.5/10.4 | 90 |
| 3. C31-4 | 1.5 | 10 | 80 | 10.7/10.6 | 90 |

The results from the experiments are included in Table 14.

TABLE 14

| | Results after E-stage | | | | | |
|---|---|---|---|---|---|---|
| Enzyme | Kappa number after E-stage | ΔXD0E kappa number | Δkappa number/kg used act. Cl | Brightness after E-stage, ISO % | ΔXD0E Brightness, ISO % | Δ Brightness %/kg used act. Cl |
| 1. No enzyme | 3.0 | 13.7 | 0.41 | 62.3 | 29.7 | 0.89 |
| 2. AM24 | 2.9 | 13.8 | 0.41 | 63.5 | 30.8 | 0.92 |
| 3. C31-4 | 2.5 | 14.2 | 0.43 | 65.1 | 32.4 | 0.97 |

41
42

Scandinavian Softwood Kraft pulp pretreated with C31-4 at pH 10.5/90° C. had a 2.8 units higher brightness compared to the reference pulp (no enzyme used) at identical conditions throughout the $XD_0E$ bleaching sequence. The results confirm that C31-4 improves brightness at high pH and temperature conditions. The AM24 xylanase showed a brightness gain of 1.2 units, at adjusted conditions in the X-stage (pH 7/80° C.) and identical conditions as used for C31-4 in the $D_0$- and E-stages.

Example 10. Use of thermophilic xylanase variants in feed application

The thermophilic xylanase variants described can be used in feeding of animals, e.g. pigs and broilers. They can be used alone or in combination with other enzymes, e.g. phytase and/or mannanase.

Effects of recombinant xylanase variants of the invention are studied on growth in broilers. Ultrafiltrate of the fermentation broth including the recombinant xylanase is dried and target levels applied to a pelleted broiler diet alone or in combination with a commercially available other enzymes. A control diet is fed without the xylanase enzyme. The diet is based on rye and wheat or on corn as a cereal.

Initial weight of the broilers is 38-42 g. The trial lasts for 5-6 weeks. Each treatment consists of minimum of six replicates with 10 broilers each. In each case the diet is analyzed for moisture, crude protein, crude fibre, fat, ash, and enzyme protein.

Five diets are prepared for testing with each chosen xylanase variant as described below. The parent xylanase is dosed as a reference for the treatments:

1) unsupplemented control (BD)
2) BD+chosen xylanase parent enzyme 1-10 mg/kg
3) BD+variant of above parent xylanase, same dosing as above
3) BD+chosen xylanase parent enzyme 1-10 mg/kg, different dosing compared to 1)
4) BD+variant of above parent xylanase, same dosing as above Health status and mortality of the animals is checked daily by visual inspection. At days 0, 14, 21, and 35 body weight gain (BW), feed intake (FI), and feed-conversion ratio (FCR) are measured. The FCR is calculated as the total feed consumed divided by the weight gain during the same period. Determination of the effect of the recombinant xylanase variants is based on the comparison to those animals which have been fed with the corresponding wild type xylanase and unsupplemented control feed.

Due to their high unfolding temperature, C31-4 xylanase and the other thermophilic xylanase variants designed using the same principle as disclosed herein, are suitable to all applications in which high thermostability is required, e.g. in wood and non-wood pulp applications and in feed applications in which high temperatures are used in the pelleting stage. The xylanase variants disclosed herein are also suitable to withstand and/or function in process conditions, e.g.

alkaline or acid pH, that are not optimal for the activity and function of the enzyme in question.

The foregoing description has provided by way of non-limiting examples of particular implementations and embodiments a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, some of the features of the afore-disclosed example embodiments may be used to advantage without the corresponding use of other features. Consequently, any appropriate combination of the embodiments and the aspects may be formed. Any combination of aspects or embodiments as disclosed herein may also be made without at least one non-essential feature disclosed in an aspect or embodiment.

The appended claims define the scope of protection. Any method, process, product or apparatus disclosed in the description or drawing, and which is not covered by a claim, is provided as an example which is not to be understood as an embodiment of the claimed invention, but which is useful for understanding the claimed invention.

REFERENCES

Bailey MJ, Biely P and Poutanen K. 1992. Interlaboratory testing of methods for assay of xylanase activity. J. Biotechnol. 23: 257-270.

Karhunen T, Mäntylä A, Nevalainen KMH and Suominen P. 1993. High frequency one-step gene replacement in *Trichoderma reesei*. 1. Endoglucanase I overporoduction. Mol. Gen. Genet. 241: 515-522.

Leskinen S, Mantyls A, Fagerström R, Vehmaanperä J, Lantto R, Paloheimo M and Suominen P. 2005. Thermostable xylanases, Xyn10A and Xyn11A, from the actinomycete *Nonomuraea flexuosa*: isolation of the genes and characterization of recombinant Xyn11A polypeptides produced in *Trichoderma reesei*. Appl. Microbiol. Biotechnol. 67: 495-505.

Paloheimo M., Mäntylä A., Kallio J., Puranen T. and Suominen, P. Increased production of xylanase by expression of a truncated version of the xyn11A gene from *Nonomuraea flexuosa* in *Trichoderma reesei*. 2007. Appl. Environ. Microbiol. 73: 3215-3224.

Penttils M., Nevalainen H., Rättö M, Salminen E and Knowles J. 1987. A versatile transformation system for the cellulolytic filamentous fungus *Trichoderma reesei*. Gene 61: 155-164.

Sievers F., Wilm A., Dineen D., Gibson T. J., Karplus K., Li W., Lopez R., McWilliam H., Remmert M., Söding J., Thompson J. D. and Higgins D. G. 2011. Fast, scalable generation of high-quality protein multiple sequence alignments using Clustal Omega. Mol. Syst. Biol. 7:539

The invention claimed is:

1. A variant polypeptide comprising an amino acid sequence having at least 79%, but less than 100% amino acid sequence identity with amino acids 1-191 of SEQ ID NO: 1, wherein the variant polypeptide has xylanase activity, and wherein the amino acid sequence has:

residues 3C and 30C, the positions corresponding to the positions 3 and 30 of the SEQ ID NO: 1;

at least one disulfide bridge between two Cys residues in the 1-191 amino acid region, wherein the at least one disulfide bridge is formed between the residues 3C and 30C; and an amino acid substitution at the position 23 or 28, or at the positions 23 and 28, the positions corresponding to the positions 23 and 28 of the SEQ ID NO: 1.

2. The variant polypeptide of claim 1, wherein the amino acid sequence has at least 84%, but less than 100% amino acid sequence identity with amino acids 1-191 of SEQ ID NO: 1.

3. The variant polypeptide of claim 1 comprising at least one amino acid substitution at the position A23, S23 or S28, or at the positions A23 or S23, and S28.

4. The variant polypeptide of claim 1 comprising:

a substitution of an amino acid at the position 23 to H, M, P, S, T, R, W or Y; or a substitution of an amino acid at the position 28 to I, L, M, N, P, Q, R, T, V, W or Y; or any combination thereof.

5. The variant polypeptide of claim 1, wherein the variant polypeptide has at least one of improved thermostability and pH-stability compared to the polypeptide having the sequence SEQ ID NO: 1.

6. A fusion protein, comprising the amino acid sequence of the variant polypeptide according to claim 1, and at least one of:

amino acid sequence providing a secretory signal sequence;

amino acid sequence which facilitates purification;

amino acid sequence controlling and enhancing the production of the recombinant polypeptide;

amino acid sequence encoding a protease cleavage site;

amino acid sequence having an enzyme activity; and amino acid sequence providing for the fusion protein with binding affinity.

7. An enzyme composition comprising the variant polypeptide of claim 1.

8. An enzyme composition of claim 7, further comprising:

at least one stabilizer selected from polyol, propylene glycol, polyethylene glycol, hexylene glycol, glycerol, a sugar, sugar alcohol, polysaccharide, lactic acid, peptide, surfactant, or a combination thereof; or at least one preservative or buffering agent selected from organic acid, citric acid, ascorbic acid, benzoic acid and their salts and derivatives, sodium benzoate, benzoate, hydroxybenzoate and derivatives, phosphate, sorbic acid, sodium sorbate, sorbate, salts, sodium chloride or potassium chloride, 1,2-Benzisothiazolin-3-one (BIT) or a combination thereof.

9. The enzyme composition of claim 7 in the form of a liquid composition or a solid composition.

10. A recombinant host cell comprising genetic elements for producing at least one recombinant polypeptide comprising the variant polypeptide of claim 1.

11. A recombinant host cell of claim 10, wherein the host cell is selected from the group consisting of filamentous fungal cells;

bacterial cells; and yeasts.

12. A method for producing the variant polypeptide of claim 1, comprising:

a. cultivating the recombinant host cell of claim 11 in conditions allowing production of the recombinant polypeptide; or b. cultivating as in a, and recovering the recombinant polypeptide.

13. A method for degrading or modifying xylan containing material, comprising treating said xylan containing material with an effective amount of the variant polypeptide of claim 1.

14. The variant polypeptide of claim 1, configured to be used in industrial processes or commercial applications.

15. The variant polypeptide of claim 1, configured to be used in feedstuff or foodstuff preparation.

16. An enzyme composition comprising the fusion protein of claim 6.

17. A recombinant host cell comprising genetic elements for producing at least one recombinant polypeptide comprising the fusion protein of claim 6.

18. A method for producing the fusion protein of claim 6, comprising:

a. cultivating the recombinant host cell of claim 11 in conditions allowing production of the recombinant polypeptide; or b. cultivating as in a, and recovering the recombinant polypeptide.

19. A method for degrading or modifying xylan containing material, comprising treating said xylan containing material with an effective amount of the fusion protein of claim 6.

20. A method for degrading or modifying xylan containing material, comprising treating said xylan containing material with an effective amount of the enzyme composition of claim 7.

* * * * *